(12) United States Patent
Yared et al.

(10) Patent No.: US 8,918,163 B2
(45) Date of Patent: Dec. 23, 2014

(54) ANIMAL HOLDER FOR IN VIVO TOMOGRAPHIC IMAGING WITH MULTIPLE MODALITIES

(75) Inventors: Wael I. Yared, Lexington, MA (US); Andrew K. Wilson, Arlington, MA (US)

(73) Assignee: VisEn Medical, Inc., Waltham, MA (US)

(*) Notice: Subject to any disclaimer, the term of this patent is extended or adjusted under 35 U.S.C. 154(b) by 0 days.

(21) Appl. No.: 12/934,246

(22) PCT Filed: Mar. 25, 2009

(86) PCT No.: PCT/US2009/038213
§ 371 (c)(1),
(2), (4) Date: Dec. 6, 2010

(87) PCT Pub. No.: WO2009/120758
PCT Pub. Date: Oct. 1, 2009

(65) Prior Publication Data
US 2011/0071388 A1    Mar. 24, 2011

Related U.S. Application Data

(60) Provisional application No. 61/039,377, filed on Mar. 25, 2008.

(51) Int. Cl.
*A61B 5/05* (2006.01)
*A61B 6/04* (2006.01)
*A61B 6/00* (2006.01)
*A61B 8/00* (2006.01)
*A61B 5/00* (2006.01)

(52) U.S. Cl.
CPC ............ *A61B 6/045* (2013.01); *A61B 2503/40* (2013.01); *A61B 6/0421* (2013.01); *A61B 6/485* (2013.01); *A61B 8/543* (2013.01); *A61B 5/7285* (2013.01)
USPC ........... 600/476; 600/407; 119/417; 119/421; 119/752; 119/756

(58) Field of Classification Search
USPC ............ 600/431; 119/752, 755, 417, 421
See application file for complete search history.

(56) References Cited

U.S. PATENT DOCUMENTS

| 4,367,696 A | * | 1/1983 | Hamann | ............... 119/752 |
| 5,167,160 A | * | 12/1992 | Hall, II | ............... 73/864.91 |

(Continued)

FOREIGN PATENT DOCUMENTS

| DE | 20010250 U1 | 12/2000 |
| FR | 2835541 A1 | 8/2003 |

(Continued)

OTHER PUBLICATIONS

International Search Report and Written Opinion, PCT Application No. PCT/US2009/038213, Jul. 10, 2009, 12 pages.

(Continued)

*Primary Examiner* — Jonathan Cwern
*Assistant Examiner* — Shahdeep Mohammed
(74) *Attorney, Agent, or Firm* — Choate, Hall & Stewart LLP

(57) ABSTRACT

The invention facilitates transport of an immobilized, anesthetized small animal across multiple single-modality or multiple-modality imaging workstations at the same or different physical locations without loss of subject positional information. The animal holder is compatible with preclinical animal imaging stations such as micro-CT, micro-MR, micro-PET, micro-SPECT, and FMT. The animal holder is configured to be accommodated by (for example, fit within) individual imaging chambers of such instruments and is fabricated from materials that are compliant with all of the imaging modalities used. In certain embodiments, an integrated set of fiducial marker wells accommodates the dispensing of markers that are picked up by several modalities simultaneously in multiple planes. The fiducial markers then are aligned in standard image processing or image analysis software with simple image translation and rotation operations, without the need for more advanced scaling, distortion or other operations.

37 Claims, 51 Drawing Sheets

(56) References Cited

U.S. PATENT DOCUMENTS

| | | | |
|---|---|---|---|
| 5,320,069 A * | 6/1994 | Anderson et al. | 119/751 |
| 5,960,054 A * | 9/1999 | Freeman et al. | 378/4 |
| 6,615,063 B1 | 9/2003 | Ntziachristos et al. | |
| 6,955,808 B2 * | 10/2005 | Curiel | 424/93.2 |
| 7,181,266 B2 * | 2/2007 | Frangioni et al. | 600/476 |
| 7,383,076 B2 | 6/2008 | Ntziachristos et al. | |
| 7,704,740 B2 * | 4/2010 | Schindler et al. | 435/398 |
| 7,784,429 B2 * | 8/2010 | Chiodo | 119/417 |
| 7,947,256 B2 * | 5/2011 | Rajopadhye et al. | 424/9.44 |
| 2003/0181801 A1 * | 9/2003 | Lasser et al. | 600/407 |
| 2004/0015062 A1 | 1/2004 | Ntziachristos et al. | |
| 2007/0238957 A1 * | 10/2007 | Yared | 600/407 |
| 2009/0000567 A1 * | 1/2009 | Hadjioannou et al. | 119/755 |
| 2009/0080600 A1 * | 3/2009 | Keller et al. | 378/18 |

FOREIGN PATENT DOCUMENTS

| | | |
|---|---|---|
| WO | WO-03/102558 A1 | 12/2003 |
| WO | WO-2004/072906 A1 | 8/2004 |
| WO | WO-2006020896 A2 | 2/2006 |
| WO | WO-2007089641 A2 | 8/2007 |
| WO | WO-2007/111669 A2 | 10/2007 |
| WO | WO-2009120758 A1 | 10/2009 |

OTHER PUBLICATIONS

International Preliminary Report on Patentability, PCT Application No. PCT/US2009/038213, Sep. 28, 2010, 9 pages.

Liao, Ai-Ho et al., A Three-Dimensional Registration method for MicroUS/MicroPET Multimodality Small-Animal Imaging, Ultrasonic Imaging, vol. 29, No. 3, Jul. 2007, pp. 155-155, XP008108237.

Ripoll et al., Free-Space Propagation of Diffuse Light: Theory and Experiments, Physical Review Letters, vol. 91, No. 10 (2003).

Schulz et al., Experimental Fluorescence Tomography of Tissues with Noncontact Measurements, IEEE Transactions on Medical Imaging, vol. 23, No. 4:492-500 (2004).

European Office Action, Application No. 09 724 324.0-1657, Jul. 14, 2014, 6 pages.

* cited by examiner

ANIMAL HOLDER FOR IN VIVO TOMOGRAPHIC IMAGING WITH MULTIPLE MODALITIES

CROSS-REFERENCE TO RELATED APPLICATIONS

This application is a national stage of International (PCT) Patent Application Ser. No. PCT/US2009/038213, filed Mar. 25, 2009, and published under PCT Article 21 (2) in English, which claims the benefit of and priority to U.S. Provisional Patent Application No. 61/039,377, filed Mar. 25, 2008, the entire contents of each of which are incorporated by reference herein.

GOVERNMENT RIGHTS

The invention was supported, in whole or in part, by grant 1 R44 ES012699-01 of the National Institute of Environmental Health Sciences. The Government has certain rights in the invention.

FIELD OF THE INVENTION

The invention relates generally to animal restraining systems for in vivo imaging across multiple tomographic modalities and/or imaging systems. More particularly, in certain embodiments, the invention relates to an animal holder compatible with optical imaging systems in conjunction with magnetic resonance, computed tomography, positron emission tomography, and/or other tomographic imaging systems, to enhance and simplify the registration of reconstructed datasets acquired on different systems.

BACKGROUND OF THE INVENTION

Tomography is a process that relies upon a selected form of energy being directed toward and passing through an object at more than one angle, and permits the construction of detailed images of internal structures of the object. The energy from the various angles is detected and corresponding data processed to provide a tomographic image. The received signals typically are less intense (for example, are darker) where the object is thicker or more dense, and more intense (for example, brighter) where the object is thinner or less dense.

A signal received by a single energy sensor (for example, at one angle) does not contain sufficient information to generate either a two-dimensional or a three-dimensional representation of internal structures of the object. Signals received by energy sensors arranged in a plane or volume provide sufficient information to generate a three-dimensional representation of internal structures of the object.

Tomography can be used in a variety of imaging systems with different types of transmitted and received electromagnetic radiation. In particular, in X-ray Computed Axial Tomography (CAT, or CT), X-ray radiation is projected through an object, typically at a variety of angles, and a variety of X-ray receivers, at a corresponding variety of angles, are used to receive the X-rays transmitted through the object. A computer is used to generate an image of internal structures of the object in three dimensions from signals received by the variety of X-ray receivers.

X-rays tend to pass through the object in straight lines with relatively little attenuation, allowing non-invasive capture of certain anatomical features at high resolution (for example, distinguishing features as small as 50-100 µm in one or more dimensions). X-ray CAT imaging systems can be used to image bones, organs, blood vessels, and tumors of a particular subject. While X-ray CAT imaging is able to provide high resolution of certain anatomical structures, it is relatively limited in its ability to detect, distinguish, or quantify specific chemical or biological species in the subject. Therefore, existing X-ray CAT systems cannot provide functional (or, "molecular") information about a subject or disease state at the cellular or molecular level.

Imaging techniques such as X-ray CAT, magnetic resonance imaging (MRI) and ultrasound (US) primarily rely on physical parameters such as absorption, scattering, proton density, and relaxation rates as the primary source of contrast for imaging. Specific molecular information with these modalities cannot often be obtained or is limited. Optical imaging, for example, optical tomographic imaging, uses specific molecular activity or alterations as the source of image contrast and therefore, can provide much more molecular or functional information about a subject or disease state than imaging techniques such as X-ray CAT that primarily capture anatomical information based on physical parameters.

Optical tomographic systems use one or more wavelengths of visible or invisible light, rather than X-rays. Unlike X-ray tomography, in which X-rays tend to pass through an object in a straight line with relatively little attenuation, visible and invisible (ultraviolet or infrared) light tends to be absorbed and to scatter when passing though an object. Therefore, light does not travel in straight lines when passing through the object. Light also tends to be absorbed and scattered more when passing through a relatively thick and/or non-homogeneous medium, than when passing through a relatively thin and/or homogeneous medium.

Most conventional optical tomography systems use near infrared (near-IR, NIR) light, instead of light in the visible spectrum when passing through animal tissues, since NIR tends to be absorbed less and to scatter less than visible light. The use of NIR light generally provides the ability to image deeper tissues, for example, thicker tissues, and/or the ability to image with higher sensitivity than the use of visible light.

While optical tomography is well suited to providing molecular/functional information about a subject, the achievable resolution is not as high as with X-ray CAT or MRI. Two exemplary optical tomographic techniques are Diffuse Optical Tomography (DOT) and Fluorescence Molecular Tomography (FMT). Both DOT and FMT allow optical tomographic imaging of the internal structure of animal and/or human subjects.

DOT is an imaging technique capable of providing biological functional information by imaging hemoglobin concentration and tissue oxygenation state. DOT approaches are currently being used to detect certain types of tumors, including breast tumors.

Unlike most DOT approaches, FMT uses fluorescent molecular probes, which absorb light propagating inside of an object and emit light at a longer wavelength (lower energy) than the absorbed light inside of the object, allowing non-invasive, in vivo investigation of functional and molecular signatures in whole tissues of animals and humans. FMT systems enable molecular imaging, for example, FMT can be used to visually indicate molecular abnormalities that are the basis of a disease, rather than just imaging the anatomical structures in the area of suspected molecular, abnormalities, as with conventional imaging approaches. Specific imaging of molecular targets provides earlier detection and characterization of a disease, as well as earlier and direct molecular assessment of treatment efficacy. An illustrative FMT system is described in U.S. Patent Application Publication No. US2004/0015062, the text of which is incorporated by reference herein, in its entirety.

Most existing DOT and FMT systems use light sources and light sensors in direct contact with the object to be imaged and/or use optical matching fluid. For both DOT and FMT systems, the use of fiber guides and/or optical matching fluids limits the tomographic capacity of such systems and impedes their practicality in research and/or clinical settings.

Recent improvements in fluorescence molecular tomography have led to the development of more versatile imaging techniques that do not require either direct contact or optical contact between the light sources/detectors and the object to be imaged. These techniques employ more powerful algorithms that account for heterogeneities of the index of refraction within and surrounding the animal tissue which give rise to photon reflections at the boundaries. See, for example, International (PCT) Application Publication No. WO 03/102558, published 11 Dec. 2003; and R. Schulz, J. Ripoll and V. Ntziachristos, "Experimental Fluorescence Tomography of Tissues with Noncontact Measurements," IEEE Transactions on Medical Imaging, Vol. 23, No. 4, pp. 492-500 (2004), the texts of which are incorporated herein by reference in their entirety. These techniques are further augmented by the use of so-called free-space transformations, which take into account the presence of a non-turbid medium (air) between the object to be imaged and the detectors. See, for example, International (PCT) Application Publication No. WO 2004/072906, published 26 Aug. 2004; and J. Ripoll, R. Schulz and V. Ntziachristos, "Free-Space Propagation of Diffuse Light: Theory and Experiments," Physical Review Letters, Vol. 91 No. 10 (2003), the texts of each of which are incorporated herein by reference in their entirety.

Multi-modality tomographic imaging is emerging as an increasingly important tool in pre-clinical and clinical imaging, as it allows the combination of complementary image datasets, for example, from Fluorescence Molecular Tomography (FMT), Magnetic Resonance Imaging (MRI or MR), Computed Axial Tomography (CAT or CT), Positron Emission Tomography (PET), and others, to indicate, highlight and correlate specific biological processes with morphological or functional information.

Co-registering image datasets for a given subject that are obtained from different modalities may be quite difficult because it is normally necessary to move the subject from one imaging system to another, and movement of the subject often causes complex misalignment of the datasets because the subject is not a rigid body. One approach to solving this problem is a hardware-based approach that involves a complex architecture of sources and detectors from two or more modalities within a single rotating gantry. A second approach is a software approach that involves mathematically advanced image transformation algorithms to allow the fusion of image datasets from the different imaging modalities into a single integrated dataset. The primary limitation of the hardware approach is the complexity and cost associated with multi-modality gantries. The primary limitation of the software approach resides in the relatively inferior image fusion results due to the softness or non-rigidity of biological tissue as it is transported from one imaging modality to another. Thus, there exists a need for new technologies and methods to enable the simple and accurate registration of data sets across optical, X-ray, magnetic resonance, nuclear or other tomographic modalities that overcome the limitations of existing solutions.

SUMMARY OF THE INVENTION

The invention provides a portable animal holder for use with in vivo imaging systems that features adjustable, substantially parallel (planar) frames to secure an animal within the holder. The invention enables the transport of an anesthetized, rigid or pseudo-rigid, small animal from one imaging workstation to another, or from one location to another within a single imaging workstation, without loss of subject positional information, allowing accurate co-registration of image data obtained using multiple imaging modalities. Throughout the application the terms "animal holder" and "animal cassette" are used interchangeably.

The animal holder has two substantially parallel frames that can be adjusted to accommodate a small animal (for example, a mouse or other mammal) between the frames. Each of the frames includes a window through which the electromagnetic radiation can be transmitted, as needed for the various imaging modalities used. The animal is secured between the frames, for example, by gentle compression, such that a portion of its body that is to be imaged is flush against both windows. In preferred embodiments, no harness is used, because it is not necessary to secure the animal.

In addition to maintaining subject positional information, the animal holder provides two deterministic, planar boundary conditions that are useful for quantitative tissue modeling in tomographic image reconstruction. Tomographic image reconstruction is performed, for example, in imaging systems that feature an FMT imaging modality. The planar boundary conditions offer a substantial simplification of the computations necessary for image reconstruction, thereby saving computation time and cost and improving accuracy. The flat surfaces of the animal holder have the additional advantages of being compatible with an MRI surface coil.

Thus, the animal holder enables simplified tomographic reconstruction, as well as enabling the transport of an animal subject from one workstation to another. The workstations can include single-modality and/or multiple-modality imaging workstations. The modalities may include, for example, Fluorescence Molecular Tomography (FMT), Magnetic Resonance Imaging (MRI or MR), Computed Axial Tomography (CAT or CT), Positron Emission Tomography (PET), Diffuse Optical Tomography (DOT), and/or single photon emission computed tomography (SPECT).

The animal holder is compatible with the fields of view of preclinical animal imaging stations such as micro-CT, micro-MR, micro-PET, micro-SPECT, and FMT systems (the prefix "micro-" is used to indicate a system configured for small animal imaging/analysis). The animal holder is configured to fit into an aperture (for example, as a cassette) in each of the individual imaging chambers, and the animal holder is made of materials that are compliant with all of the above modalities. Particular attention has been paid to ensuring parallelism of imaging surfaces while avoiding metal-based or other incompatible materials in the is mechanisms of the animal holder. In certain embodiments, the animal holder is fabricated from non-metallic materials.

In certain embodiments, the animal holder includes an integrated set of fiducial marker wells which accommodate fiducial markers that are detected by a plurality of imaging modalities (either simultaneously or at different times) in one or more planes. These fiducial markers then are aligned in standard image processing or image analysis software with image translation and rotation operations, without the need for more advanced scaling, distortion or other operations.

The animal holder also integrates elements for providing the animal with inhalation anesthesia, for example, isoflurane, and is designed to fit into identical receptacles inside and/or outside the imaging workstation(s) that provide heating to prevent animal hypothermia.

In one aspect, the invention provides a portable animal holder configured for use in one or more in vivo imaging systems. The animal holder including two adjustable, substantially parallel frames and a mechanism operable to secure the animal within the animal holder, thereby preventing substantial movement of the animal during imaging of the animal in the one or more in vivo imaging systems. In certain embodiments, the mechanism is operable to gently compress the animal between the substantially parallel frames. Each of the frames includes an imaging window that transmits electromagnetic radiation therethrough, for example, X-rays, gamma rays, positron rays, visible light, near-infrared light, radio waves, micro-waves, tetra-hertz radiation, infrared light, and/or ultraviolet light, for example, as required for imaging by the one or more in vivo imaging systems.

In certain embodiments, the imaging windows can be made of glass, aerogel, or plastic such as acrylic resin, Polyarylethersulfone (Radel® R PAES), polycarbonate, polyethersulfone, polypropylene, polysulfone, polyurethane resin, ALON™ and SPINEL™ Optical Ceramic or any combination thereof. The imaging windows preferably are substantially transparent to the electromagnetic radiation used to produce the image data in a given system, that is, the imaging windows allow most of the electromagnetic radiation used by a given imaging device to produce an image to pass through the window unattenuated—for example, from about 85% to about 100% of the electromagnetic radiation is not attenuated. Each of the imaging windows may have a thickness, for example, from about 0.1 mm to about 3 cm, although thicknesses greater than or less than these limits are possible. The imaging windows may have an antireflective coating. The parallel frames may be made with polyoxymethylene (e.g., Delrin®, manufactured by E.I. duPont de Nemours & Co. of Wilmington, Del.), acrylonitrile butadiene styrene (ABS), PolyEtherEther-Ketone [PEEK (30% Carbon Filled)], Self-Reinforcing Polyphenylene (TECAMAX™ SRP), Polyamide (30% Glass-Reinforced Extruded Nylon 6/6), or other plastic, for example. In preferred embodiments, particularly those using MR imaging, the animal holder is composed of non-metal, MR-compatible materials.

In preferred embodiments in which one of the imaging modalities is a tomographic imaging modality (for example, FMT), the imaging windows are substantially parallel, thereby providing two substantially planar boundary conditions for three-dimensional image reconstruction of at least a portion of the animal upon gentle compression of the animal between the substantially parallel imaging windows such that the portion of the animal of interest is flush against both windows.

In certain embodiments, the portable animal holder further includes a plurality of fiducial markers and/or wells that accommodate fiducial markers. In certain embodiments, the animal holder is configured to permit transport of the animal within the animal holder as a rigid body or pseudo-rigid body from a first imaging location to a second, different, imaging location, the fiducial markers allow co-registration of data sets obtained at the first and second imaging locations. Preferably, at least a subset of the fiducial markers are detectable by both a first imaging modality and a second imaging modality which can occur in the same or different in vivo imaging systems. For example, the fiducial markers are detectable by the first imaging modality performed with the animal at the first imaging location, and the fiducial markers are detectable by the second imaging modality performed with the animal at the second imaging location (for example, such that the animal is moved between the first and second imaging locations as a rigid or pseudo-rigid body). The first and second imaging modalities can each be chosen, for example, from among the following: magnetic resonance, X-ray, X-ray computed tomography, nuclear, positron emission tomography (PET), single photon emission computed tomography (SPECT), ultrasound, fluorescence, fluorescence tomography, and/or bioluminescence imaging. In particular embodiments, the first and second imaging modalities are selected from fluorescence molecular tomography (FMT), magnetic resonance (MR), and X-ray computed tomography (CT). In a further particular embodiment, one of the two imaging modalities is FMT and the other is MR or CT.

In certain embodiments, the fiducial markers include a fluorescent compound, a gamma emitting compound, a positron emitting compound, a silicon polymer, and/or a metal. In other embodiments, the fiducial markers are non-metal (for example, MR-compatible). In certain embodiments, the animal holder has a plurality of wells for insertion of a solid or liquid marker substance therein to provide the fiducial markers for imaging.

In certain embodiments, the fiducial markers include an organic fluorophore, an inorganic fluorophore, an indocyanine dye, quantum dots, a visible-wavelength fluorophore, an infra-red fluorophore, a superparamagnetic agent, luminous acrylic, tritium beads, deionized water, and/or a radioactive agent.

In certain embodiments, the animal holder includes an inlet for delivery of anesthesia to the animal. In certain embodiments, the animal holder includes a heater for maintaining the animal within a given temperature range before and/or during imaging. In other embodiments, the animal holder is configured to fit within a docking station in which anesthesia can be delivered and/or a heater can be used to maintain the animal within a given temperature range before, during, and/or after imaging.

In certain embodiments, the frames of the animal holder have contoured edges for reduced stray light reflection. The imaging windows optionally can include an anti-reflective coating.

The description of elements of the embodiments of other aspects of the invention can be applied to this aspect of the invention as well.

In another aspect, the invention provides a method of imaging a region within an animal, the method including: (a) administering to an animal a probe (for example, a fluorophore); (b) positioning the animal within a portable animal holder including two adjustable, substantially parallel frames, wherein each of the frames includes an imaging window that transmits electromagnetic radiation therethrough; (c) securing the animal between the frames, thereby preventing substantial movement of the animal during imaging, and thereby providing two substantially planar boundary conditions; (d) optionally, administering anesthesia and/or heat to the animal while the animal is within the animal holder; (e) positioning the animal holder within a FMT imaging device configured to accept the animal holder; (f) directing excitation light, for example, through an imaging window of the animal holder, into the animal at multiple locations to transilluminate at least a portion of the animal; (g) optionally, detecting excitation light transmitted through the animal (and, for example, transmitted through the opposite imaging window of the animal holder); (h) detecting fluorescent light emitted from the probe within the animal (and, for example, transmitted through the opposite imaging window of the imaging holder); and (i) processing data corresponding to the detected emitted fluorescent light (and, optionally, processing data corresponding to the detected transmitted excitation light) to provide a tomographic representation of the region within the animal, wherein the two substantially planar boundary conditions are used in providing the tomographic representation.

In certain embodiments, the portable animal holder comprises a plurality of fiducial markers and the method further includes: (j) detecting locations of the plurality of fiducial markers in relation to the animal while the animal holder is within the FMT imaging device; (k) positioning the animal holder within a non-FMT imaging device configured to accept the animal holder; (l) obtaining image data from at least a portion of the animal with the non-FMT imaging device and detecting locations of the plurality of fiducial markers in relation to the animal while the animal holder is within the non-FMT imaging device; and (m) co-registering the tomographic representation obtained using the FMT imaging device with image data obtained using the non-FMT imaging device to produce a composite image of the region within the animal.

In certain embodiments, the non-FMT imaging device is a MR imaging device or a CT device. In certain embodiments, step (m) includes co-registering the FMT tomographic representation with the non-FMT image data using one or more affine transformations.

In certain embodiments, the non-FMT imaging device may employ one or more of the following imaging modalities: magnetic resonance, X-ray, X-ray computed tomography, nuclear, positron emission tomography (PET), single photon emission computed tomography (SPECT), ultrasound, and/or bioluminescence imaging.

In certain embodiments, the fiducial markers include a fluorescent compound, a gamma emitting compound, a positron emitting compound, a silicon polymer, and/or a metal. In other embodiments, the fiducial markers are non-metal (for example, MR-compatible). In certain embodiments, the animal holder has a plurality of wells for insertion of a solid or liquid marker substance therein to provide the fiducial markers for imaging.

In certain embodiments, the fiducial markers include an organic fluorophore, an inorganic fluorophore, an indocyanine dye, quantum dots, a visible-wavelength fluorophore, an infra-red fluorophore, a superparamagnetic agent, and/or a radioactive agent. In certain embodiments, the animal is a mammal, for example, a rodent, for example, a mouse.

The description of elements of the embodiments of other aspects of the invention can be applied to this aspect of the invention as well. For example, elements of the embodiments of the animal holder described above may be used in the imaging methods described herein.

In yet another aspect, the invention provides a method of imaging a region within an animal. The method comprises the steps of: (a) positioning an animal within a portable animal holder including two adjustable, substantially parallel frames, wherein each of the frames includes an imaging window that transmits electromagnetic radiation therethrough; (b) securing the animal between the frames, thereby preventing substantial movement of the animal during imaging and thereby permitting transport of the animal within the animal holder as a rigid body or pseudo-rigid body; (c) positioning the animal holder within a first imaging device configured to accept the animal holder; (d) obtaining image data using the first imaging device; (e) removing the animal holder from the first imaging device and positioning the animal holder within a second imaging device configured to accept the animal holder; (f) obtaining image data using the second imaging device; and (g) co-registering image data obtained from the first imaging device and the second imaging device to produce a composite image of a region within the animal. In certain embodiments, step (g) includes co-registering the image data using one or more affine transformations. In certain embodiments, the animal holder comprises a plurality of fiducial markers and the method comprises the step of detecting a position of each of one or more of the fiducial markers, and wherein step (g) comprises co-registering the image data using the one or more detected positions.

In certain embodiments, the first imaging device employs one or more of the following imaging modalities: magnetic resonance, X-ray. X-ray computed tomography, nuclear, positron emission tomography (PET), single photon emission computed tomography (SPECT), ultrasound, fluorescence, fluorescence (molecular) tomography (FMT), and/or bioluminescence imaging. In certain embodiments, the second imaging device employs one or more of the following imaging modalities: magnetic resonance, X-ray, X-ray computed tomography, nuclear, positron emission tomography (PET), single photon emission computed tomography (SPECT), ultrasound, fluorescence, fluorescence (molecular) tomography (FMT), and/or bioluminescence imaging. In certain embodiments, either the first or the second imaging device employs FMT, and the other employs a non-FMT imaging modality.

In certain embodiments, the fiducial markers include a fluorescent compound, a gamma emitting compound, a positron emitting compound, a silicon polymer, and/or a metal. In other embodiments, the fiducial markers are non-metal (for example, MR-compatible). In certain embodiments, the animal holder has a plurality of wells for insertion of a solid or liquid marker substance therein to provide the fiducial markers for imaging.

In certain embodiments, the fiducial markers include an organic fluorophore, an inorganic fluorophore, an indocyanine dye, quantum dots, a visible-wavelength fluorophore, an infra-red fluorophore, a superparamagnetic agent, and/or a radioactive agent.

In certain embodiments, the animal is a mammal, for example, a rodent, for example, a mouse.

The description of elements of the embodiments of other aspects of the invention can be applied to this aspect of the invention as well. For example, elements of the embodiments of the animal holder described above may be used in the imaging methods described herein.

Where FMT is one of the modalities, it is appreciated that one or more fluorophores can be detected. The one or more fluorophores can include an endogenous fluorophore and/or an exogenous (delivered) probe. The one or more fluorophores can include one or more examples of one or more of the following: a fluorescent molecular probe, an activatable fluorescent probe, an enzyme-activatable fluorescent probe, a quantum dot-based imaging probe, a fluorescent nanoparticle-based imaging probe, and/or a fluorescent probe targeted to a biomolecule. These materials can also (or alternatively) be used and detected as a fiducial marking substance. Other materials that can be detected by one or more modalities of a multiple-modality system of the present invention (detected as an endogenous substance in the animal, a substance administered to the animal, and/or a fiducial marking substance) include, for example: a wavelength shifting beacon, a multicolor fluorescent probe, a probe with high binding affinity to a target, a non-specific imaging probe, labeled cells, X-ray contrast agent, magnetic resonance contrast agent, a dual modality agent, an optical/CT dual modality agent (for example, an optical agent physically or chemically bound to a CT agent), an optical/MR dual modality agent (for example, an optical agent physically or chemically bound to an MR agent), a fluorescent lanthanide metal-ligand probe, a probe targeted to a biomarker, a molecular structure, a mineral (for example, hydroxyapatite), a biomolecule, and/or any combination of these. Where the probe is targeted to a biomolecule, the biomolecule can include, for example, one or more examples of one or more of the following: an antibody, a protein, a glycoprotein, a cell receptor, a neurotransmitter, an integrin, a growth factor, a cytokine, a lymphokine, a lectin, a selectin, a toxin, a carbohydrate, an internalizing receptor, an enzyme, a protease, a virus, a bacteria, a microorganism, and/or any combination thereof.

When an FMT modality is used, the light detected by the imaging system preferably includes excitation light from the light source that has been transmitted through the object and fluorescent light emitted from one or more fluorophores within the object. Data corresponding to the excitation light transmitted through the object, or intrinsic light, can be used to correct/calibrate captured fluorescent measurements, thereby providing more accurate tomographic images. The one or more fluorophores emit fluorescent light as a result of excitation by the excitation light. Background fluorescence can be accounted for by obtaining background measurements and processing data corresponding to the captured fluorescent light accordingly. For example, a background signal can be detected and used to generate a corrected measurement of the detected fluorescent light and/or a corrected measurement of the detected excitation light; the corrected measurement(s) can be used in the optical tomographic reconstruction. Image processing can include (i) generating a corrected measurement of the detected fluorescent light and a corrected measurement of the detected excitation light using data corresponding to the detected background light, (ii) generating a calibrated fluorescent measurement from the corrected fluorescent measurement and the corrected excitation light measurement, and (iii) using the calibrated fluorescent measurement in the optical tomographic reconstruction.

In FMT systems, processing includes simulating photon propagation at the excitation wavelength and simulating photon propagation at the emission wavelength in an optical tomographic reconstruction.

Methods of the invention can further include the step of using the tomographic image to perform one or more of the following: identifying an area of disease; distinguishing between diseased and normal tissue; localizing diseased tissue; detecting a boundary of a lesion; detecting a tumor; locating a boundary of a tumor; localizing a cell type; and/or characterizing a disease. Where the method includes the step of using the tomographic image to identify an area of disease, the disease may include at least one or more examples of one or more of the following: inflammation, cancer, cardiovascular disease, dermatologic disease, ophthalmic disease, infectious disease, immunologic disease, central nervous system disease, inherited disease, metabolic disease, environmental disease, and/or bone-related disease.

In certain embodiments, the steps of the method are repeated to obtain a plurality of tomographic images. The method permits the collection of a plurality of images because radiopharmaceuticals do not need to be used and radiotoxicity is not a concern, unlike in nuclear tomographic systems.

For example, in certain embodiments, the plurality of tomographic images are obtained as a function of time following administration of one or more probes including at least one of the one or more fluorophores. The plurality of tomographic images can be used, for example, to monitor localization of a cell type, monitor expression of a gene, monitor progression of a disease, and/or monitor a therapeutic response, for example, in drug development.

The step of monitoring localization of a cell type may include one or more examples of one or more of the following cell types: T-cells, tumor cells, immune cells, stem cells, and/or any combination thereof. The method may include the step of monitoring expression of a gene, where the gene encodes a fluorescent protein detected as one of the one or more fluorophores within the object. The step of monitoring therapeutic response can include performing one or more of the following using the plurality of tomographic images: (i) determining efficacy of an administered pharmacological substance; (ii) customizing dosage of a pharmacological substance; (iii) formulating a pharmacological substance; (iv) customizing a formulation of a pharmacological substance; (v) determining pharmacokinetic parameters of a pharmacological substance; and/or (vi) customizing a combination of pharmacological substances for the treatment of a disease.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate the same or similar parts throughout the various views.

FIG. 50 provides, by way of example, a sample procedure for co-registering (for example, fusing) data sets by minimizing the error between centers of mass of the fiducials.

DETAILED DESCRIPTION

Figure 1:
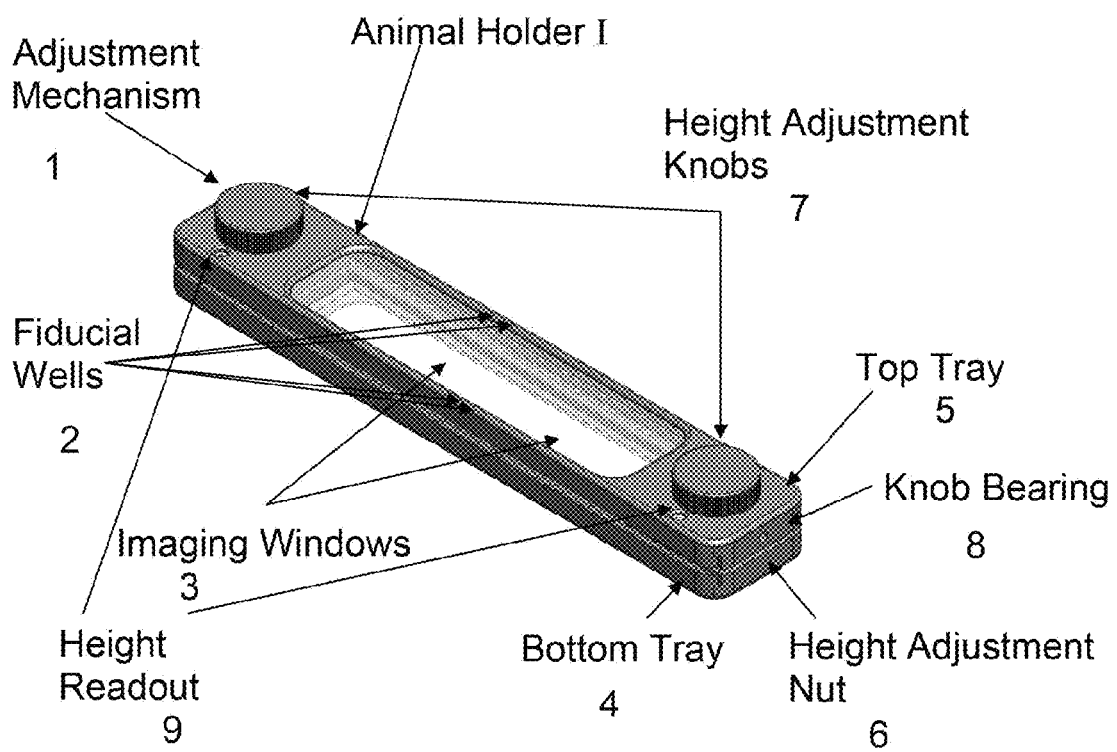
FIG. 1 is an isometric view of the animal cassette, for example, a small animal cassette, for multimodality imaging in accordance with an embodiment of the present invention.
Figure 2:
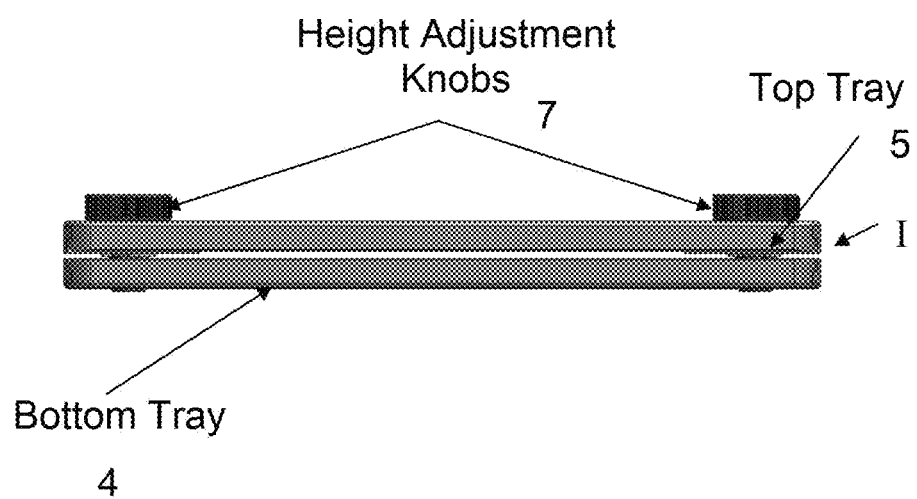
FIG. 2 is a side view of the animal cassette shown in FIG. 1, according to an illustrative embodiment of the invention.
Figure 3:
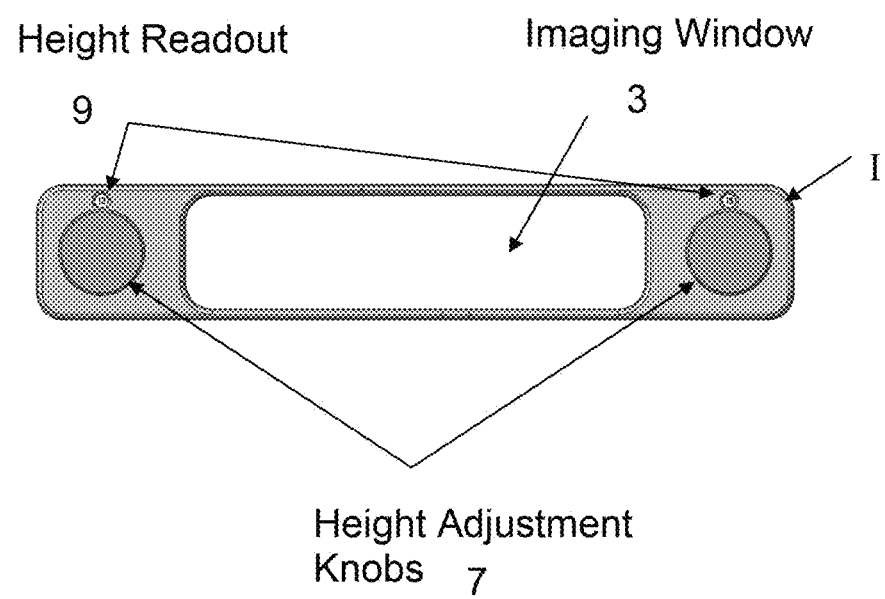
FIG. 3 is a top plan view of the animal cassette shown in FIG. 1, according to an illustrative embodiment of the invention.
Figure 4:
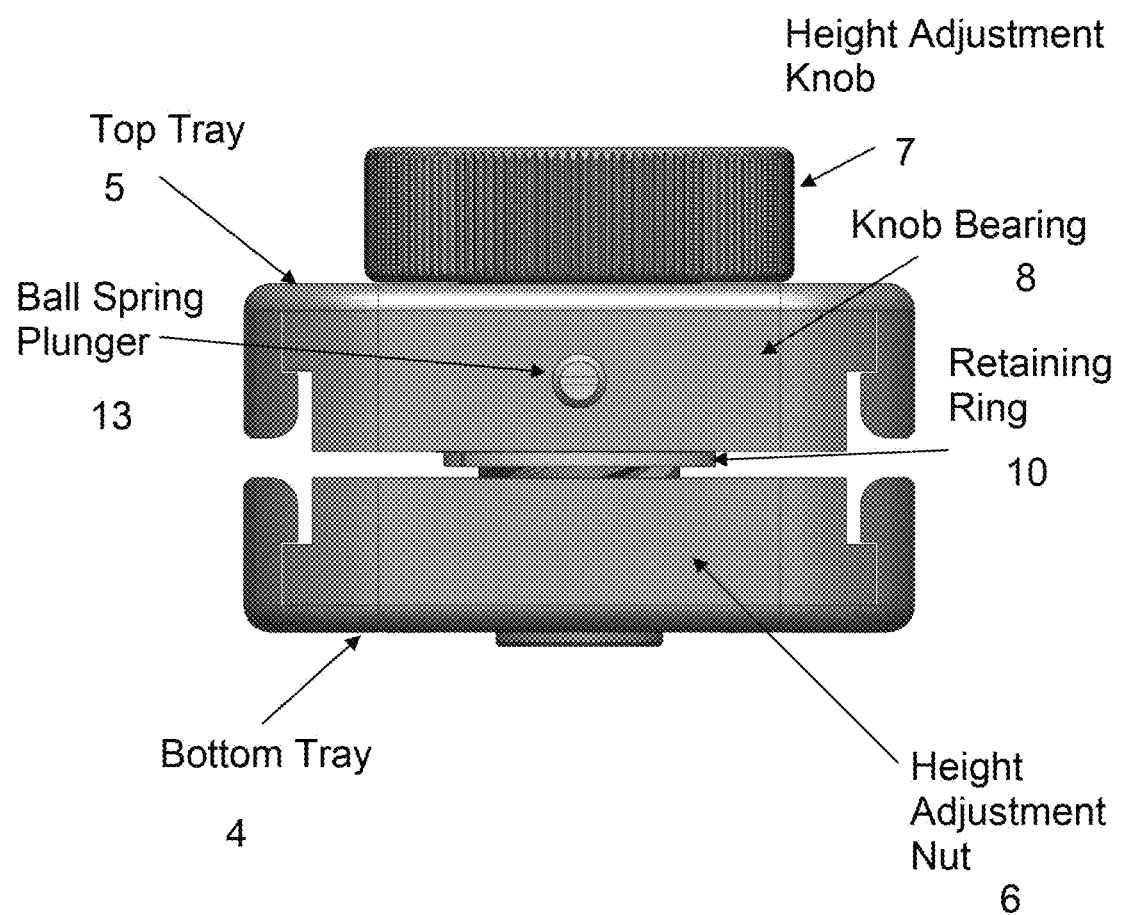
FIG. 4 is an end view of the animal cassette shown in FIG. 1, according to an illustrative embodiment of the invention.

It is contemplated that methods, systems, and processes described herein encompass variations and adaptations developed using information from the embodiments described herein.

Throughout the description, where systems and compositions are described as having, including, or comprising specific components, or where processes and methods are described as having, including, or comprising specific steps, it is contemplated that, additionally, there are systems and compositions of the present invention that consist essentially of, or consist of, the recited components, and that there are processes and methods of the present invention that consist essentially of, or consist of, the recited processing steps.

The mention herein of any publication, for example, in the Background section, should not be construed as an admission that the publication serves as prior art with respect to any of the claims presented herein.

As used herein, the term "image" is understood to mean a visual display or any data representation that may be interpreted for visual display. For example, a three-dimensional image may include a dataset of values of a given quantity that varies in three spatial dimensions. A three-dimensional image (for example, a three-dimensional data representation) may be displayed in two-dimensions (for example, on a two-dimensional screen, or on a two-dimensional printout).

As used herein, the term "map" is understood to mean a visual display, or any data representation that may be interpreted for visual display, which contains spatially-correlated information. For example, a three-dimensional map of a given volume may include a dataset of values of a given quantity that varies in three spatial dimensions throughout the volume, and the three-dimensional map may be displayed in two-dimensions.

FIGS. 1-14 illustrate one embodiment of the present invention where an animal holder I for multimodality tomographic imaging includes an adjustment mechanism 1, fiducial wells 2 and two imaging windows 3, one disposed in the bottom tray 4 and one in the top tray 5. The adjustment mechanism 1 repeatably and deterministically set the separation distance and parallelism of the two imaging windows.

Figure 5:
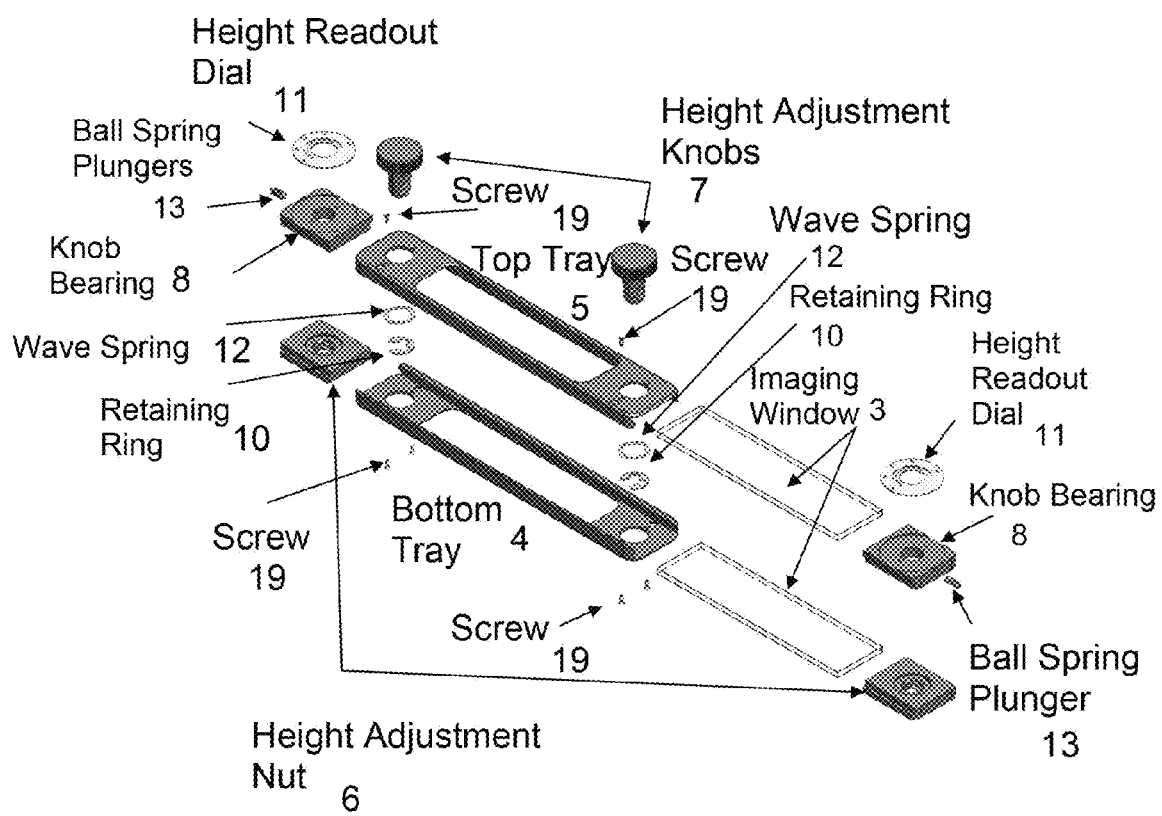
FIG. 5 is an exploded assembly of the animal cassette shown in FIG. 1, according to an illustrative embodiment of the invention.

The adjustment mechanism 1 in a preferred embodiment includes height adjustment knobs 7, knob bearings 8, retaining rings 10, height readout dials 11, wave springs 12, ball spring plungers 13, height adjustment nuts 6, screws 19, top tray 5 and bottom tray 4 (see FIG. 5). In general, all of the components with the possible exception of the ball spring plungers 13 and wave springs 12 may be molded, cast, or machined out of plastics, resins, or non-ferrous metals such as stainless steel, aluminum, titanium or beryllium copper. The height adjustment knobs 7, knob bearings 8, height adjustment nuts 6, and top tray 5 and bottom tray 4 may also be rapid prototyped out of plastics, resins, etc. The imaging windows 3 should be translucent for optical FMT imaging, MR imaging, and CT imaging. Although translucent glass is preferred, plastics, resins, and other similar materials can be used.

Figure 6:
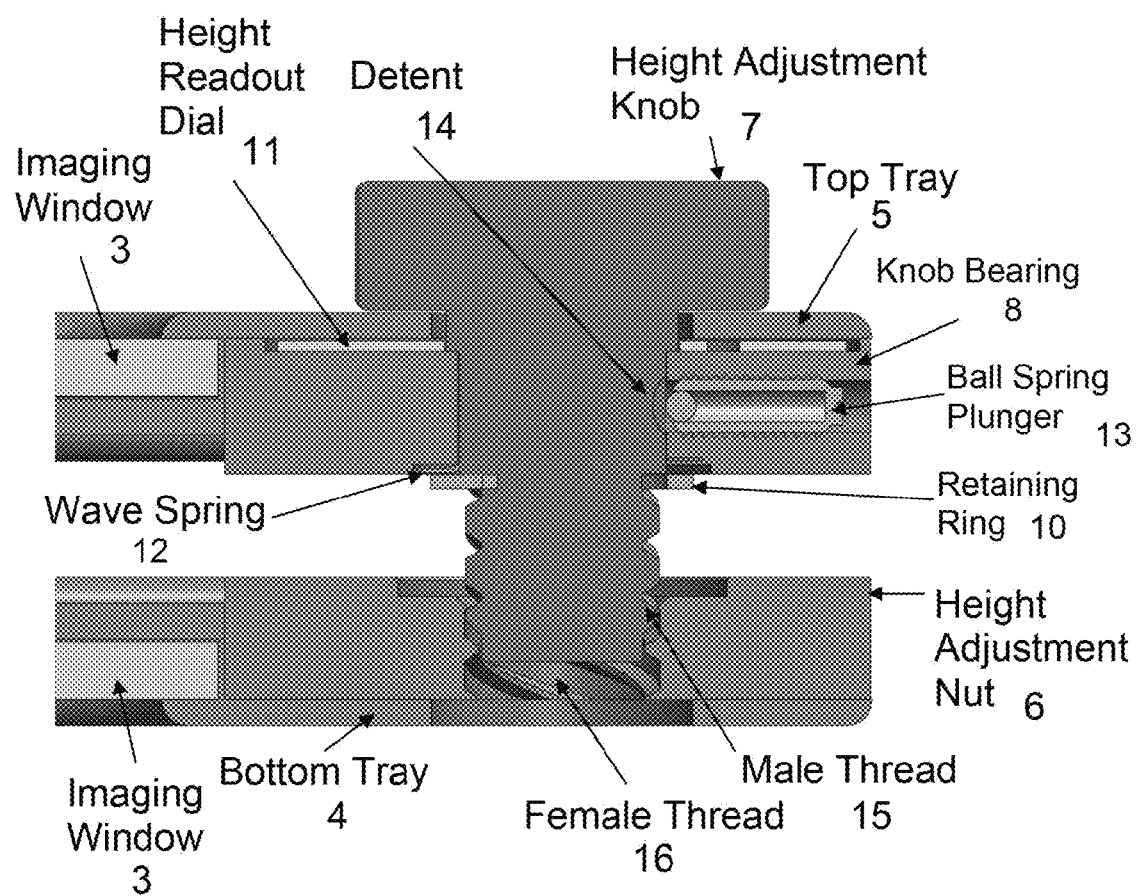
FIG. 6 is a cross-sectional view of the animal cassette shown in FIG. 1, taken at the center of the height adjustment knob along the longitudinal axis, according to an illustrative embodiment of the invention.
Figure 7:
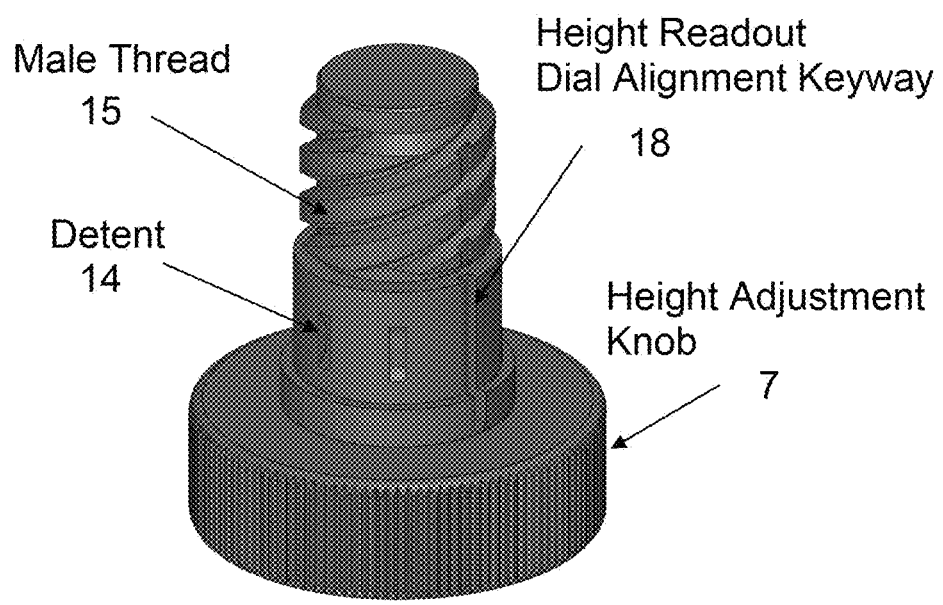
FIG. 7 is an isometric view of the adjustment knob, according to an illustrative embodiment of the invention.

The height adjustment knobs 7 allow the user to deterministically and repeatably set the distance between top tray 5 and bottom tray 4 to discrete distances and maintain parallelism. Gentle compression of the specimen between the top tray 5 and bottom tray 4 ensures that the animal does not move during imaging, during transport to the different imaging modalities, and also gives two deterministic boundary conditions for modeling the mouse tissue for quantitative FMT reconstruction. Height readouts 9 show the relative heights of the adjustment knobs 7. As shown in FIG. 5-7, ball spring plungers 13 ride into the detents 14 in the side of the height adjustment knobs 7 forcing the height adjustment knobs 7 into repeatable and deterministic angular orientations. The height adjustment knob rotations are converted to linear motion via threads between the height adjustment knobs 7 and height adjustment nuts 6; thus setting the distance between the top tray 5 and bottom tray 4. The height adjustment knob 7 is secured to the knob bearing 8 by way of a wave spring 12 and a retaining ring 10 (see FIG. 6). The knob bearing 8 is secured to the top tray 5 via the T slot cutout 17, height adjustment knobs 7, and screw 19 (see FIGS. 6 and 17). The height adjustment knob 7 contains a male thread 15 that corresponds to female thread 16 defined by height adjustment nut 6 (see FIG. 6). Height adjustment knob 7 also defines a dial alignment keyway 18 (see FIG. 7), that interfits with height readout dial adjustment key 20 defined by height readout dial 11 (see FIG. 9). The height readout dial alignment key 20 engages with height readout dial alignment keyway 18 (see FIGS. 7-9). When assembled, screw 19 and screw cutout 21 (see FIGS. 8 and 9) provide a positive stop for the height adjustment knob 7 at the low position "13" and top position "Off," when height adjustment knob 7 is rotated.

Figure 8:
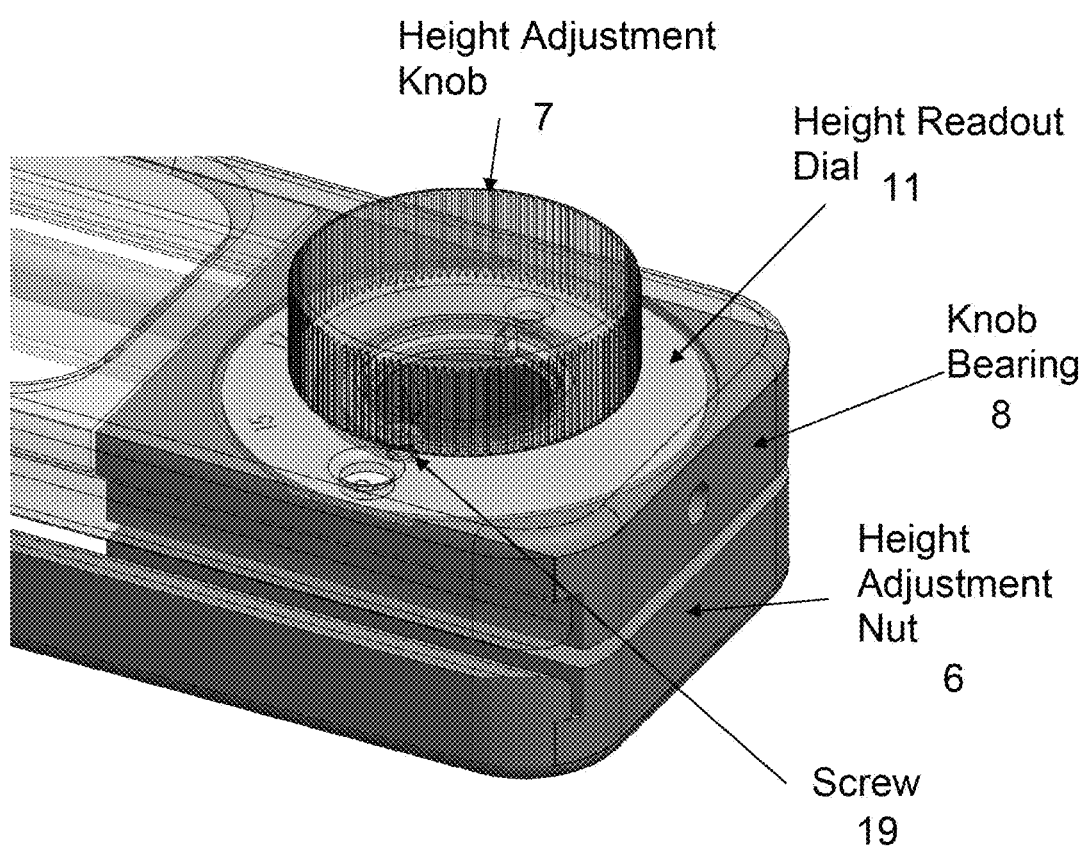
FIG. 8 is a partial trimetric view of a dial-readout gauge embedded within the animal cassette shown in FIG. 1, according to an illustrative embodiment of the invention.
Figure 9:
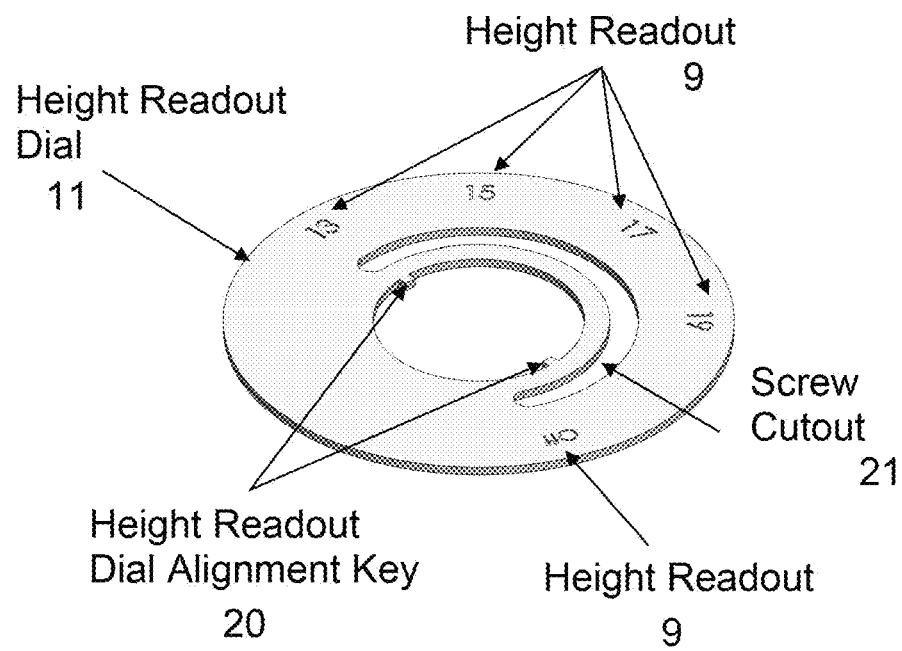
FIG. 9 is an isometric view of the dial-readout gauge, according to an illustrative embodiment of the invention.

In one embodiment, height readout dial 11 allows the user to determine the distance between top tray 5 and bottom tray 4 (see FIG. 5, 6, 8). The height readout dial 11 is keyed to the height adjustment knob 7 and the current height setting can be viewed through apertures defined by the top of top tray 5 (see FIGS. 3, 8, 9). Setting both adjustment knobs to the same height ensures that the imaging windows 3 are parallel and separated by a known distance and are held to strict tolerances.

The height adjustment nut 6 is secured to the bottom tray 4 via T-slot cutout 17 and screws 19 (see FIG. 5, 11). Imaging windows 3 made of glass or translucent plastic allow tomographic imaging of the specimen within the animal cassette. The windows may be epoxy glued or cast into top tray 5 and bottom tray 4 during the manufacturing and assembling process to secure the window within the cassette and increase the stiffness of the animal holder (see FIG. 5).

Figure 10:
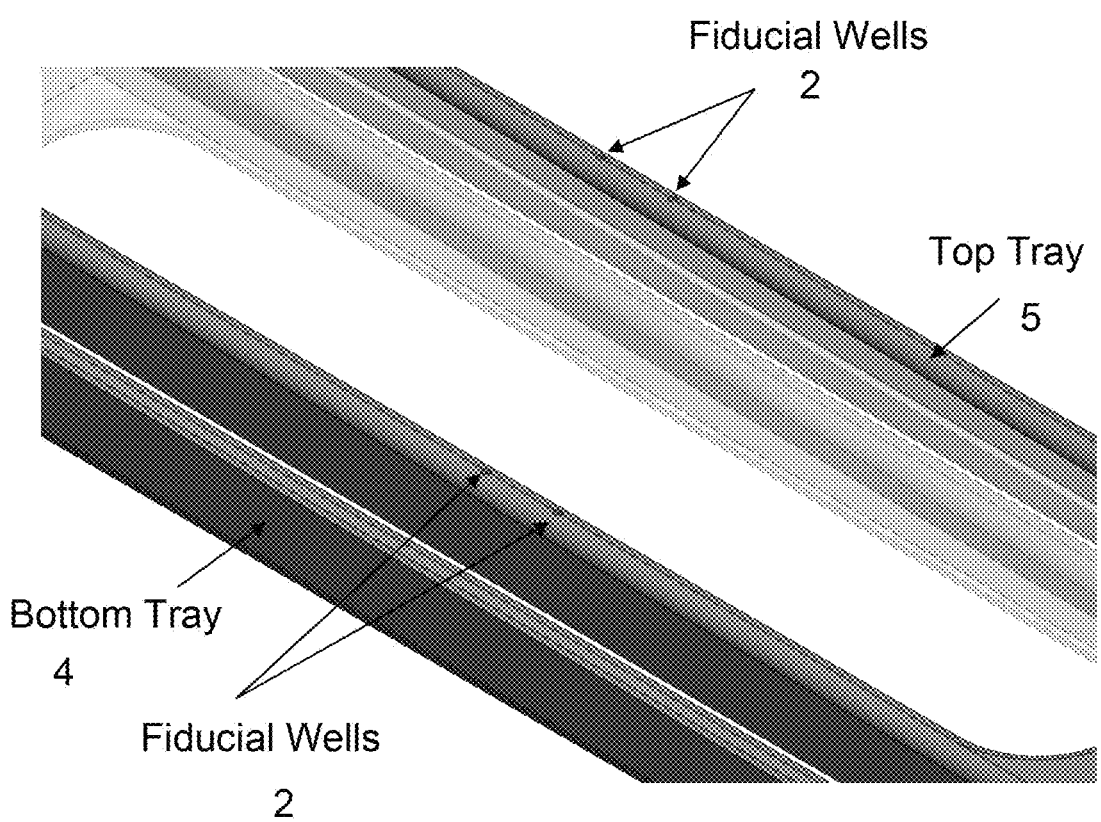
FIG. 10 is a partial isometric view of the animal cassette showing fiducial wells in the Top tray, according to an illustrative embodiment of the invention.
Figure 11:
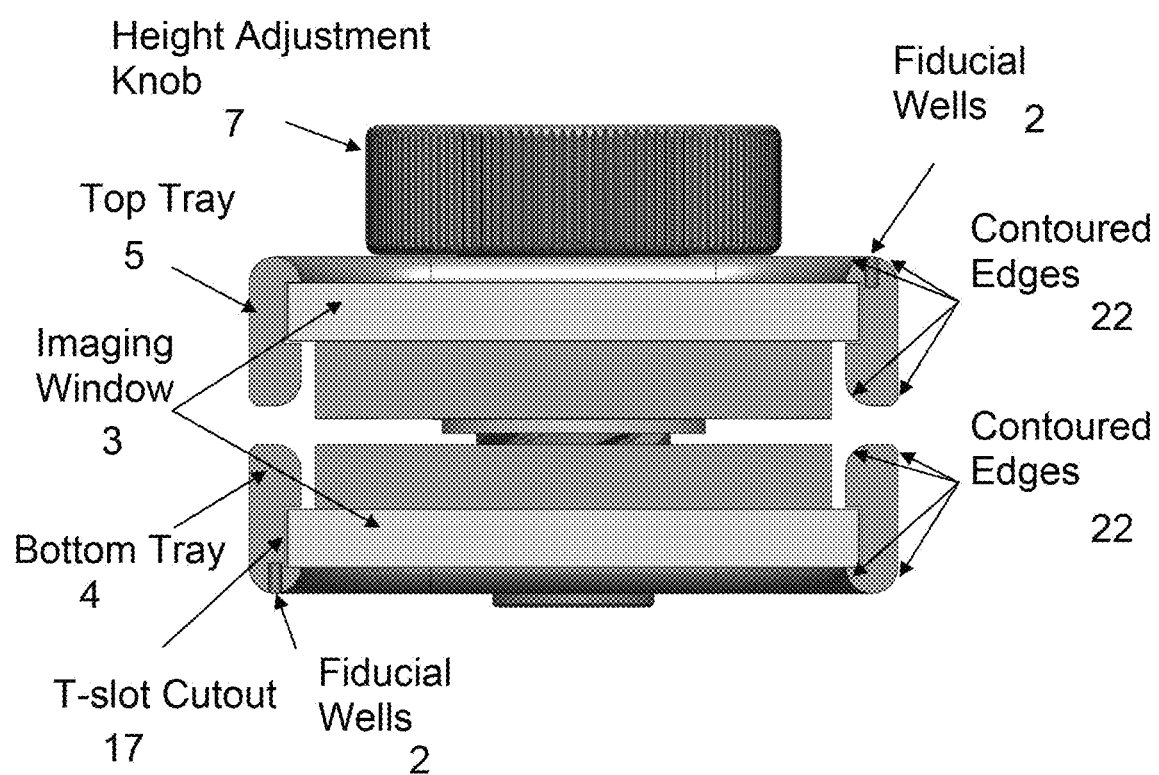
FIG. 11 is an end view of the animal cassette shown in FIG. 1, highlighting contoured edges of the Bottom and Top trays to reduce stray light reflections during imaging, according to an illustrative embodiment of the invention.

Fiducial wells 2 along the top and bottom of both top tray 5 and bottom tray 4 easily allow data fusion between the tomographic imaging modalities (see FIGS. 10, 11). Droplets of fluorescent dye or water can be injected into the fiducial wells 2 for FMT and MR imaging respectively. Similarly, other materials can be used as fiducial markers, including but not limited to organic fluorophores, inorganic fluorophores, indocyanine dyes, quantum dots, visible-wavelength fluorophores, infra-red fluorophores, super-paramagnetic agents, radioactive agents, and others. These materials can be provided in liquid form as droplets within the fiducial wells directly, or as solutions encapsulated in sealed containers inserted into the fiducial wells, for single-use imaging or multi-use imaging. These materials can also be provided in solid form as inserts into the fiducial wells directly, or encapsulated within sealed containers such as radioactive-sealing compartments. CT imaging does not require fluid injections as the fiducial wells can easily be detected due to the differences in density of the tray and fiducial well. A more detailed description of multimodality imaging and data fusion will be described later below. The animal holder can be imaged with the top tray up or with the cassette rotated 180 degrees about the longitudinal axis such that the bottom tray is up. This allows the user to load the animal in any orientation (dorsal or ventral) into the cassette. The animal can be imaged in the cassette dorsally or ventrally as the cassette is can be imaged in any orientation.

FIG. 11 illustrates the contoured edges 22 of top tray 5 and bottom tray 4, which are configured to reduce stray light reflections. As discussed in more detail in connection with FIG. 51, scattered light emanating from the animal preferably is reflected away from the detector to improve imaging. Stray light emanating from the animal or around the animal hit the contoured edges of the animal holder, which are shaped in such a manner as to re-direct the scattered light outside the numerical aperture of the detector. As a result, contoured edges 22 reduce the amount of scattered light that can hit the detector, which as a result, increases the signal-to-noise ratio of the detection technique.

Figure 12:
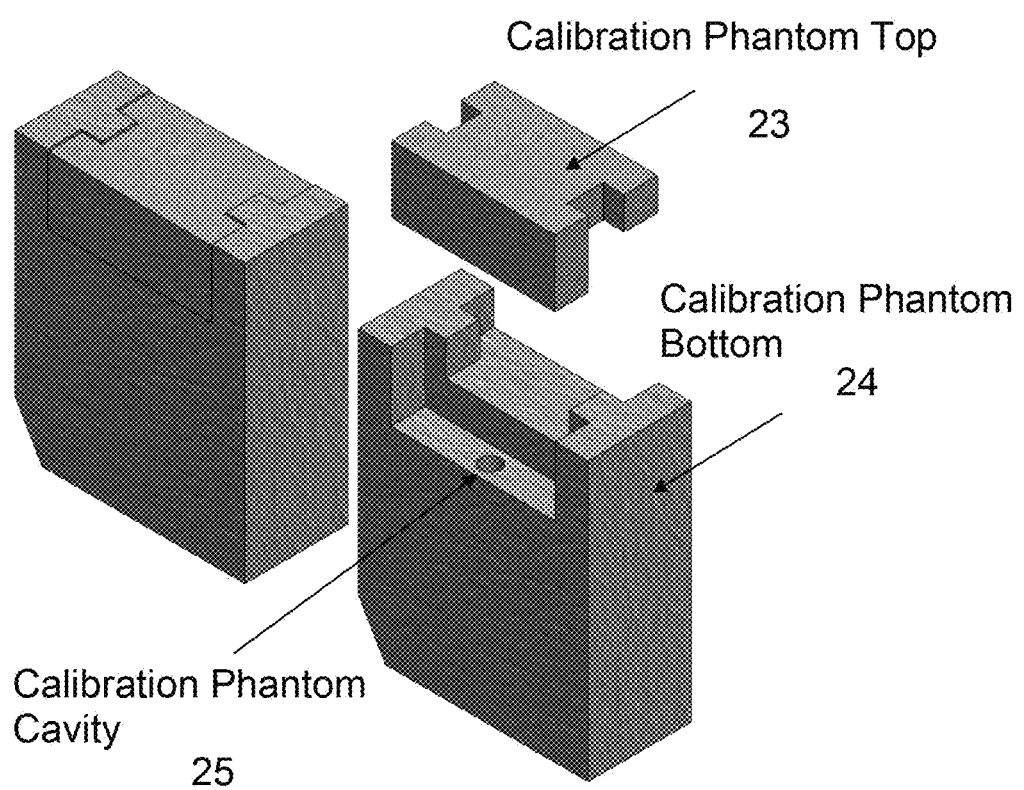
FIG. 12 is an isometric view of a calibration phantom (both top and bottom components shown separately and combined), according to an illustrative embodiment of the invention.
Figure 13:
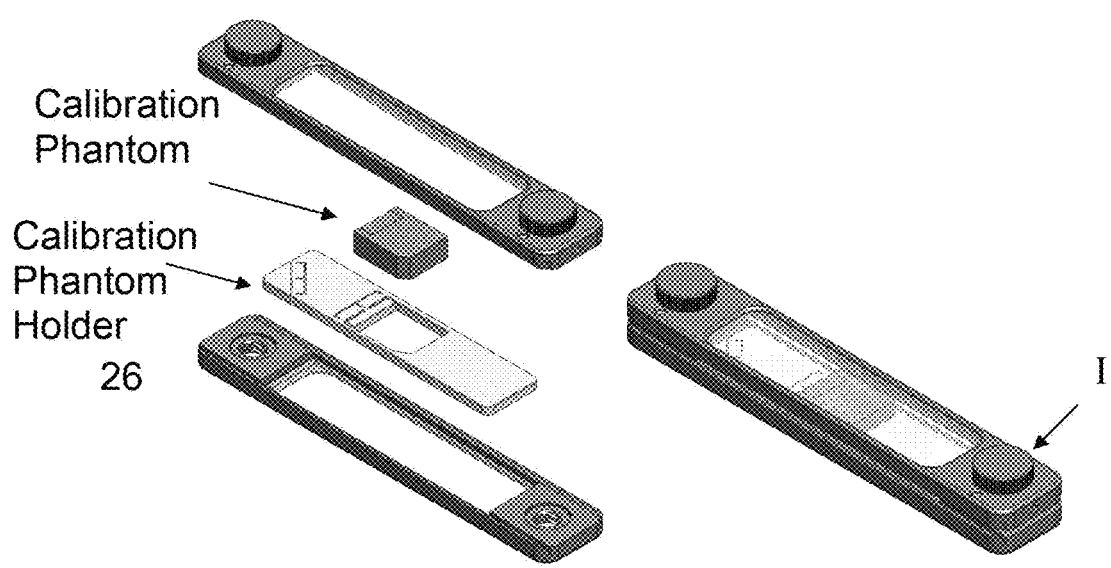
FIG. 13 is an isometric view of the calibration phantom and calibration phantom holder disposed within an exemplary animal holder (exploded and non exploded views), according to an illustrative embodiment of the invention.

FIGS. 12 and 13 illustrate a calibration phantom comprising a calibration phantom top 23 that interfits with a calibration phantom bottom 24 defining calibration phantom cavity 25. The calibration phantom containing the top 23 and bottom 24 can be inserted into a calibration phantom holder 26 that can then be placed within an animal holder I of the invention (see FIG. 13).

Figure 14:
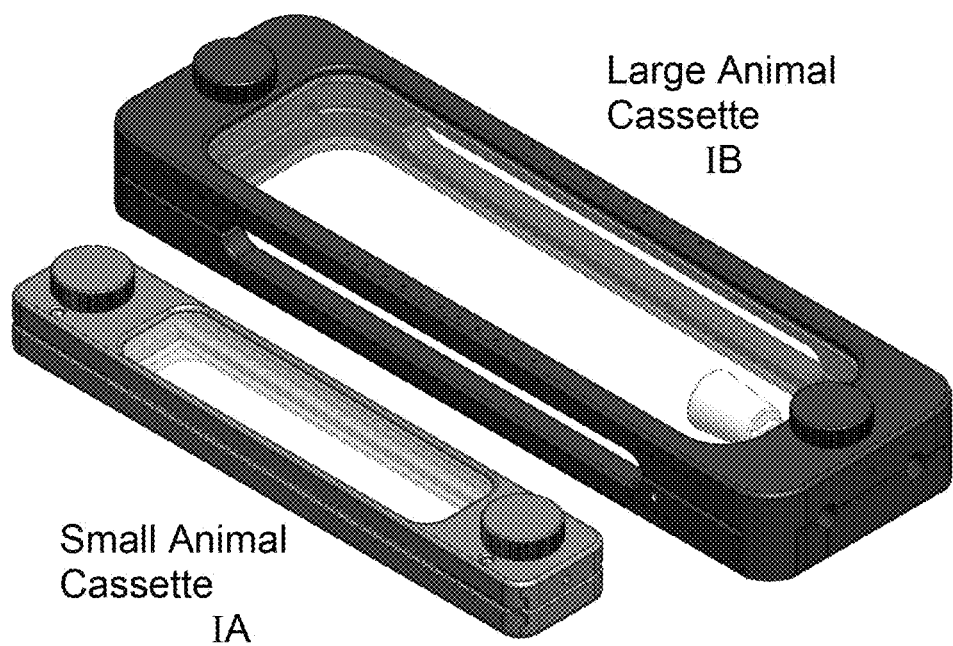
FIG. 14 is a side-by-side comparison between animal cassettes of different sizes, according to an illustrative embodiment of the invention.

FIG. 14 illustrates two different exemplary animal cassettes for small animals of differing sizes. For example, the small animal cassette denoted as IA can be used for smaller rodents, for example, mice, whereas the larger animal cassette denoted as IB can be used to image larger animals, for example, rats, bats and squirrel monkeys.

Figure 15:
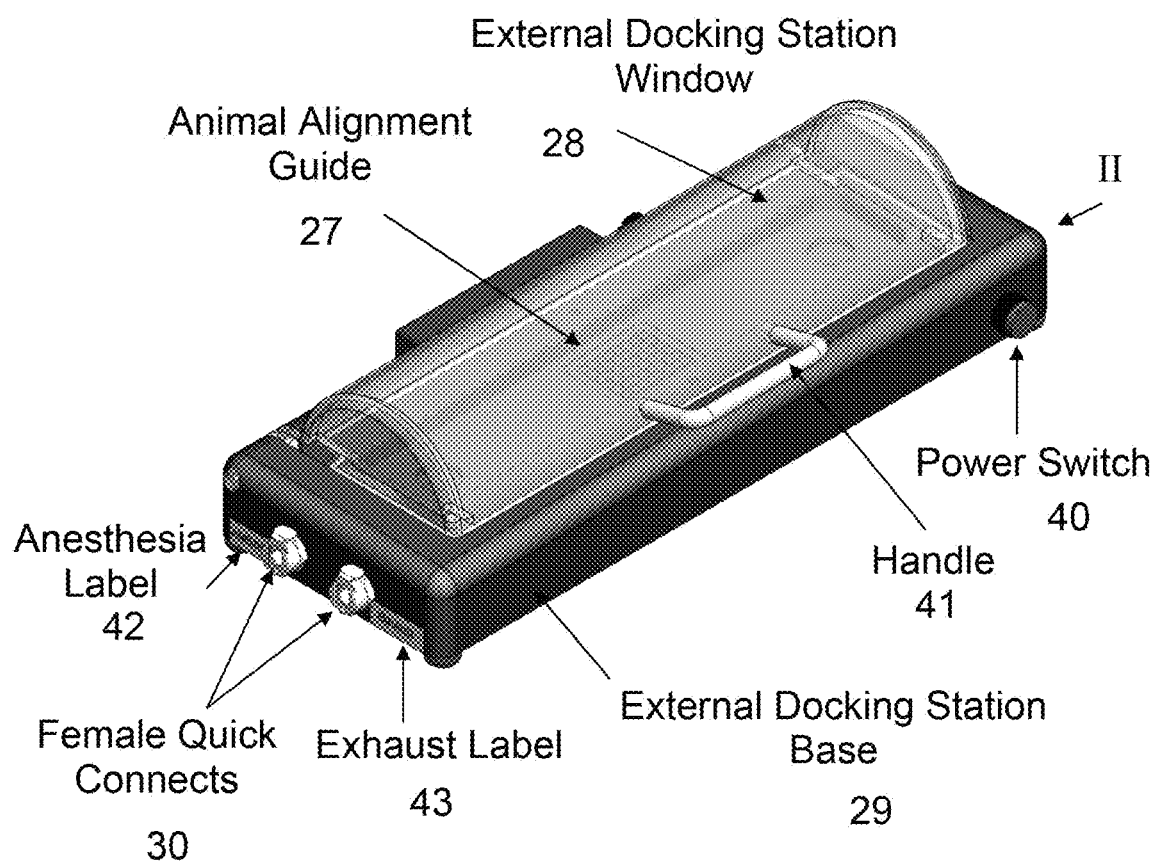
FIG. 15 is an isometric view of an external animal cassette docking station, according to an illustrative embodiment of the invention.
Figure 16:
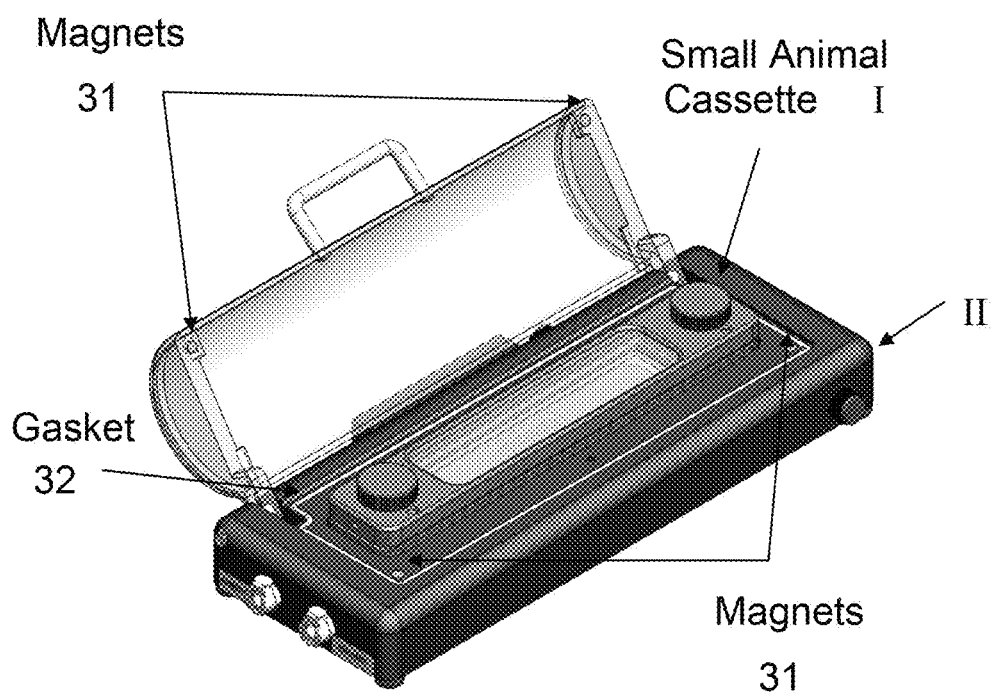
FIG. 16 is an isometric view of an external animal cassette docking station containing an animal cassette disposed therein, according to an illustrative embodiment of the invention.
Figure 17:
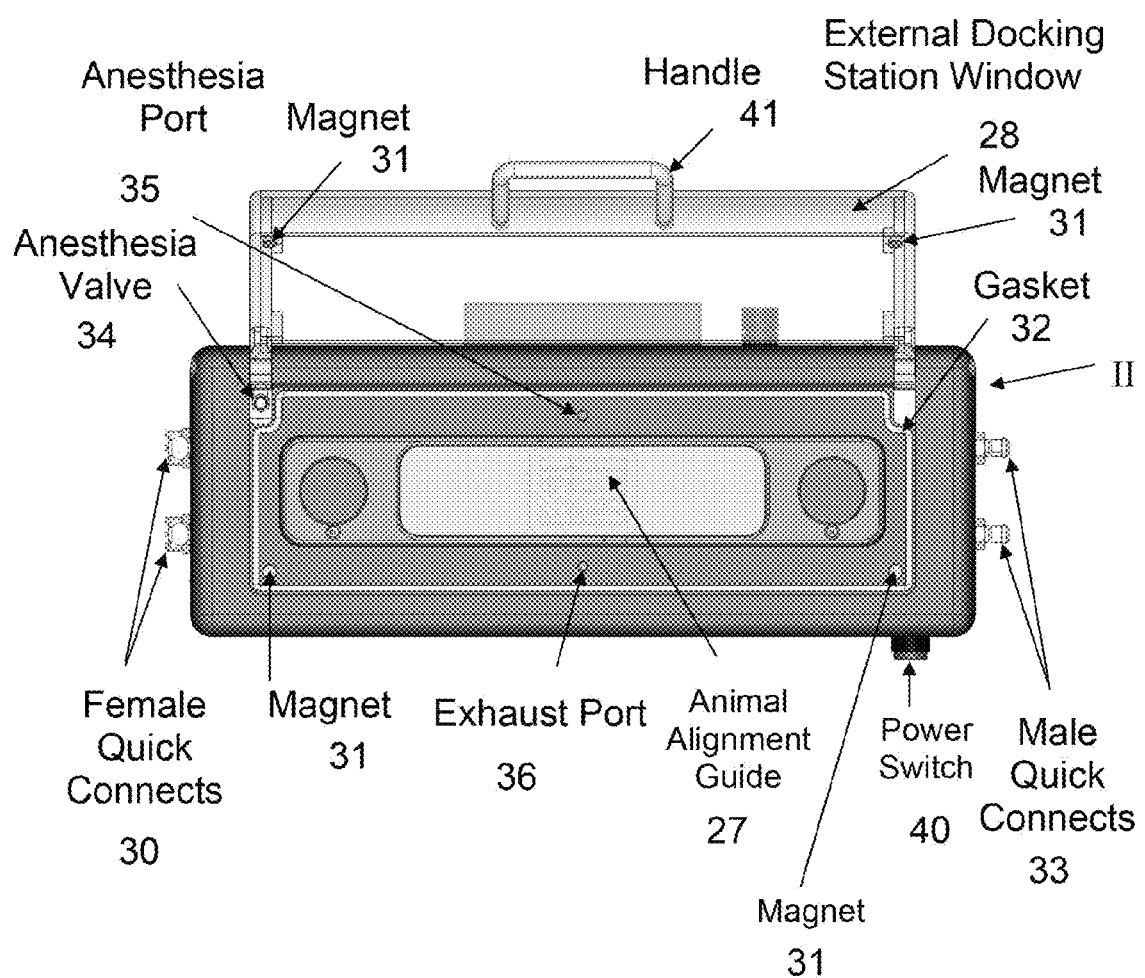
FIG. 17 is a top view of an external animal cassette docking station containing an animal holder disposed therein, according to an illustrative embodiment of the invention.

FIGS. 15-23 and 30-42 illustrate different animal holder mounts that can be inserted into FMT, MR and CT imaging systems. The external docking station denoted as II (as shown in FIGS. 15-19) is used primarily as a holding station for the animal while another animal is being imaged in the tomographic system. The external docking station, for example, as shown in FIG. 15, comprises an external, docking station base 29, an external docking station window 28. Base 29 defines an animal alignment guide 27. Base 29 and window 28 contains magnets 31 affixed thereto that interact with one another to hold the base 29 and window 28 in place, and a gasket 32 provides an air seal (see FIG. 16). The base 29 further comprises female quick connects 30, power switch 40, an anesthesia label 42, and an exhaust label 43. Window 28 further comprises a handle 41 for moving the window 28 relative to base 29. As shown in FIG. 17, the base further comprises an anesthesia valve 34 for introducing anesthesia into the holder via anesthesia part 35. Exhaust port 36 exhausts gas out of the holder.

Figure 18:
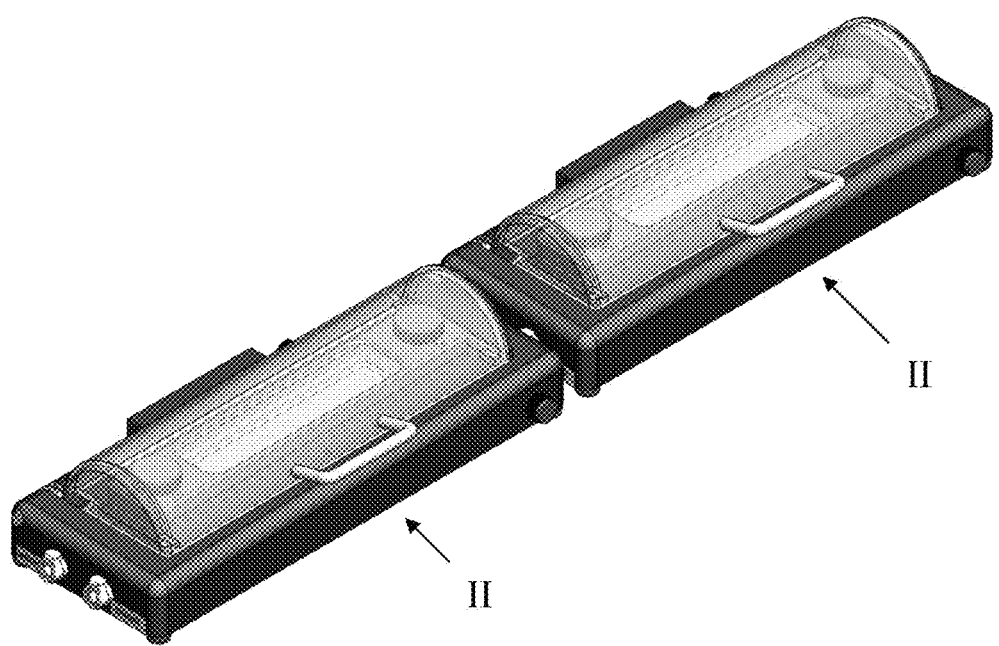
FIG. 18 is an isometric view of two external animal cassette docking stations with gas connections connected in series, according to an illustrative embodiment of the invention.

When in use, the user, for example, places the animal into the holder (FIG. 16), by removing the top tray and places the animal into the holder using the animal alignment guide 27 (FIG. 15, 17) to position the animal within the desired scan region. The user then places the top tray 5 back onto the holder and sets the height adjustment knobs 7 to a known height. Then, the user closes the external docking station window 28 and gas anesthesia is dispensed to keep the animal sedated. FIG. 18 illustrates the serial connection the anesthesia of two or more external docking stations II via quick connects 30 and 33.

Figure 19:
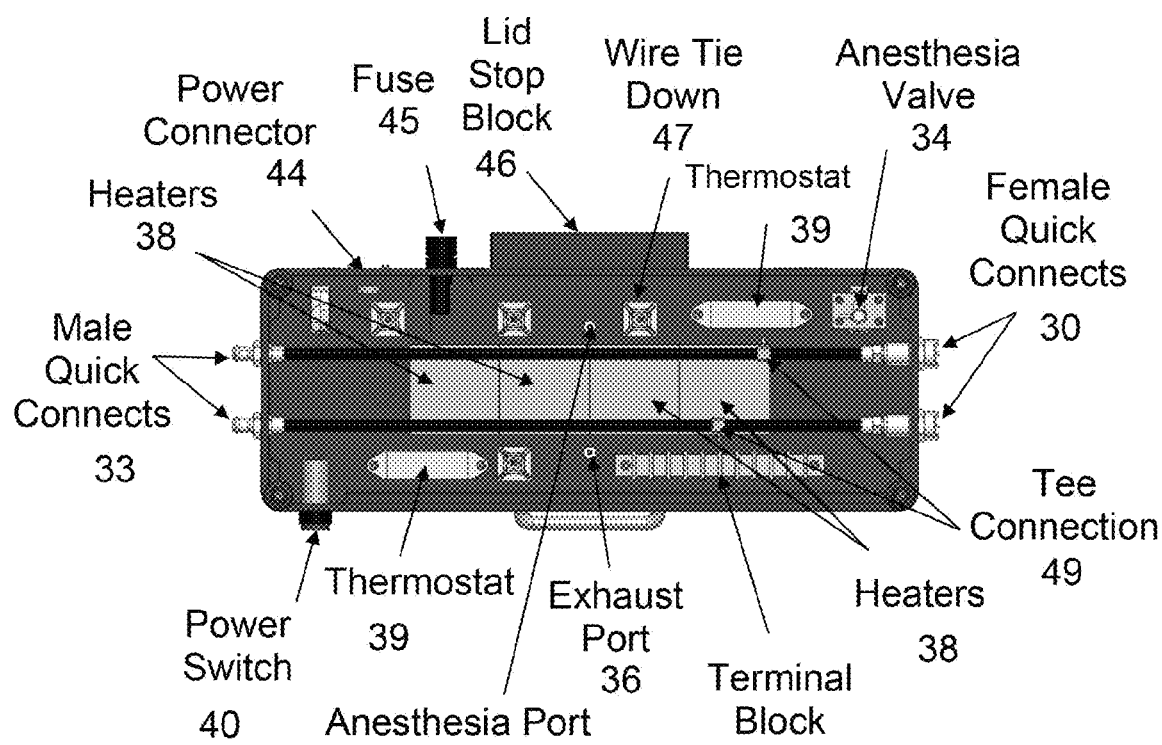
FIG. 19 is a bottom view of an external animal cassette docking station, according to an illustrative embodiment of the invention.

Also, as detailed in FIG. 19, the external docking station is equipped with one or more heaters 38 which can be used to regulate, via thermostats 39, the body temperature of the animal. This can protect the animal from hypothermia, which is possible when the animals are anesthetized. The heaters 38 provided in the docking station can be made of electric resistive heating sheets, such as sheets manufactured by Omega Engineering (Stamford, Conn.) coupled to one or several thermostats regulating the set temperature of the assembly, such as thermostats manufactured by Thermtrol Corporation (North Canton, Ohio). The thermostats can be set to animal body temperature, or 37° C. in the case of most mammals. As shown from underneath, the external docking station contains a power connector 44 and fuse 45. The base also contains a lid stop block 46 for stopping the movement of external docking station window 28. The base also contains wire tie down 47 for securing the wiring and anesthesia tubes (not shown). The associated wiring connects heaters 38 and thermostats 39 to the terminal block 48 and electrical connector 56. The associated tubing connects the anesthesia port 35 and exhaust port 36 to the anesthesia quick connect 62 and exhaust quick connect 63. The conduits contain T connection 49 to route anesthesia gas to anesthesia port 35 and route waste gas from the exhaust port 36 via tubing which is not shown.

Figure 20:
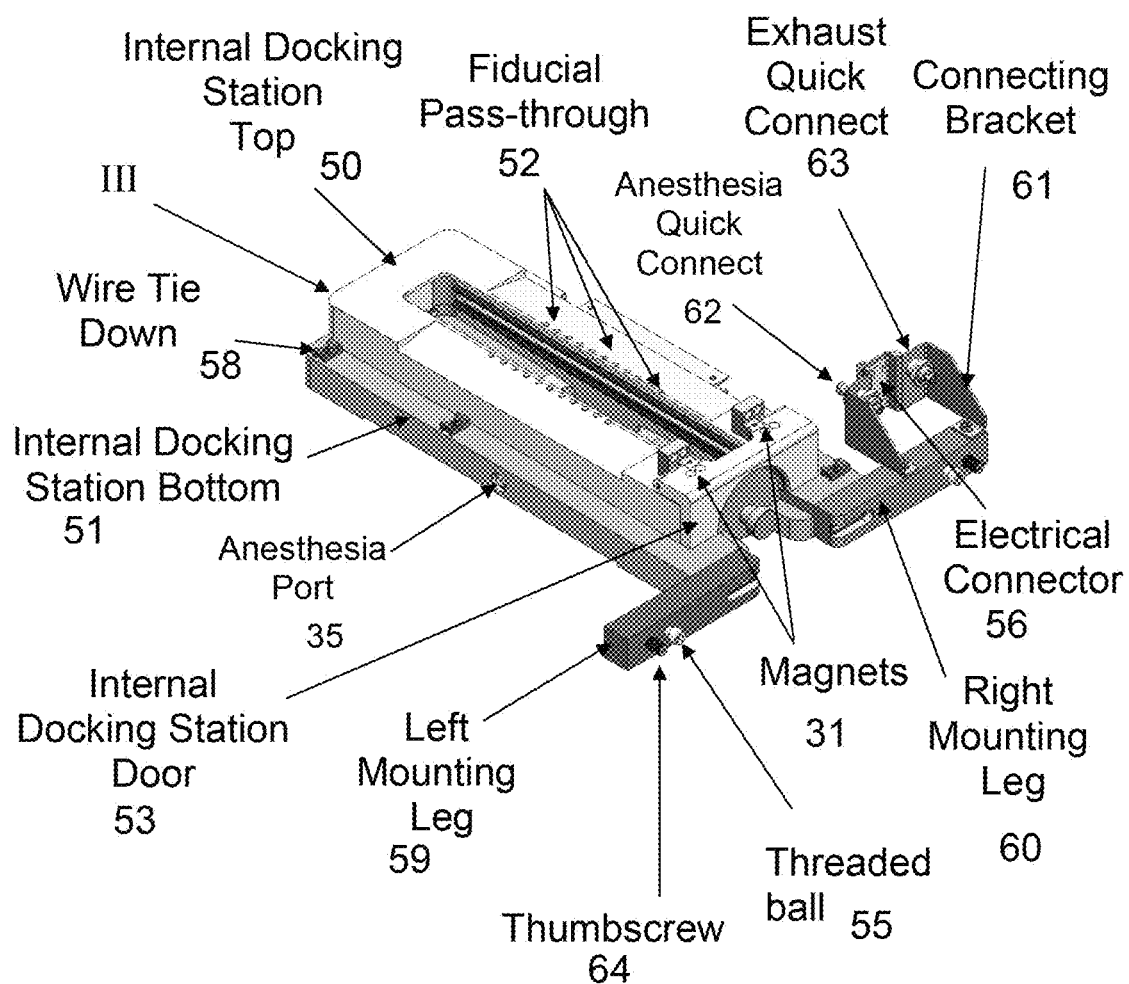
FIG. 20 is an isometric view of an internal animal cassette docking station designed for imaging animals within the FMT system, according to an illustrative embodiment of the invention.
Figure 21:
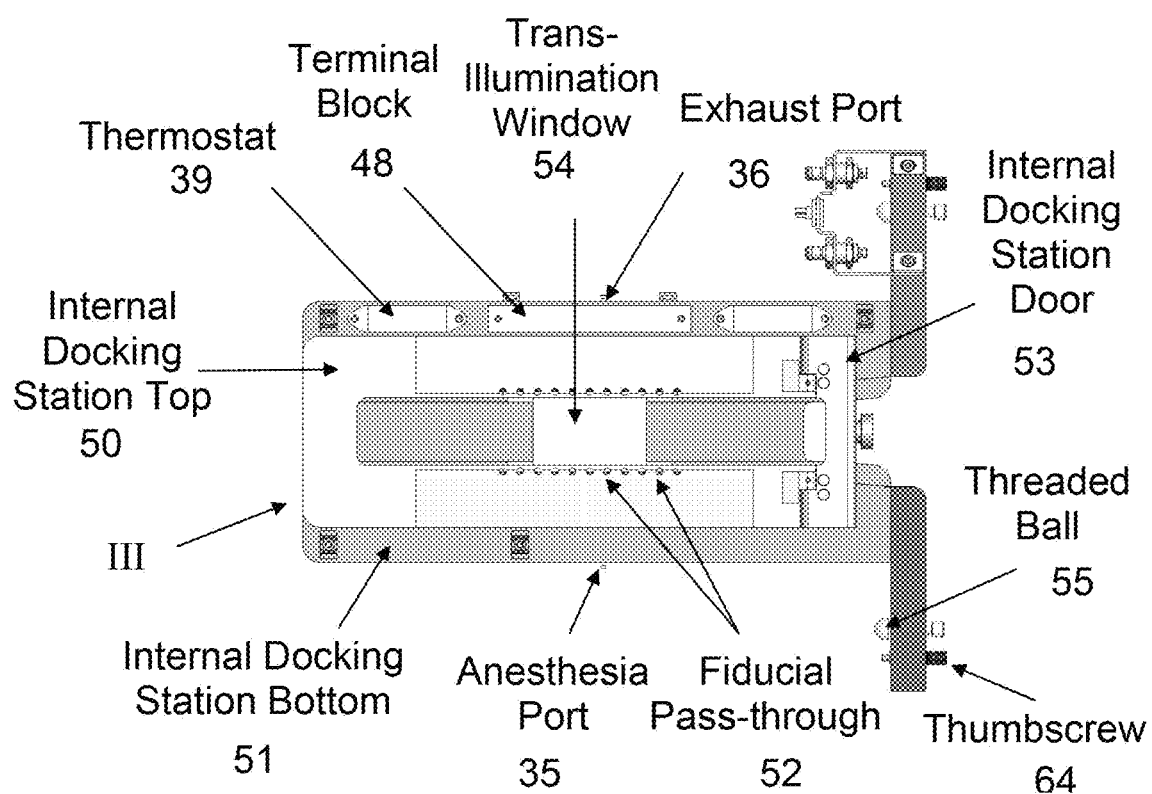
FIG. 21 is a top view of an internal animal cassette docking station designed for imaging animals within the FMT system, according to an illustrative embodiment of the invention.
Figure 22:
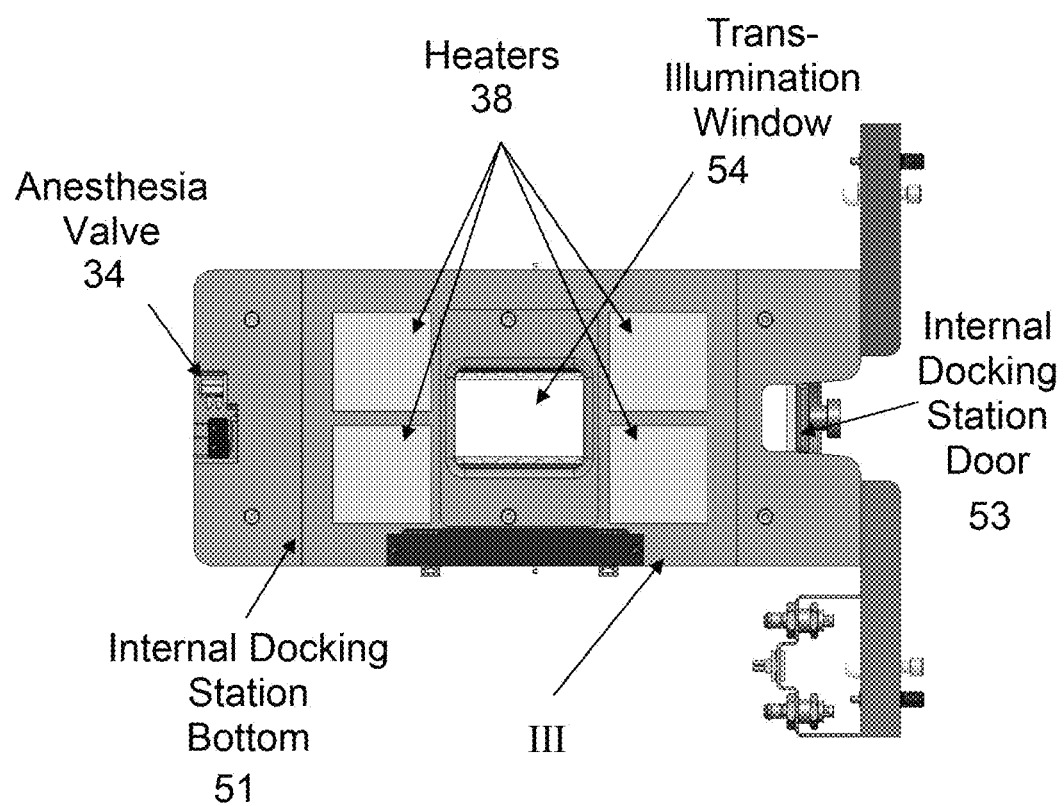
FIG. 22 is a bottom view of an internal animal cassette docking station designed for imaging animals within the FMT system, according to an illustrative embodiment of the invention.
Figure 23:
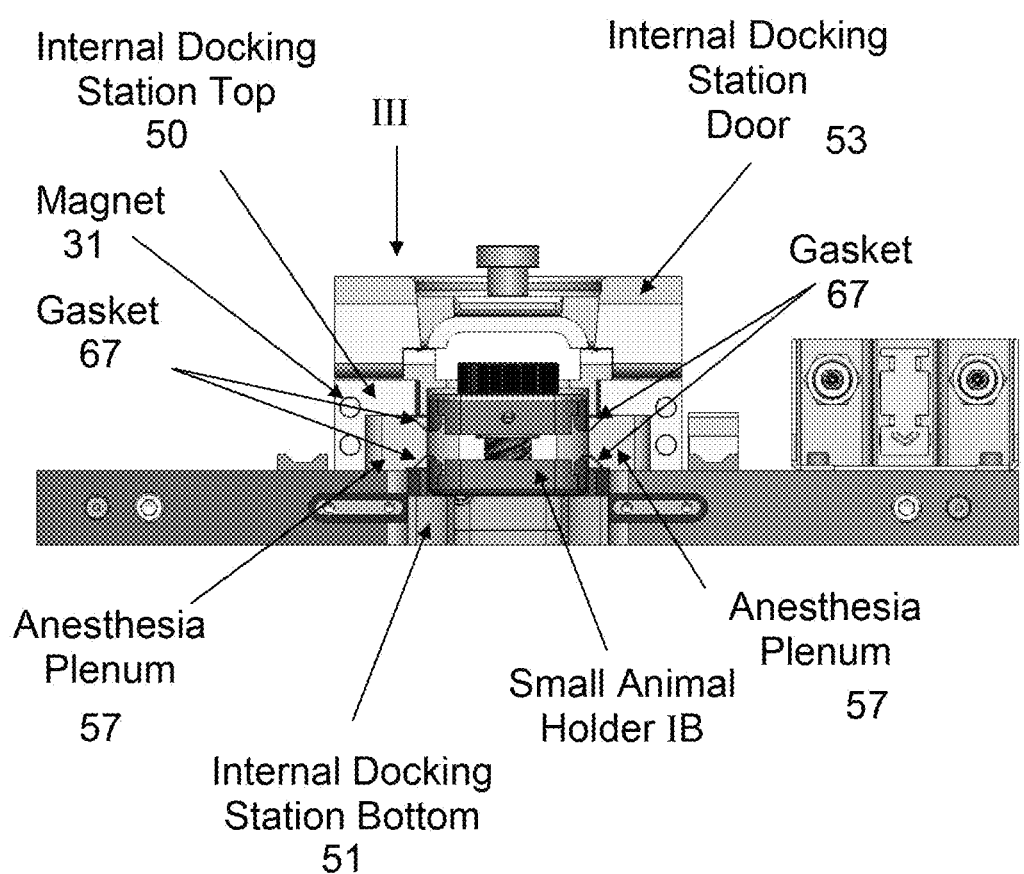
FIG. 23 is an end view of an internal animal cassette docking station designed for imaging animals within the FMT system, according to an illustrative embodiment of the invention.

FIG. 20-23 illustrate an animal holder internal docking station denoted III for imaging an animal in the FMT system. The internal docking station III comprises an internal docking station top 50 that interfits with an internal docking station bottom 51. The top 50 defines fiducial pass-throughs 52. The docking station further comprises an internal docking station door 53. From top view (see FIG. 21), the base docking station comprises a trans-illumination window 54, through which the animal can be exposed to the source of the imaging system for collecting tomographic data. The bottom 51 is connected to a left mounting leg 59 and a right mounting leg 60. Disposed within left mounting leg 59 is threaded ball 55 for adjusting the position of the docking station for alignment and thumbscrew 64 for fixing the docking station into place inside an FMT system. Attached to right mounting leg 60 is connecting bracket 61, anesthesia quick connect 62, exhaust guide connect 63 and electrical connector 56. As shown in FIG. 23, the internal docking station comprises sealing gasket 67 for sealing the small animal holder IA within the internal docking station and anesthesia can be introduced into the small animal holder IA via anesthesia plenum 57. The animal holder IA is placed into the internal docking station III (see FIG. 23) and door 53 is closed. Upon closing the door, gas anesthesia is dispensed into the plenum 57 and vacuum connected to the exhaust port 36 draws the anesthesia across the mouse body (FIG. 23). As shown in FIGS. 20 and 21, fiducial pass-through holes 52 allow reflectance imaging of the fiducial wells 2 defined by the animal holder.

Figure 24:
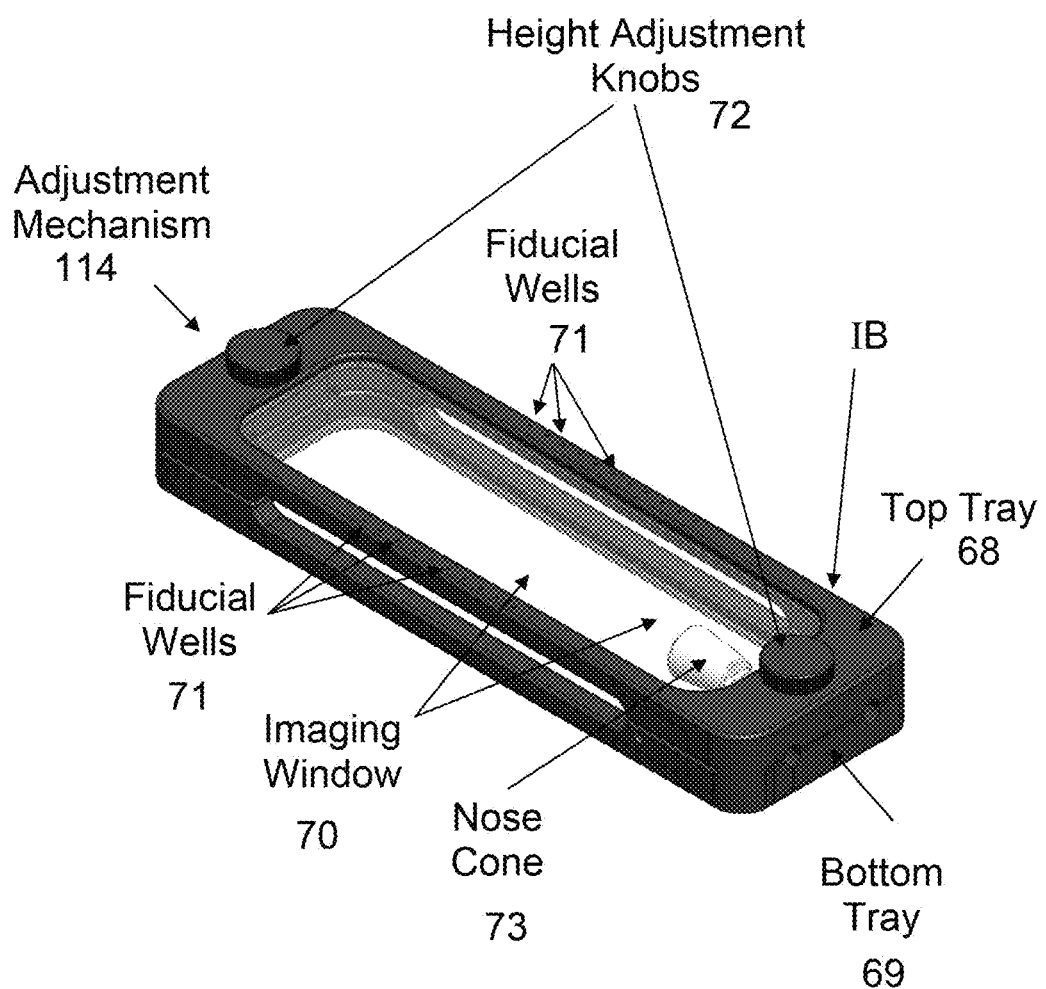
FIG. 24 is an isometric view of an animal cassette, for example, a large animal cassette, for multimodality imaging in accordance with an embodiment of the present invention.
Figure 25:
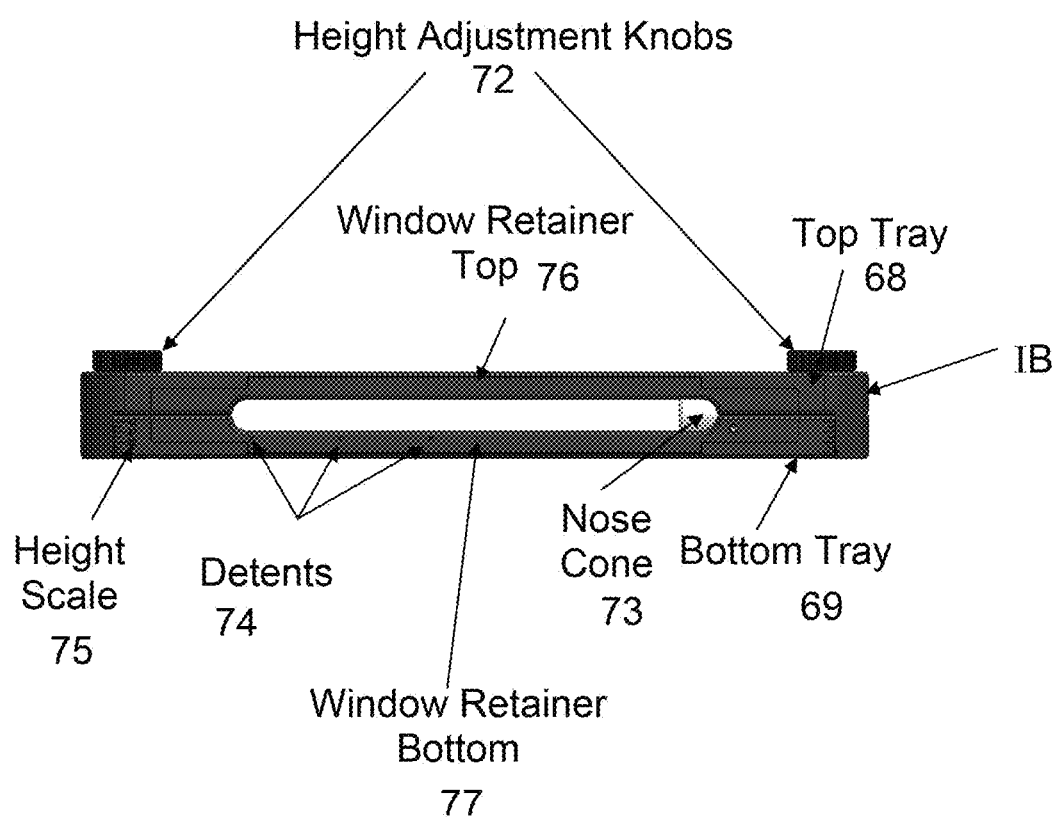
FIG. 25 is a side plan view of the animal cassette shown in FIG. 24, according to an illustrative embodiment of the invention.

FIG. 24-28 illustrate a large animal holder IB for multimodality tomographic imaging. The animal holder, as shown in FIG. 24, comprises a top tray 68 that interfits with bottom tray 69, two imaging windows 70, a plurality of fiducial wells 71, an adjustment mechanism 114 that contains among other things height adjustment knobs 72, and a nose cone 73 for dispensing anesthetic to the animal disposed within the holder. As shown in FIG. 25, top tray 68 defines window retainer top 76 and bottom tray 69 defines a window retained bottom 77. The bottom tray 69 further defines detents 74 that provide a positive stop at three present positions. In an exemplary FMT system, a camera visualizes an area of about 80 mm×80 mm. Detents 74 allow a user to scan the full body of an animal by providing stops that allow the scanned areas to be slightly overlapped.

Figure 26:
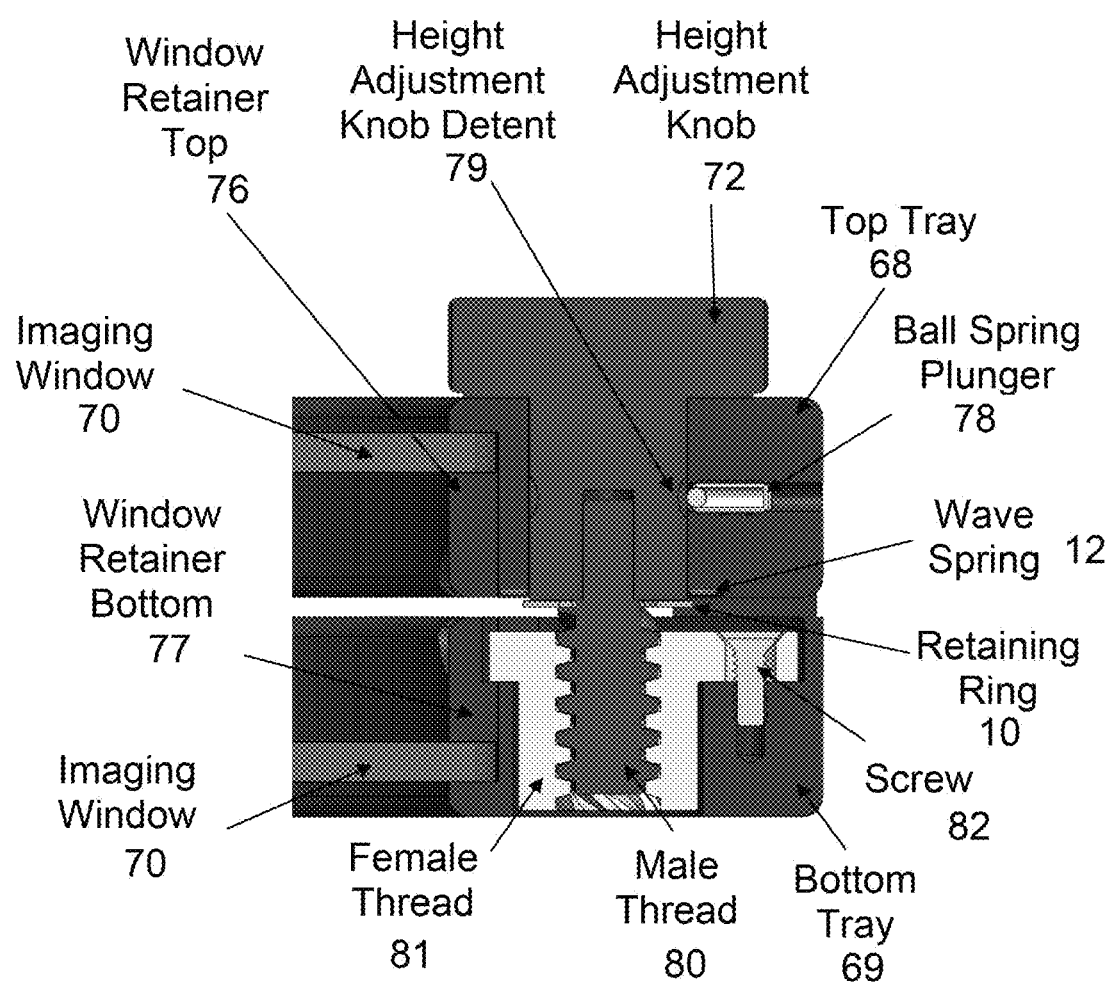
FIG. 26 is a cross-sectional view of the animal cassette shown in FIG. 24, taken at the center of the height adjustment knob along the longitudinal axis, according to an illustrative embodiment of the invention.

Adjustment mechanism 114 repeatably and deterministically sets the separation distance and parallelism of the two imaging windows. The adjustment mechanism 114 in one embodiment, and as shown in FIG. 26, includes height adjustment knobs 72, wave springs 12, retaining rings 10, male thread 80, ball spring plungers 78, female thread 81, screws 82, top window retainer 76, bottom window retainer 77, atop tray 68 and a bottom tray 69. In general, the components with the possible exception of the ball spring plungers 78, male thread 80, and wave springs 12 may be molded, cast, or machined out of plastics, resins, or non-ferrous metals such as Stainless Steel, Aluminum, Titanium or Beryllium Copper. The height adjustment knobs 72, top window retainer 76, bottom window retainer 77, top tray 68 and bottom tray 69 may also be rapid prototyped out of plastics, resins, etc. The imaging windows 70 preferably are translucent for optical FMT imaging, MR imaging, and CT imaging. Although translucent glass is preferred, plastics, resins, and other similar translucent materials can be used to fabricate imaging windows 70.

The height adjustment knobs 72 and male thread 80 allow the user to deterministically and repeatably set the distance between top tray 68 and bottom tray 69 to discrete distances and maintain parallelism. Gentle compression of the specimen between the top tray 68 and bottom tray 69 ensures that the animal does not move during imaging, during transport to the different imaging modalities, and also gives two deterministic boundary conditions for modeling the mouse tissue for quantitative FMT reconstruction. As shown in FIG. 26, ball spring plungers 78 ride into the detents 79 in the side of the height adjustment knobs 72 forcing the height adjustment knobs 72 into repeatable and deterministic angular orientations. The height adjustment knob rotations are converted to linear motion via threads between the male thread 80 and female thread 81; thus setting the distance between top tray 68 and bottom tray 69. The height adjustment knob 72 is secured to top tray 68 by way of a wave spring 12 and a retaining ring 10 (see FIG. 26).

In one embodiment, as shown in FIG. 25, a height scale 75 allows the user to determine the distance between top tray 68 and bottom tray 69. Setting both adjustment knobs to the same height ensures that the imaging windows 70 are parallel and separated by a known distance and are held to strict tolerances.

The female thread 81 is secured to the bottom tray 69 via screws 82 (see FIG. 26). Imaging windows 70 made of, for example, glass or translucent plastic, allow tomographic imaging of the specimen within the animal holder. The windows are secured to top tray 68 and bottom tray 69 with top window retainer 76 and bottom window retainer 77.

Figure 27:
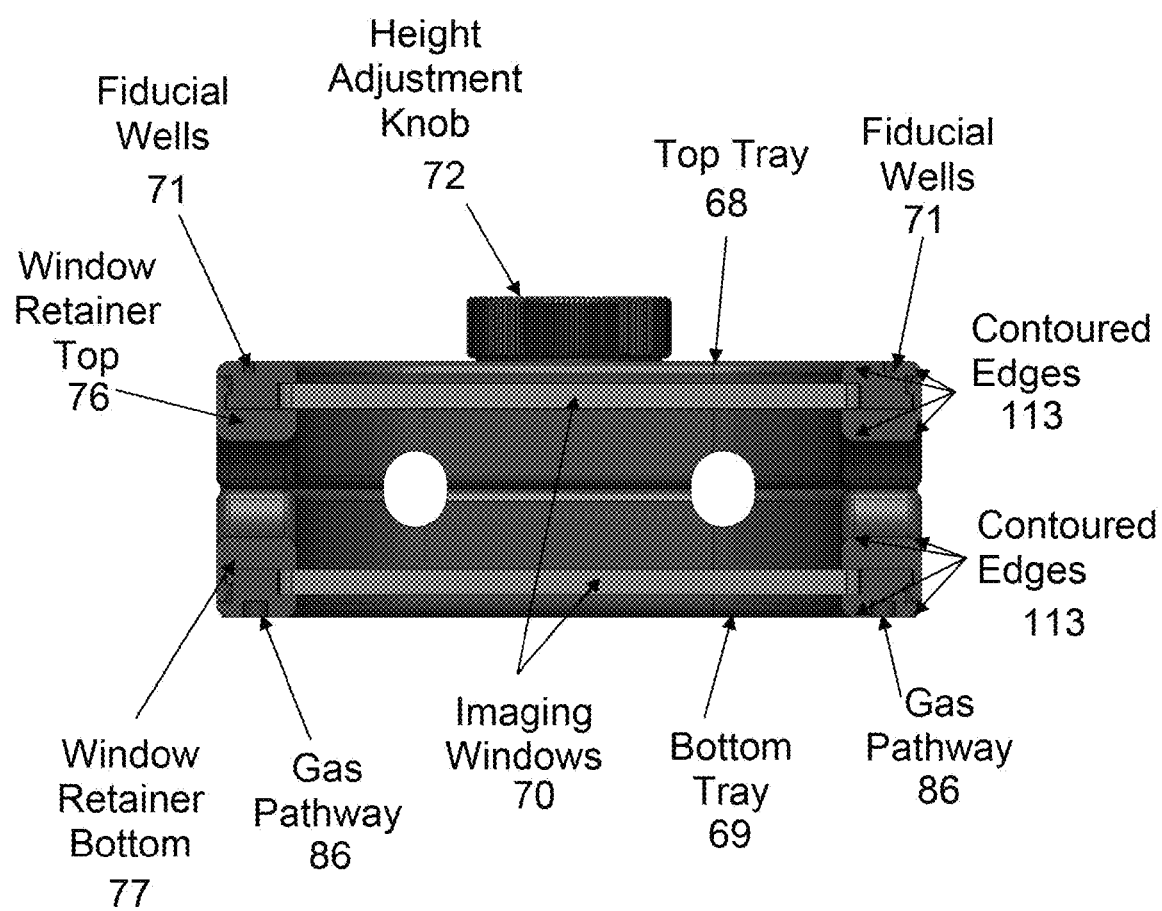
FIG. 27 is a cross-sectional view of the animal cassette shown in FIG. 24, taken at the center of the animal cassette along the transverse axis, according to an illustrative embodiment of the invention.

Fiducial wells 71 along the top of top tray 68 allow data fusion between the tomographic imaging modalities (see FIGS. 24 and 27). Droplets of fluorescent dye or water can be injected into the fiducial wells 71 for FMT and MR imaging, respectively. Similarly, other materials can be used as fiducial markers, including but not limited to organic fluorophores, inorganic fluorophores, indocyanine dyes, quantum dots, visible-wavelength fluorophores, infra-red fluorophores, superparamagnetic agents, radioactive agents, and others. These materials can be provided in liquid form as droplets within the fiducial wells directly, or as solutions encapsulated in sealed containers inserted into the fiducial wells, for single-use imaging or multi-use imaging. These materials can also be provided in solid form as inserts into the fiducial wells directly, or encapsulated within sealed containers such as radioactive-sealing compartments. CT imaging does not require fluid injections as the fiducial wells can easily be detected due to the differences in density of the tray and fiducial well. A more detailed description of multimodality imaging and data fusion is described below. The animal holder can be imaged with the top tray up or with the cassette rotated 180 degrees about the longitudinal axis such that the bottom tray is up. This allows the user to load the animal in any orientation (dorsal or ventral) into the cassette. The animal can be imaged in the cassette dorsally or ventrally as the cassette is can be imaged in any orientation.

FIG. 27 illustrates contoured edges 113 of the top tray 68, bottom tray 69, top window retainer 76, and bottom window retainer 77 to reduce stray light reflections into the numerical aperture (NA) of the imaging device during reflectance and tomographic imaging. The contoured edges are shaped to re-direct the reflected light outside the numerical aperture of the objective lens or other optical device placed in front of the detector. As the reflected and re-directed stray light falls outside the numerical aperture or acceptance cone of the detector optics, such stray light will have no (or very limited) disruptive impact on the detection of useful signal, which enhances the signal-to-noise ratio of the detection technique. FIG. 27 also shows gas pathway 86 through which anesthesia can be introduced into the holder.

Figure 28:
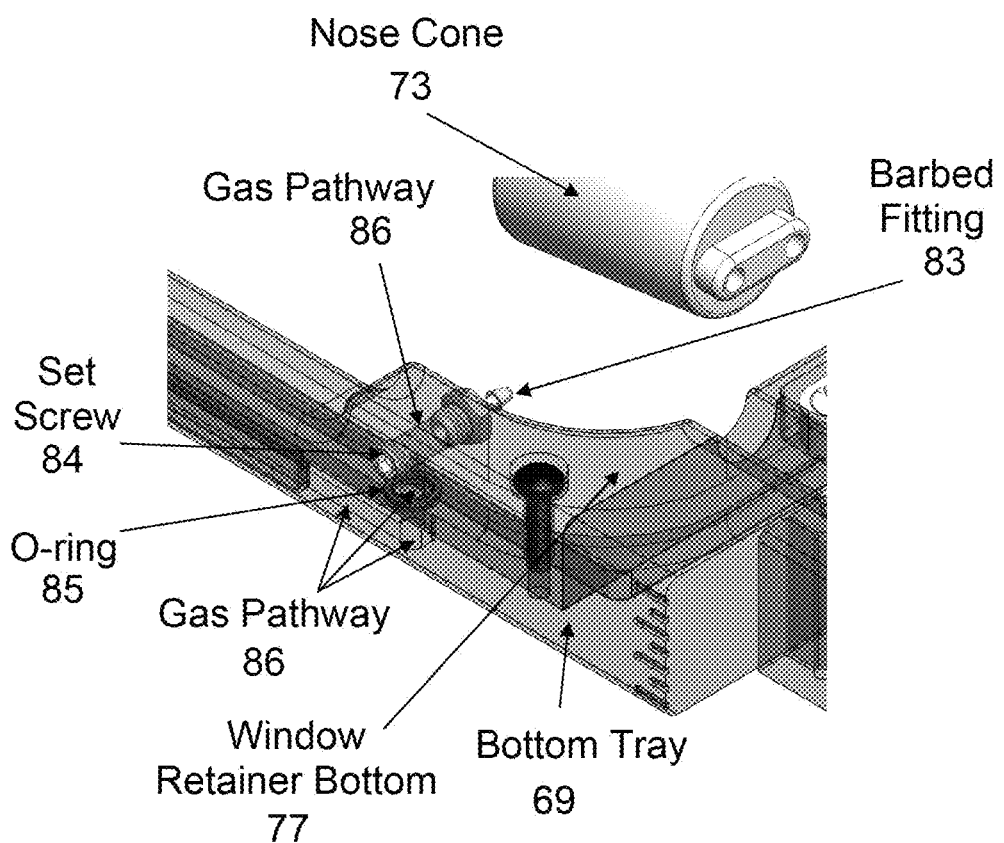
FIG. 28 is a partial isometric view of a large animal cassette embodiment allowing for direct connection of gas anesthesia administered through the gas pathway to the animal nose cone, according to an illustrative embodiment of the invention.

FIG. 28 illustrates one approach for sedating a large animal via direct connection of gas anesthesia and vacuum to the animal holder. The gas anesthesia is passed through the holder via gas pathway 86 and into flexible tubing (not shown) attached at one end to barbed fitting 83 and attached at the other end to the animal nose cone 73. The barbed fitting 83 is immobilized in bottom tray 64 by means of set screw 84 and O-ring 85. The nose cone 73 is placed adjacent the animal's head and allows gas anesthesia scavenging through the vacuum line connection. Inhalation or gas anesthesia, such as isoflurane- or halothane-based anesthesia is a common and sometimes preferred anesthesia technique in animal-handling environments. An inhalation anesthesia delivery system, such as products offered by LEI Medical (Boring, Oreg.), administers a mixture of the anesthetic gas (for example, isoflurane) with pure oxygen. The animal usually is sedated in a sealed induction-chamber. When ready to be imaged, the anesthetized animal is retrieved from the sealed induction-chamber and placed in the imaging instrument, for example, in the animal holder described herein.

As illustrated in FIG. 28, inhalation anesthesia can be delivered in order to maintain the animal in its sedated state during imaging. In certain embodiments, such as in the case of small animal imaging, a nose cone may not be necessary for gas anesthesia delivery and the animal may receive anesthesia directly within a gas-flooded chamber. In certain embodiments, an animal respiration monitor is used to coordinate optimal image recording conditions with the animal's physical state. For example, a pressure transducer can allow respiratory gating whereby the imaging device is triggered to take images only during a particular phase of the respiratory cycle, minimizing motion artifacts.

Figure 29:
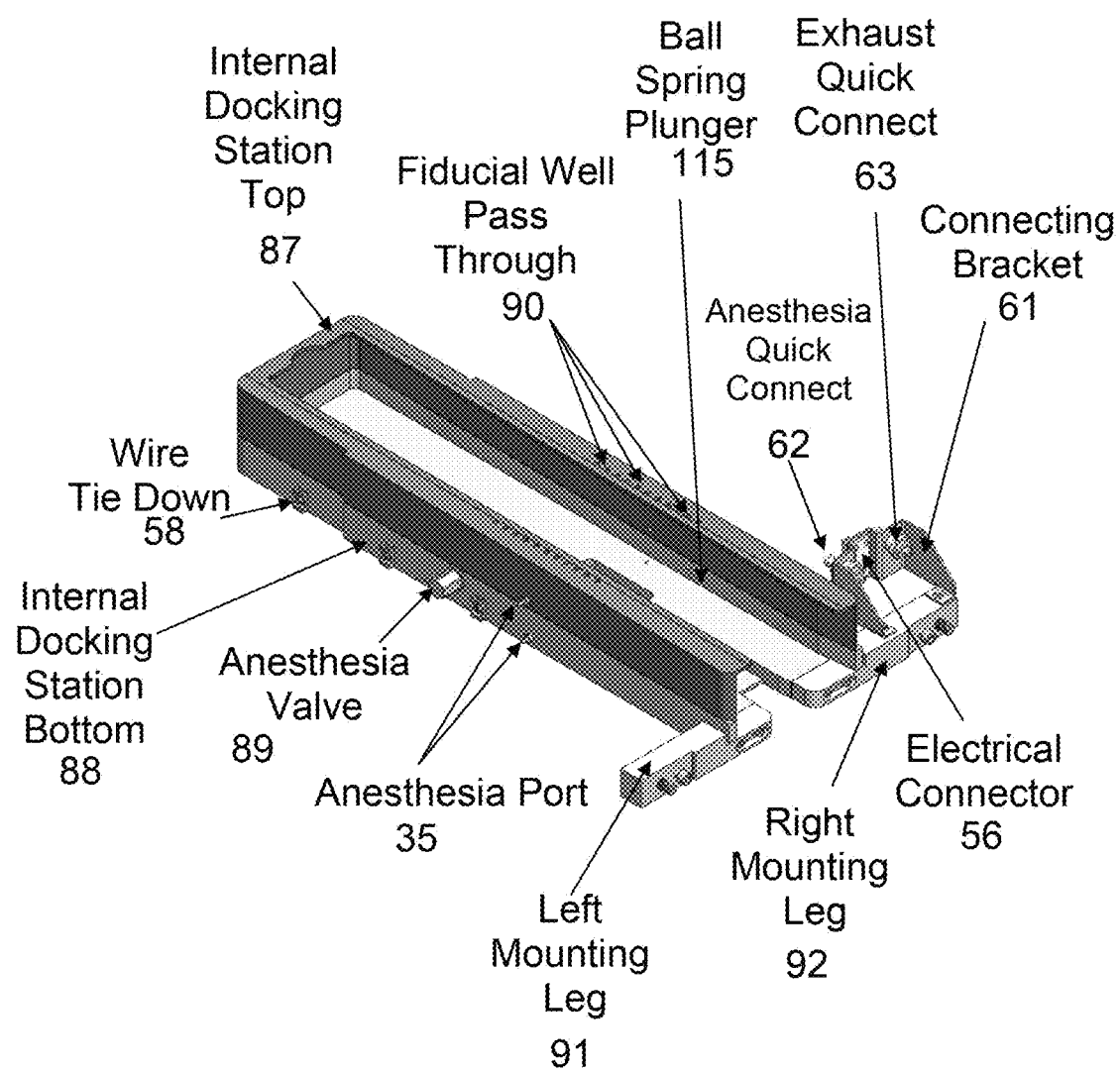
FIG. 29 is an isometric view of an internal animal cassette docking station designed for imaging animals within the FMT system, according to an illustrative embodiment of the invention.
Figure 30:
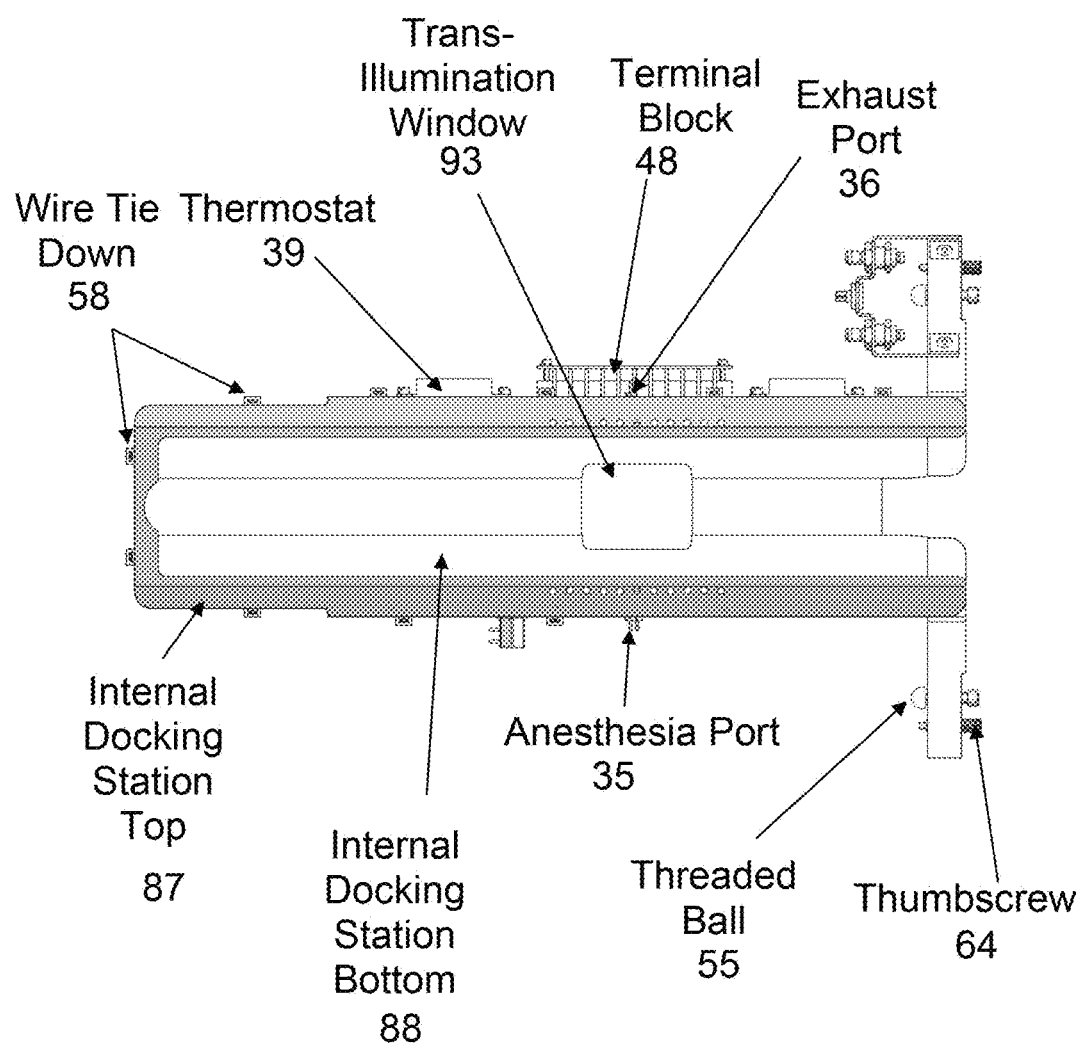
FIG. 30 is a top view of an internal animal cassette docking station designed for imaging animals within the FMT system, according to an illustrative embodiment of the invention.
Figure 31:
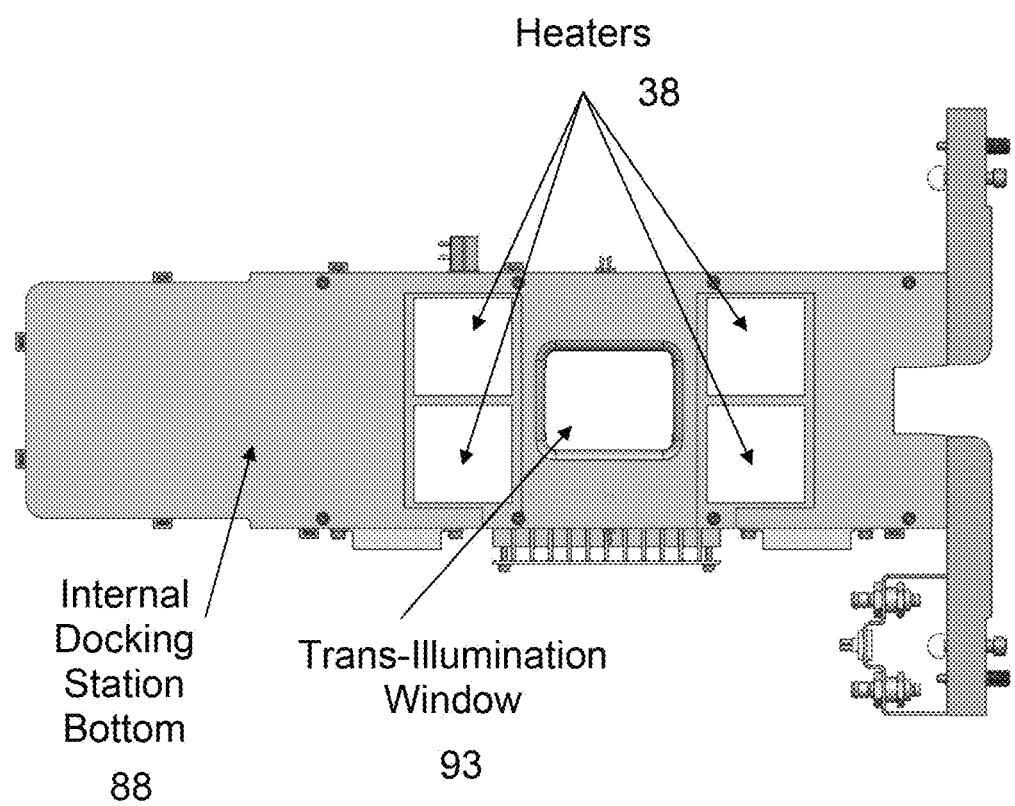
FIG. 31 is a bottom view of an internal animal cassette docking station designed for imaging animals within the FMT system, according to an illustrative embodiment of the invention.

FIGS. 29-33 illustrate an animal holder internal docking station for imaging an animal in the FMT system. As shown in FIGS. 29-31, the animal holder docking station comprises an internal docking station top 87 that interfits with docking station bottom 88. The docking station bottom 88 is coupled to left mounting leg 91 and right mounting leg 92. Ball spring plungers 115 (see FIG. 29) engage detents 74 of the animal holder (see FIG. 25). The plungers connect to the detents to hold the animal holder in position. The whole bodies of large animals such as rats can be scanned by changing the position of the holder within the docking station. The detents mark an animals position for consistent imaging. Wire tie downs 58 (see FIGS. 20, 29 and 30) serve to secure the wiring and anesthesia tubing (not shown), which are part of the internal docking stations. The associated wiring connects heaters 38 and thermostats 39 to the terminal block 48 and electrical connector 56. The associated tubing connects the anesthesia port 35 and exhaust port 36 to the anesthesia quick connect 62 and exhaust quick connect 63, respectively.

Figure 32:
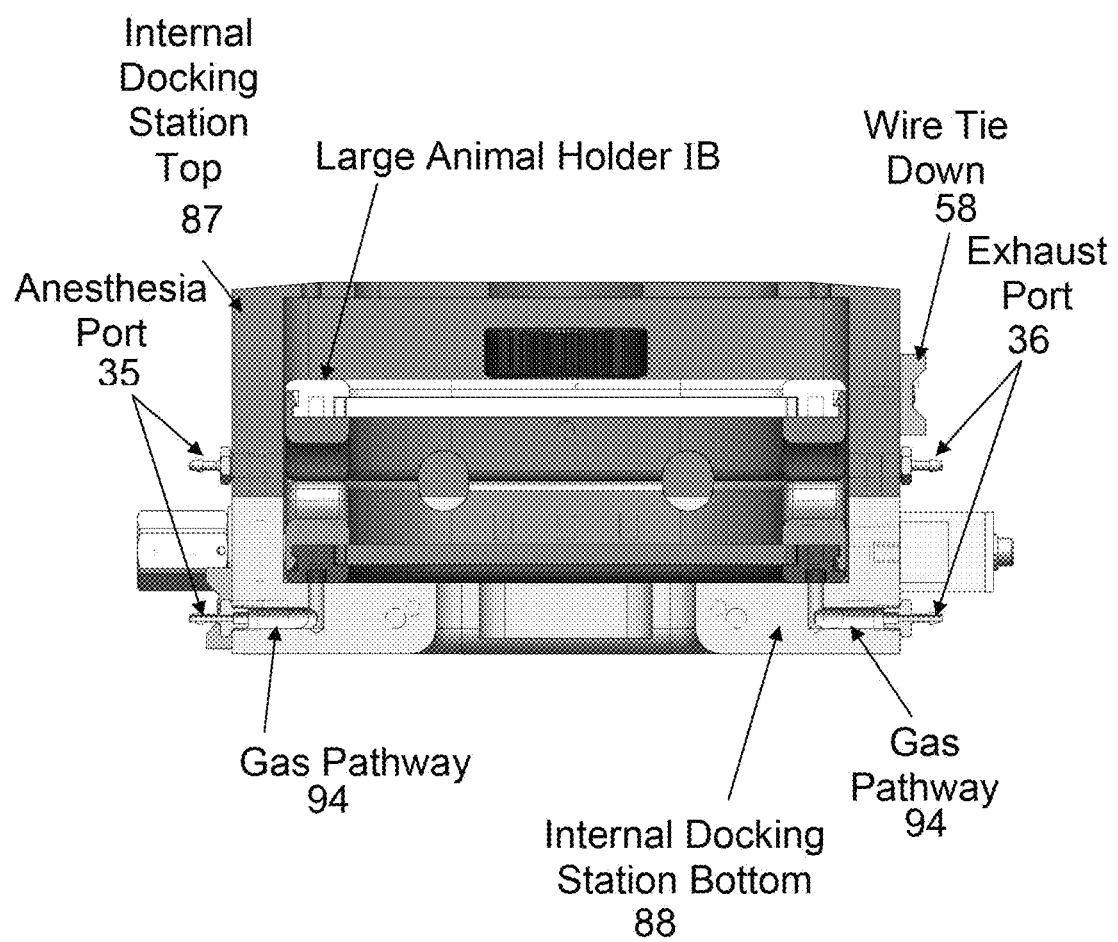
FIG. 32 is an end view of an internal animal cassette docking station designed for imaging animals within the FMT system, according to an illustrative embodiment of the invention.
Figure 33:
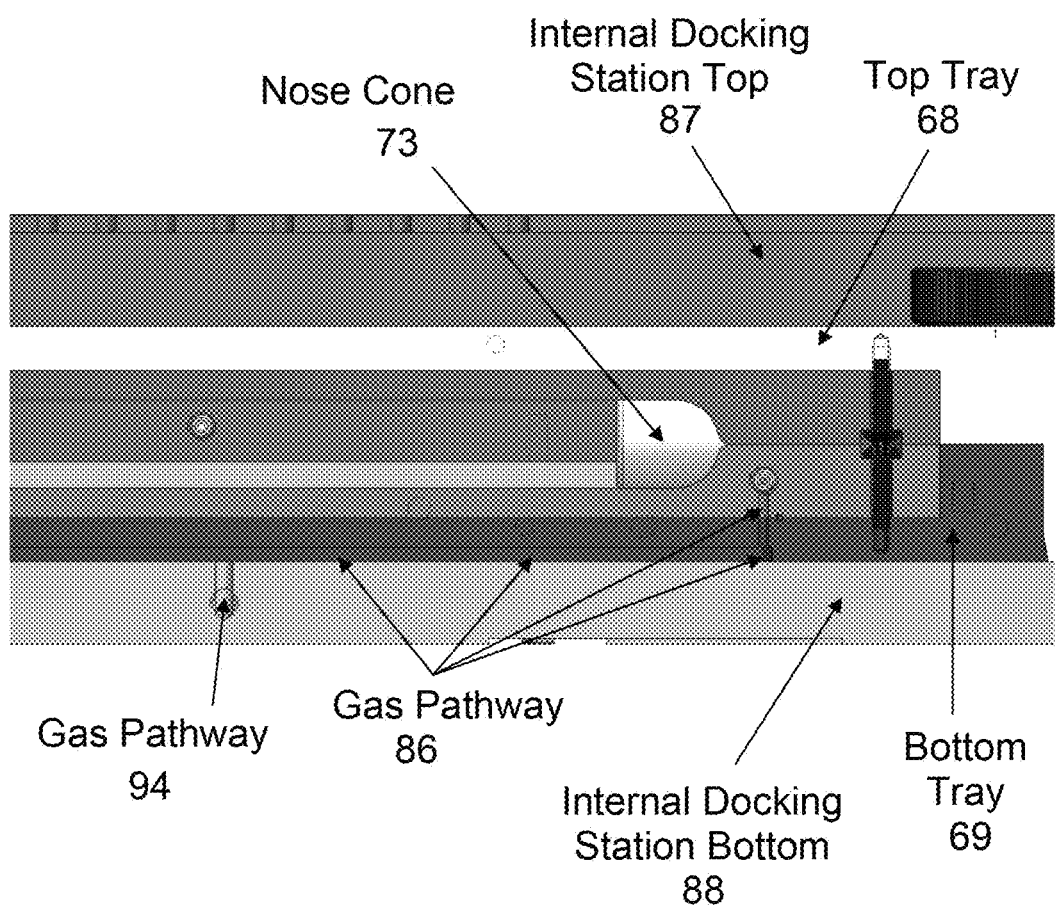
FIG. 33 is a partial cross-sectional view of an internal large animal cassette docking station gas pathway taken along the longitudinal axis, according to an illustrative embodiment of the invention.

Docking station top 87 defines a plurality of fiducial well pass through holes 90, to allow reflectance imaging of the fiducial wells 71 defined by the animal holder. The anesthesia can be controlled by anesthesia valve 89. The docking station comprises a trans-illumination window 93, which permits imaging of the animal. FIG. 32 shows that the docking station comprises gas pathway 94 for introducing gas, for example, anesthesia, into and out of the animal holder IB. The animal holder is placed into the internal docking station (FIG. 32). Upon insertion, gas anesthesia is dispensed into the animal holder and vacuum connected to the exhaust port 36 draws the anesthesia across the mouse body (FIG. 32).

Figure 34:
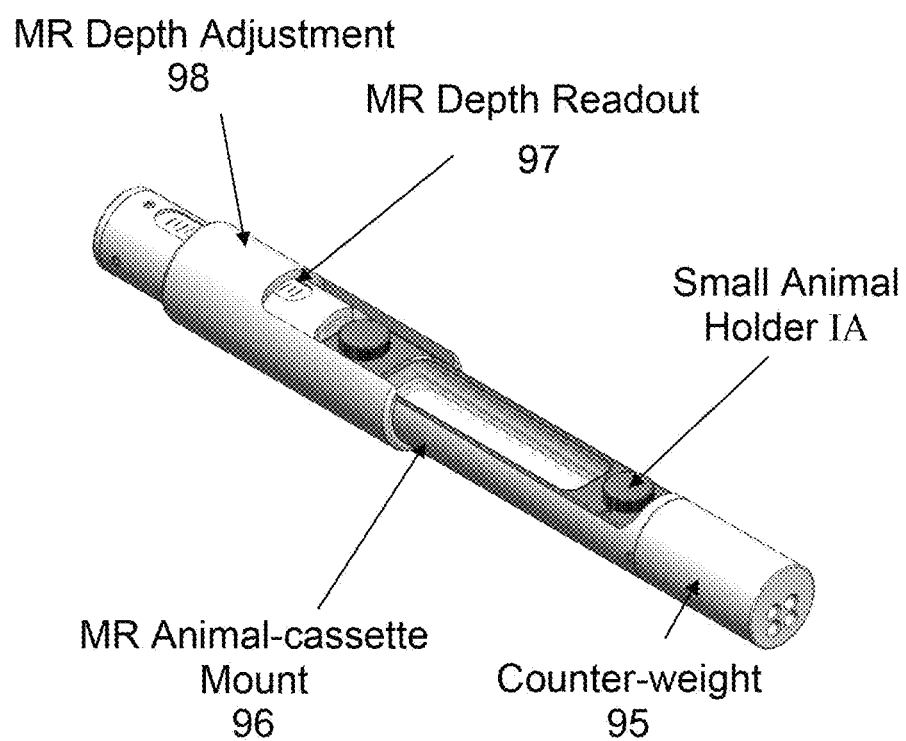
FIG. 34 is an isometric view of an internal animal cassette docking station designed for imaging animals within an MR system, according to an illustrative embodiment of the invention.
Figure 35:
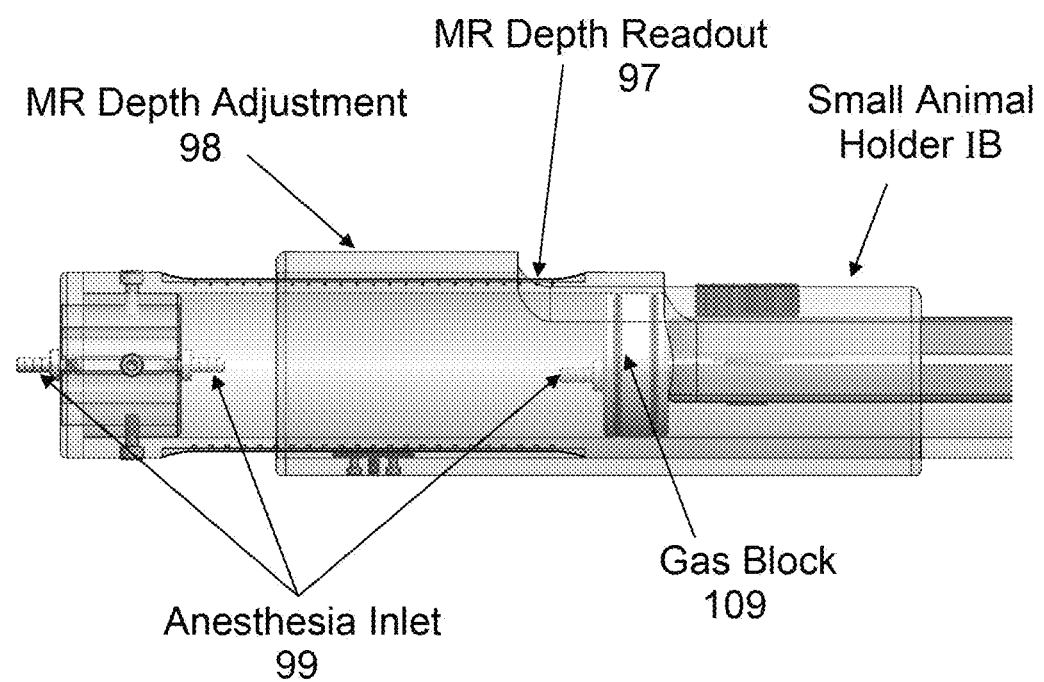
FIG. 35 is a partial side view of an internal animal cassette docking station designed for imaging animals within an MR system detailing the gas anesthesia connections and MR depth adjustment, according to an illustrative embodiment of the invention.

FIGS. 34-35 illustrate an animal holder docking station for imaging an animal in an MR system. The animal holder IA is placed into a slot defined by the docking station (see FIG. 34). The docking station comprises an MR animal holder mount 96 which defines a cavity for receiving the animal holder and counter weight 95. The MR docking station then is placed concentrically into the MR coil to be imaged. The user can adjust the depth to which the animal cassette is placed into the MR coil by sliding the MR depth adjustment 98 and the depth is noted by MR depth readout 97. There can be provisions to pass heated air over the animal body in order to prevent hypothermia from long imaging sessions, along with a gas anesthesia inlet 99 to keep the animal sedated. Gas block 109 permits the delivery of anesthesia to the holder when the holder is placed in the adapter. Anesthesia is routed through tubing (not shown) which is connected to anesthesia inlet 99. The anesthesia passes through the inlet 99 and gas block 109 to the cavity of the adapter that houses the animal holder (denoted as IA in FIG. 35).

Figure 36:
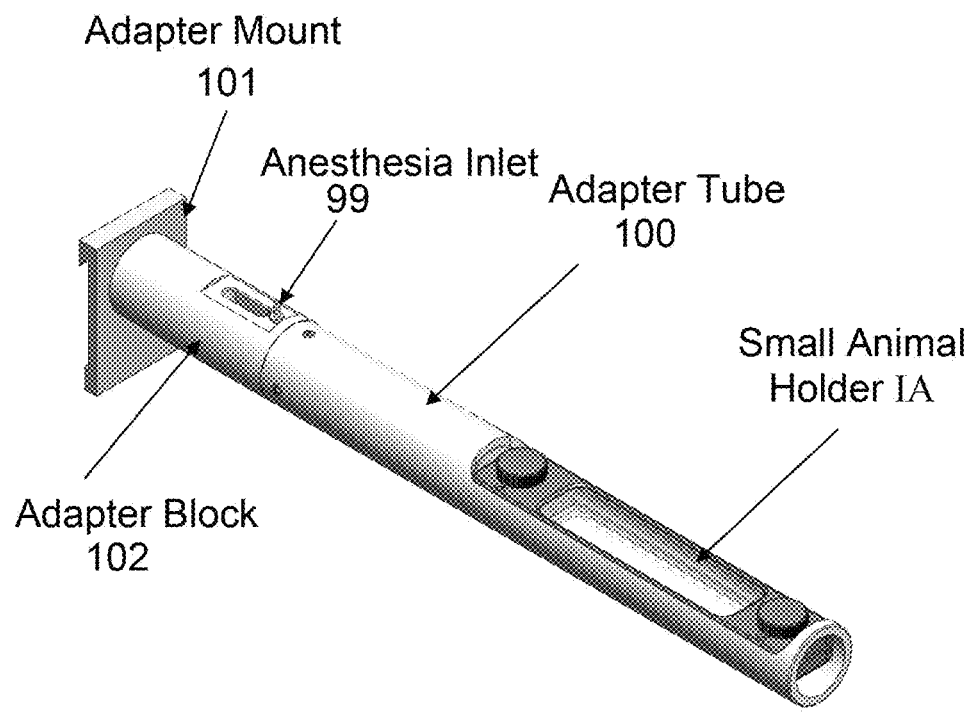
FIG. 36 is an isometric view of an internal animal cassette docking station designed for imaging animals within a CT system, according to an illustrative embodiment of the invention.
Figure 37:
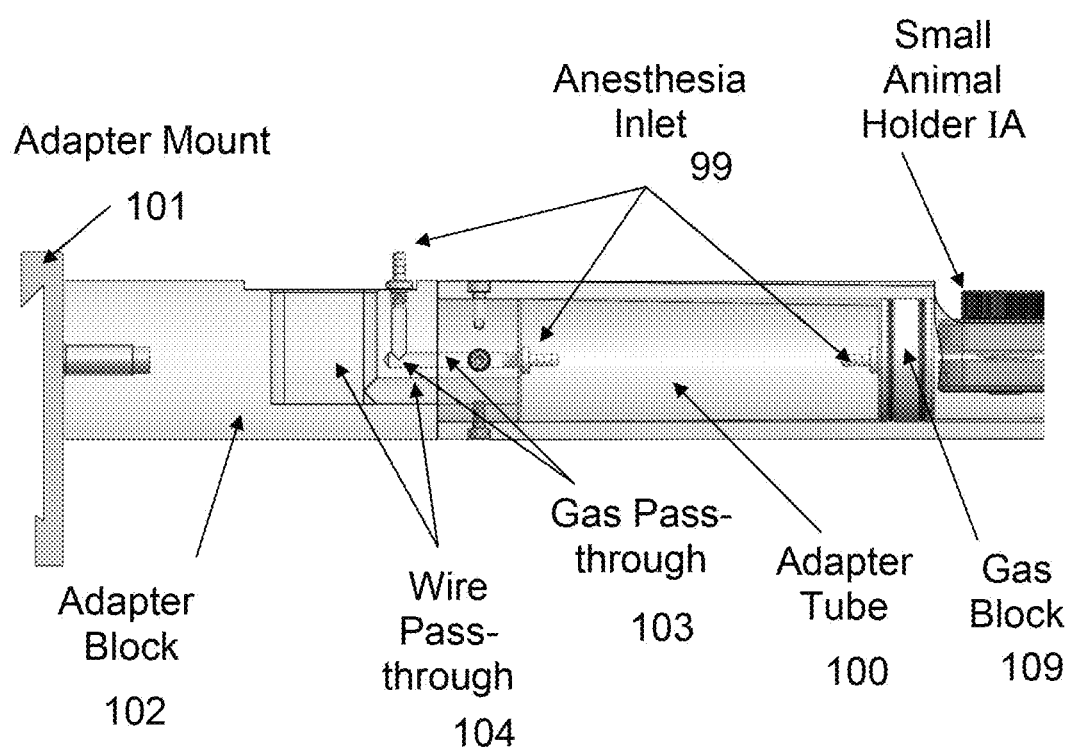
FIG. 37 is a partial side view of an internal animal cassette docking station designed for imaging animals within a CT system detailing the gas anesthesia connections, according to an illustrative embodiment of the invention.
Figure 38:
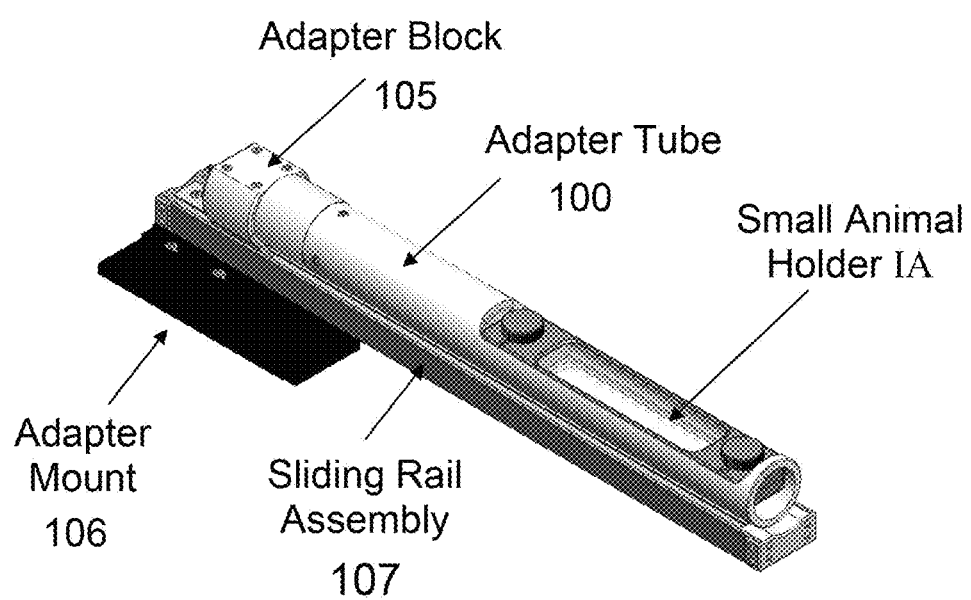
FIG. 38 is an isometric view of an internal animal cassette docking station designed for imaging animals within a different CT system, according to an illustrative embodiment of the invention.
Figure 39:
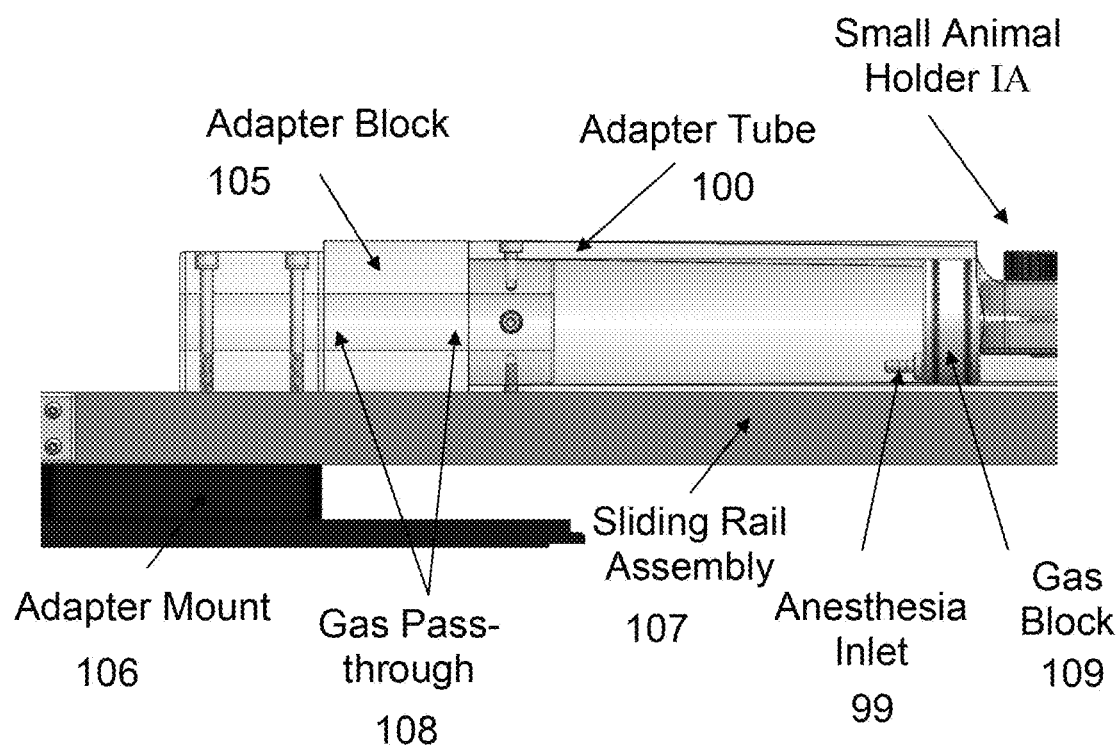
FIG. 39 is a partial side view of an internal animal cassette docking station designed for imaging animals within a different CT system detailing the gas anesthesia connections, according to an illustrative embodiment of the invention.
Figure 40:
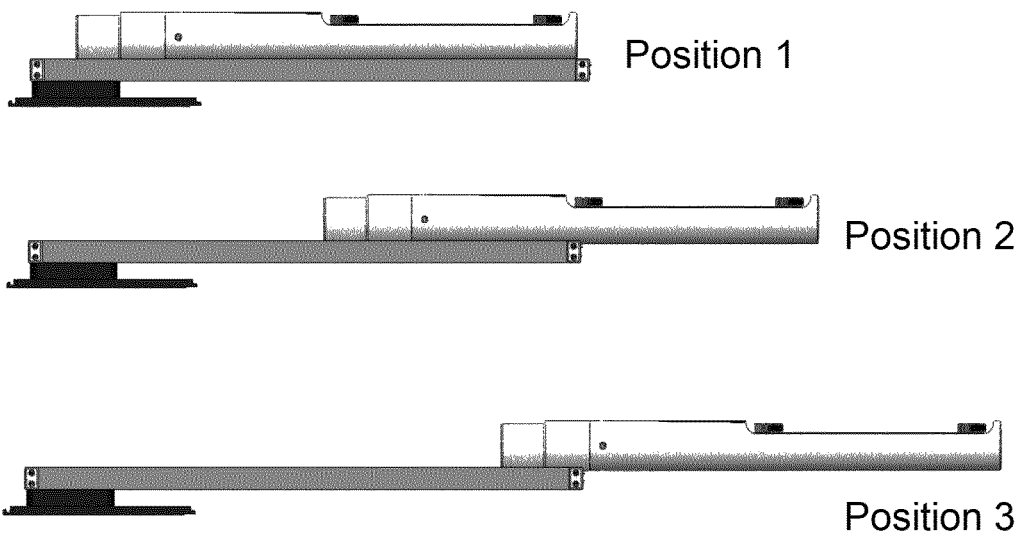
FIG. 40 is a series of side views of an internal animal cassette docking station designed for imaging animals within a different CT system detailing three positions of the sliding rail, according to an illustrative embodiment of the invention.

FIGS. 36-42 depict three different CT mounts (Gamma Medica, Siemens Inveon, and GE CT) that allow the small animal holder to mount into three different CT systems. FIG. 36 shows small animal holder IA disposed within a CT mount containing an adapter tube 100 connected to adapter mount 101 via adapter block 102 that further defines anesthesia inlet 99. The anesthesia system is shown more specifically in FIG. 37 where anesthesia is introduced through anesthesia inlet 99 and passes through gas pass through 103. FIGS. 38 and 39 show the small animal holder IA disposed in adapter tube 100, which is connected to adapter block 105. The animal holder can be moved via sliding rail assembly 107 that translates relative to the adapter mount 106. Anesthesia can be introduced via gas pass through 108. As shown in FIG. 40, the animal holder can translate through a plurality of positions referred to as position 1, position 2, and position 3.

Figure 41:
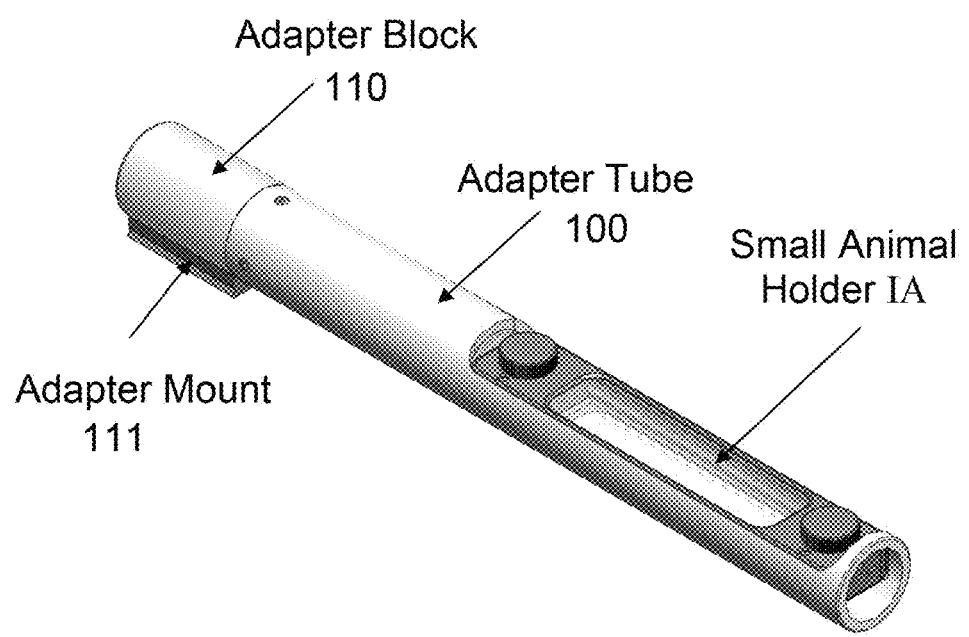
FIG. 41 is an isometric view of an internal animal cassette docking station designed for imaging animals within a different CT system, according to an illustrative embodiment of the invention.
Figure 42:
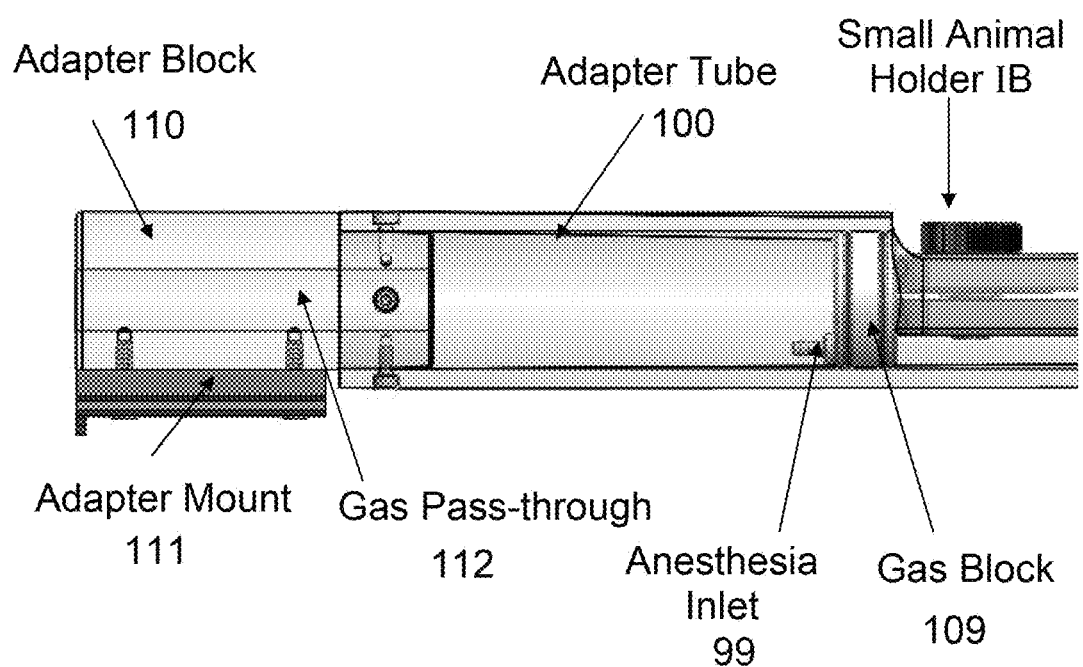
FIG. 42 is a partial side view of an internal animal cassette docking station designed for imaging animals within a different CT system detailing the gas anesthesia connections, according to an illustrative embodiment of the invention.

FIGS. 41 and 42 show another CT mount, where animal holder IA is placed within adapter tube 100, which is connected to adapter block 110 that contains adapter mount 111.

Figure 43:
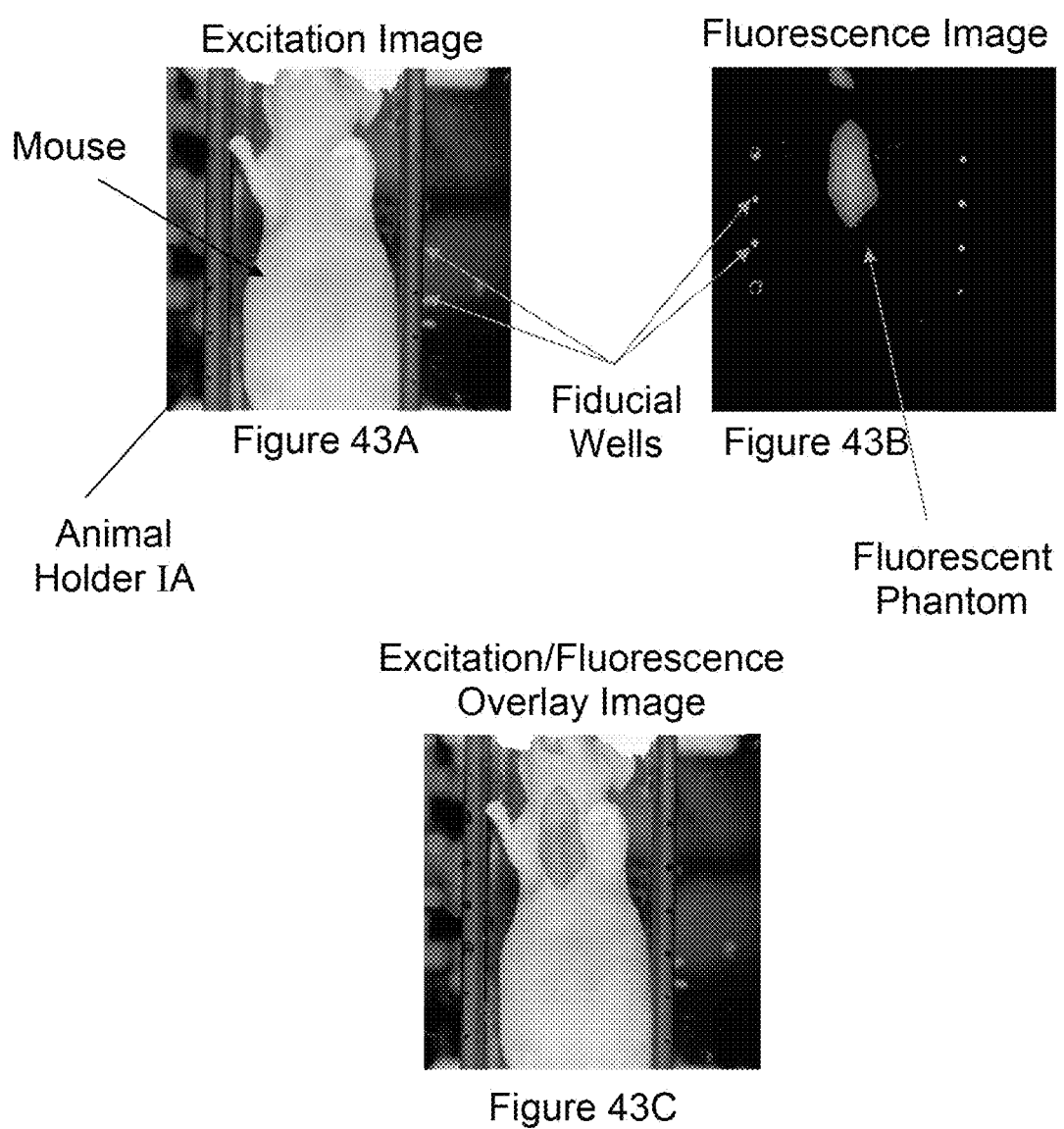
FIG. 43 shows excitation and fluorescence images of a mouse being imaged within the animal cassette, according to an illustrative embodiment of the invention.
Figure 44:
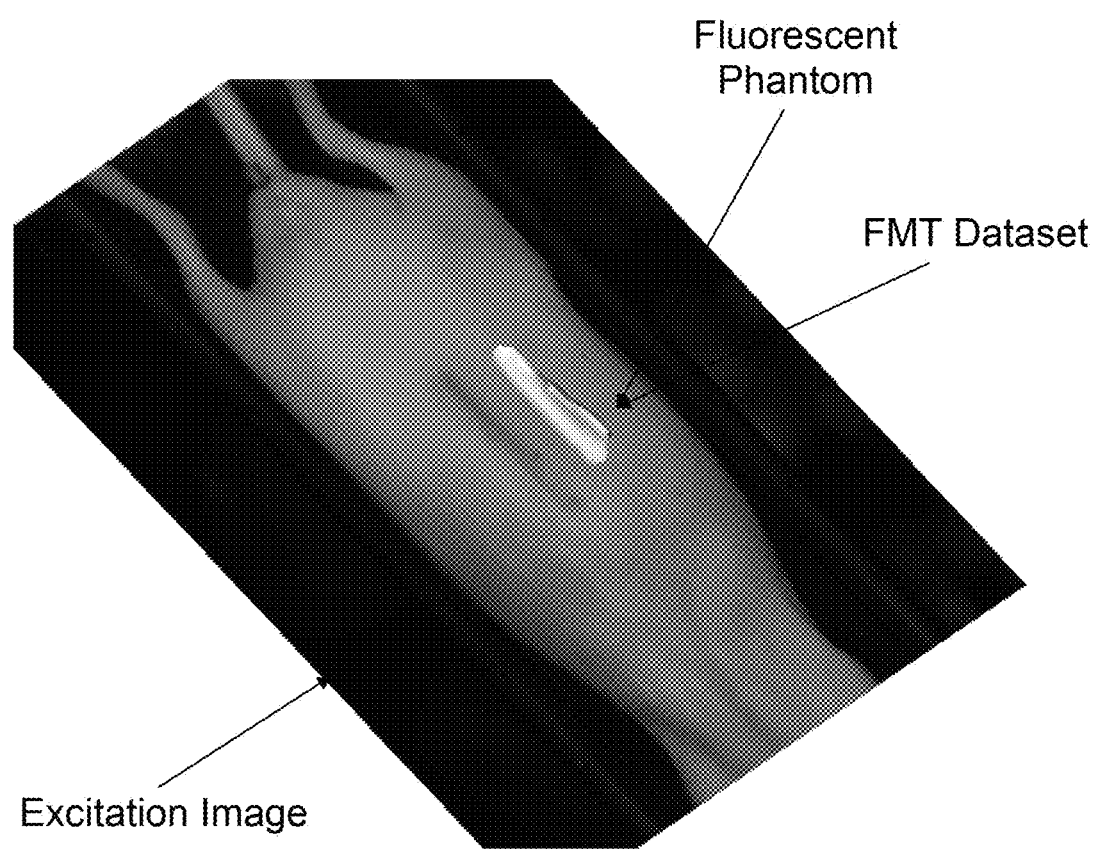
FIG. 44 shows an isometric view of an FMT dataset overlaid upon an excitation image of a mouse with a fluorescence phantom disposed within the abdomen imaged within an animal holder, according to an illustrative embodiment of the invention.
Figure 45:
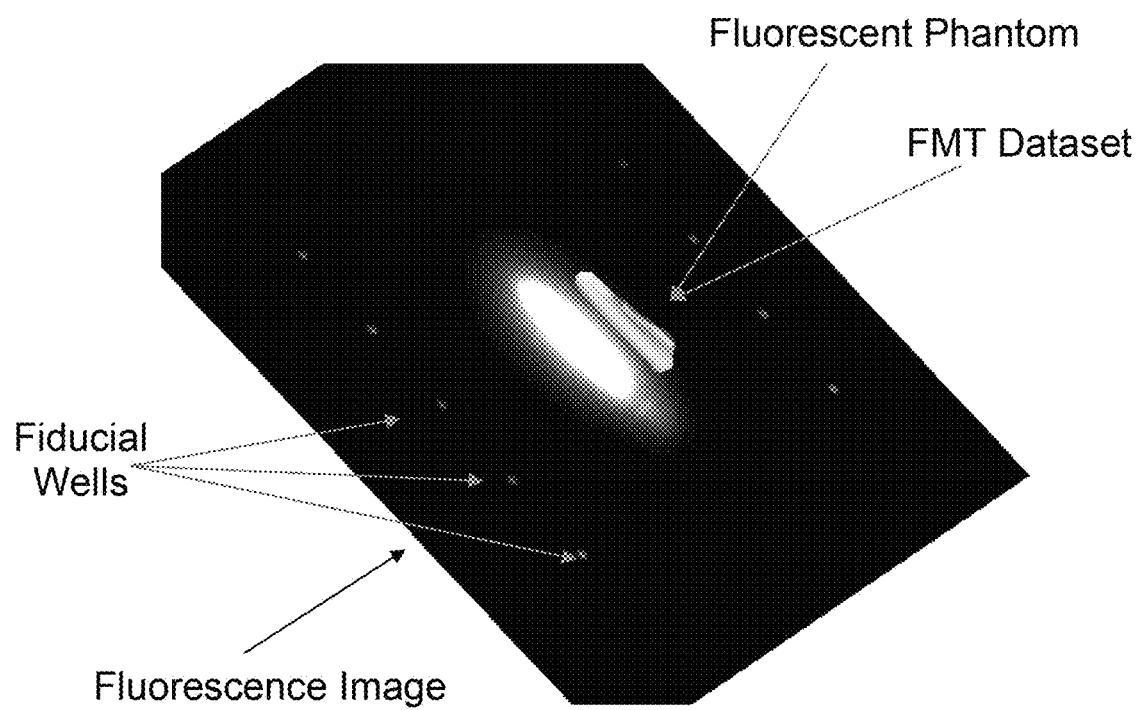
FIG. 45 shows an isometric view of an FMT dataset overlaid upon a fluorescence image of a mouse with a fluorescence phantom disposed within the abdomen imaged within an animal holder, according to an illustrative embodiment of the invention.

FIG. 43-48 depict images of a mouse imaged in an animal holder of the invention. FIG. 43 show an excitation image (FIG. 43A), a fluorescence image (FIG. 43B), and overlayed excitation and fluorescence images (FIGS. 43C). The mouse is shown in animal holder IA, where the fiducial wells are visible in both the excitation image (FIG. 43A) and the fluorescence image (FIG. 43B). The fluorescence images also show the fluorescent phantom (see FIGS. 43B and 43C).

Figure 46:
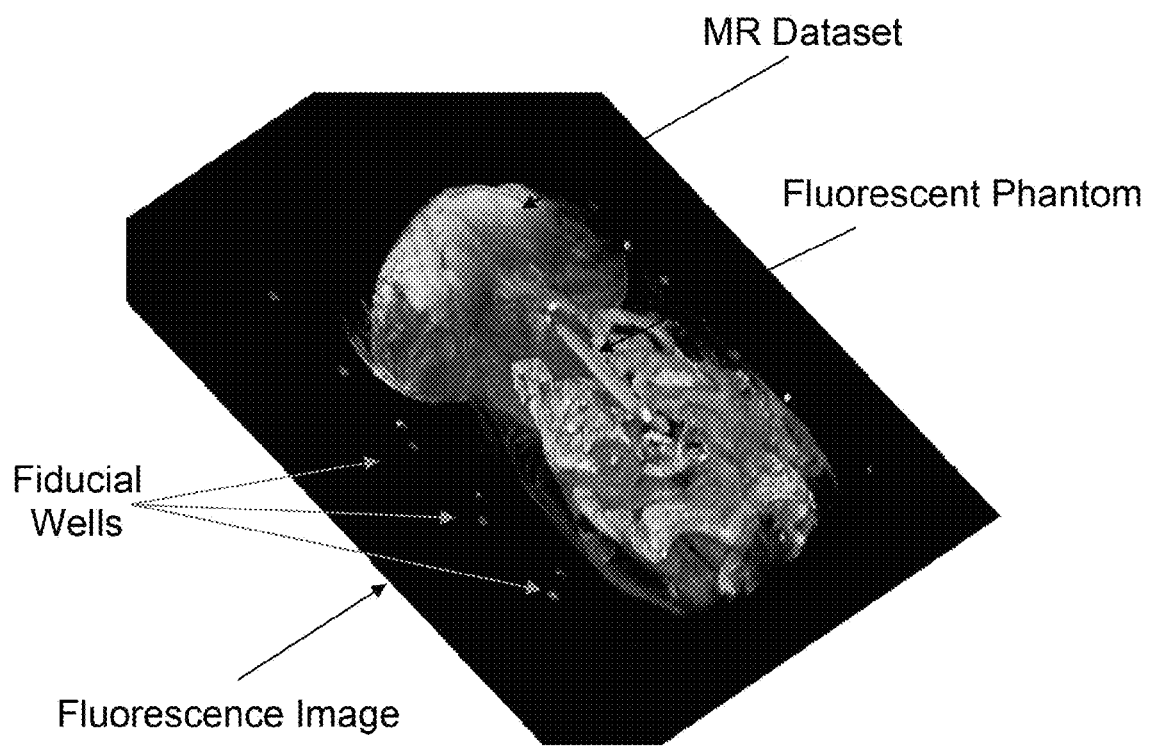
FIG. 46 shows an isometric view of an MR dataset overlaid upon an fluorescence image of a mouse with a fluorescence phantom disposed within the abdomen imaged within an animal holder, according to an illustrative embodiment of the invention.
Figure 47:
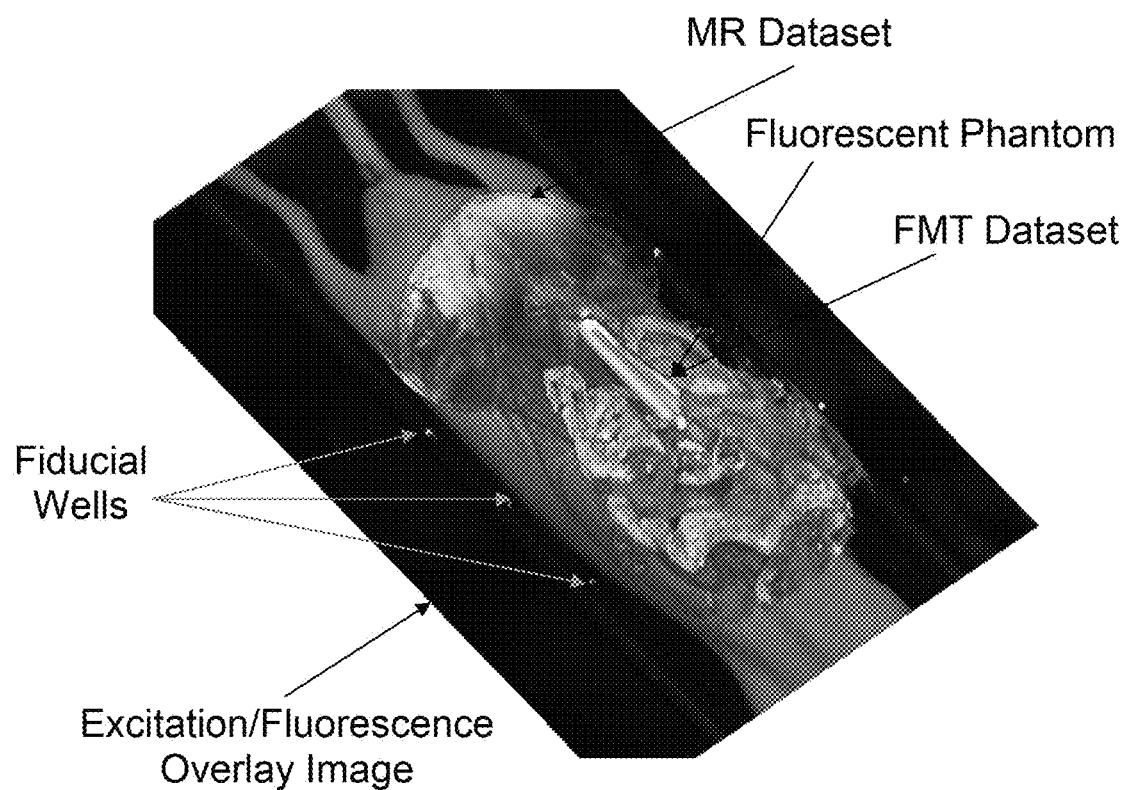
FIG. 47 shows an isometric view of a fusion of a FMT dataset and a MR dataset overlaid upon an excitation/fluorescence overlay image of a mouse with a fluorescence phantom disposed within the abdomen imaged within an animal holder, according to an illustrative embodiment of the invention.
Figure 48:
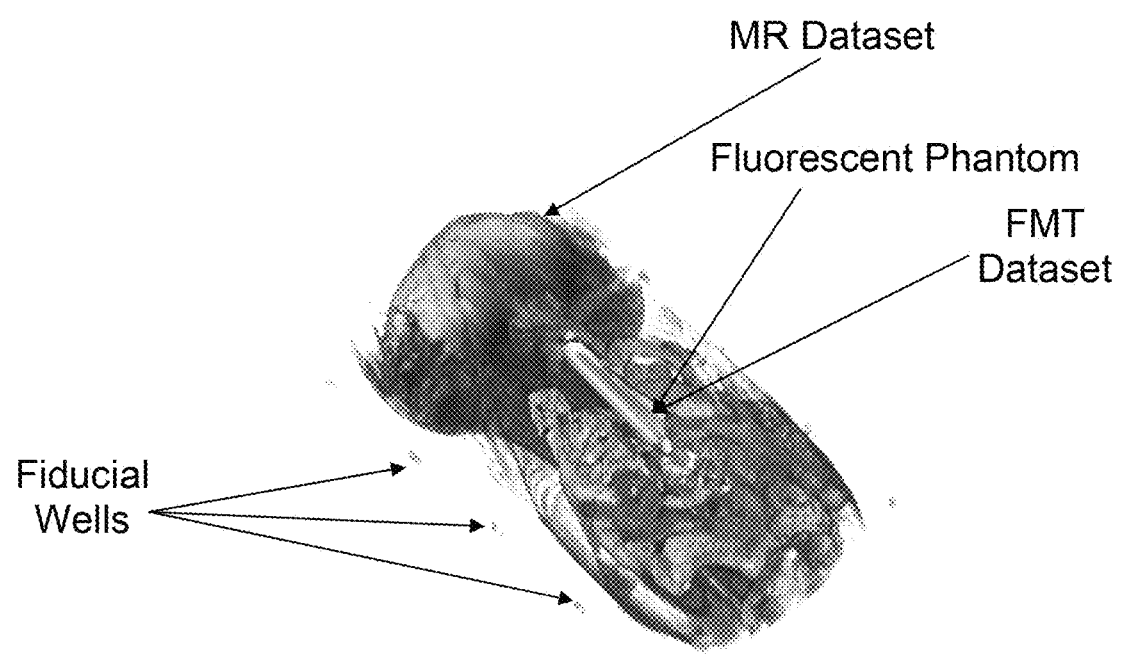
FIG. 48 shows an isometric view of a fusion of a FMT dataset and a MR dataset of a mouse with a fluorescence phantom disposed within the abdomen imaged within an animal holder, according to an illustrative embodiment of the invention.

FIGS. 44-48 illustrate fused MR and FMT images of a mouse with a phantom filled with Alexa Fluor 680 (Invitrogen, Carlsbad, Calif.) inserted into the mouse's abdomen. The excitation and fluorescence images (FIG. 44 and FIG. 45, respectively), both of which are overlayed with the FMT dataset, clearly show the location of the fluorescence phantom within the mouse and the fiducial wells. The fluorescence image was registered with the MR dataset using the fiducial wells in each dataset to determine the relative locations of the two datasets, as shown in FIG. 46. Fused images of the FMT and MR datasets are shown in FIGS. 47-48, which clearly show the correlation between the FMT and MR data, as indicated by the co-localization of the phantom in the FMT reconstruction and the MR scan. The images demonstrate that the animal holder can be used to facilitate imaging across multiple modalities and to facilitate co-registration of the resulting images.

Figure 49:
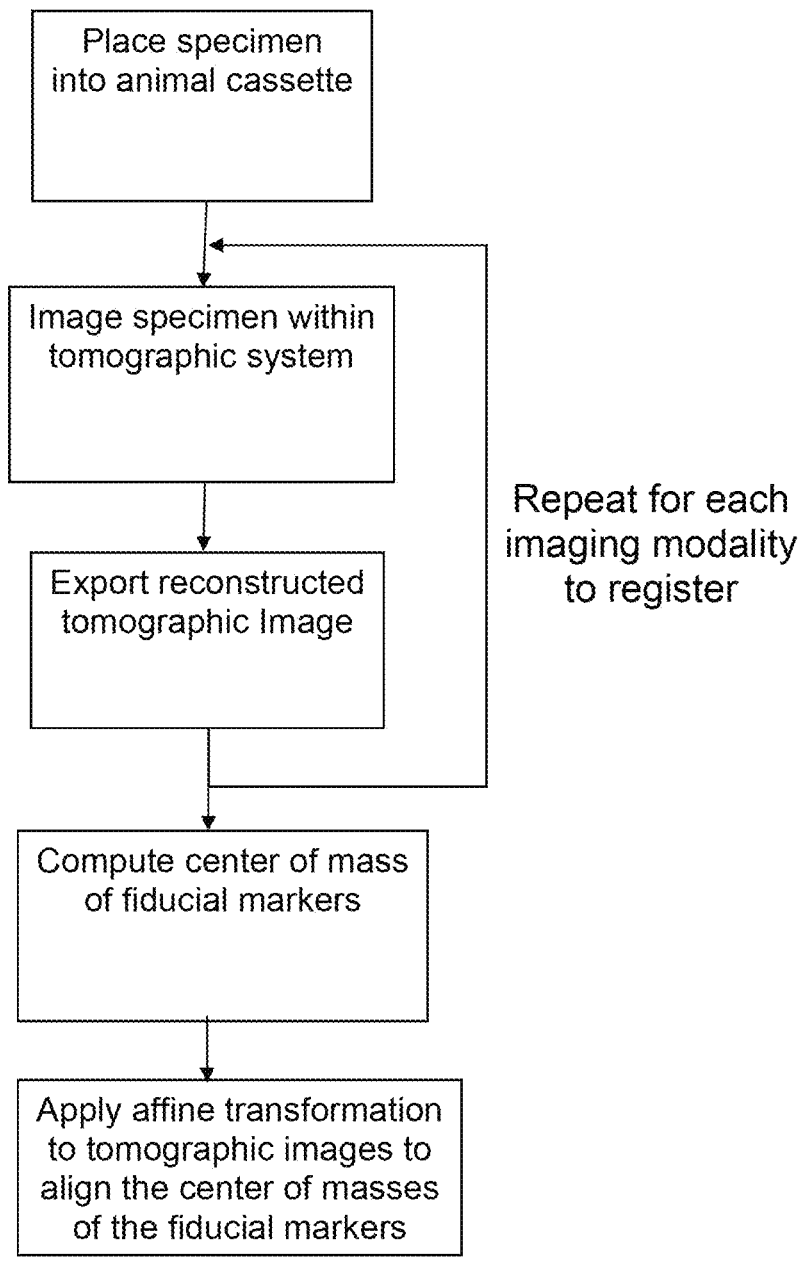
FIG. 49 is a flow chart showing steps in a process to fuse MR, CT and FMT imaging modalities of a small animal imaged in the animal holder according to an illustrative embodiment of the invention.

FIG. 49 is a flow chart illustrating the process of fusing two or more datasets from the tomographic imaging systems. Instructions for an exemplary multimodality imaging session include: (1) placing the animal into the animal holder, (2) imaging the animal in a tomographic system once fiducial wells have been filled with appropriate marker (if needed), (3) exporting the reconstructed tomographic image using relevant software, and (4) repeating steps 2 and 3 for each modality the user is interested in. Once all the datasets have been collected, the user then can fuse the datasets via software such as Amira (Visage Imaging, Carlsbad, Calif.) (see FIG. 50). If the dataset is an FMT dataset, the user can compute the center of mass of at least two fiducial wells from the reflectance images, giving the x and y locations of each fiducial. The z location of the fiducial can be computed from the adjustment knob height and knowing the fiducial well offsets within the animal holder. If the dataset is from an MR or CT system, the center of mass of at least three fiducial wells can be found in the tomographic data, giving their x,y,z coordinates. To fuse the datasets, an affine transformation (scale and rotate) is applied to all but one dataset such that the x,y,z locations match. In one embodiment, the user can apply a least squares error fitting scheme to compute the appropriate affine transformation. Once the datasets have been scaled and aligned properly then they can be displayed, for example, as shown in FIGS. 47 and 48.

Figure 50:
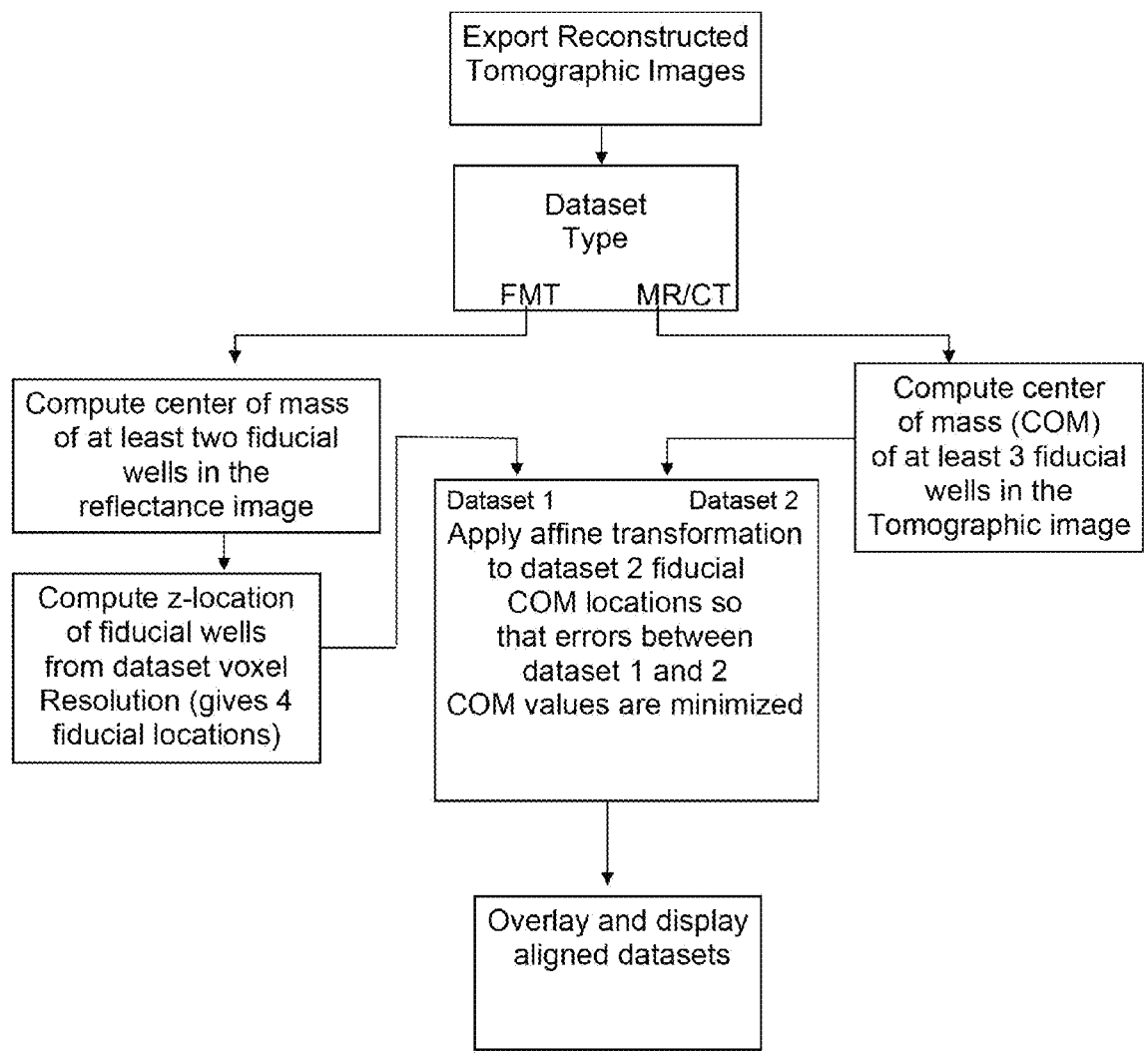
FIG. 50 is a flow chart showing steps in a process to align imaged fiducial markers from MR, CT and FMT imaging modalities of a small animal imaged in the animal holder according to an illustrative embodiment of the invention.

As depicted in FIG. 50, when registering an FMT dataset with that from another modality, a first step in the co-registration process is the extraction of centers of mass (COM) of a plurality of fiducial markers. As these fiducial markers are imaged in reflectance, the location of the centers of mass can be computed based on an optical reflectance image, as part of the FMT acquisition. The optical reflectance image, FMT tomographic dataset, and other modality tomographic dataset can then be co-registered. It is also possible to import this same fiducial information into the FMT tomographic reconstructed dataset directly and integrate the fiducial marker information within the voxel mesh. One of the benefits of such an approach includes eliminating one step in the general process of fusing FMT and other modality datasets together, so that only two datasets (FMT and other modality) need to be co-registered instead of three.

Figure 51:
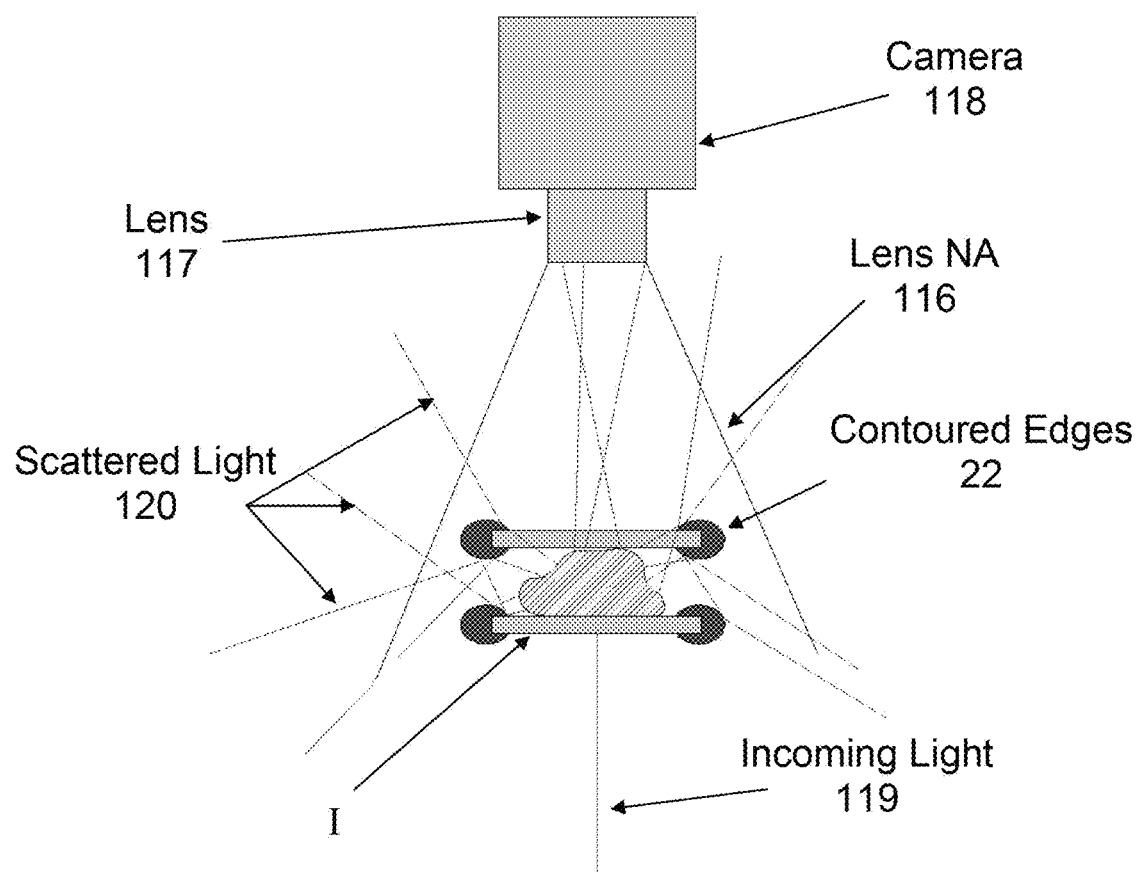
FIG. 51 illustrates the contoured edges of the top and bottom trays (frames) of the portable animal cassettes to reduce stray light reflections into the numerical aperture (NA) of the imaging device during reflectance and tomographic imaging, according to an illustrative embodiment of the invention.

FIG. 51 shows an exemplary animal holder I having contoured edges 22 of the top tray and the bottom tray to reduce stray light reflections into the numerical aperture (NA) 116 of the imaging device, which as shown includes lens 117 and camera 118, during reflectance and tomographic imaging. During trans-illumination imaging, the incoming light 119 passes through the animal and diffuses through the animal tissue. The diffusion process scatters the light in random directions resulting in the scattered light 120 emanating from the mouse tissue in all directions. The stray light emanating from the animal preferably is reflected away from the camera in order to reduce their effects upon the automatic camera exposure settings. As shown in FIG. 51, the stray light emanating from the animal or from around the animal hits the contoured edges of the animal holder, which re-direct the reflected light outside the numerical aperture of the objective lens or other optical device placed in front of the detector. As the reflected and re-directed stray light falls outside the numerical aperture or acceptance cone of the detector optics, such stray light will have little or no disruptive impact on the detection of useful signal, which enhances the signal to noise ratio of the detection technique.

EXAMPLE 1

Multi-modality Imaging using the Animal Holder

An example of multi-modality imaging is depicted in FIGS. 46-48. Alexa Fluor 680 (AF 680) dye (Invitrogen, Carlsbad, Calif.) was dissolved in water and injected into a plastic imaging phantom. The imaging phantom was surgically inserted subcutaneously into the thoracic cavity of an adult NU/NU mouse (Charles River Laboratories, Wilmington, Mass.). The mouse then was placed into an animal holder of the invention and secured for imaging before the entire cassette was placed inside an FMT2500 imaging system (VisEn Medical, Inc., Bedford, Mass.). Free dye dissolved in water (AF 680) was injected into the fiducial wells of the animal holder. An FMT imaging dataset was collected and subsequent reconstruction was performed using software included in the FMT2500. The animal holder containing the same mouse then was placed inside a 7 Tesla Bruker MR system (Bruker BioSpin, Billerica, Mass.) and an MR dataset was collected using Paravision 4 acquisition software. Fusion of the FMT and MR datasets was performed using Amira software (Visage Imaging, Carlsbad, Calif.). This demonstrates the use of an animal holder of the invention for performing multi-modality experiments on the same animal and co-registering the resulting imaging data to produce an accurate composite image.

Incorporation By Reference

The teachings of all the references, patents and patent applications cited herein are expressly incorporated by reference herein in their entirety for all purposes.

The text of the following documents is incorporated herein by reference and this subject matter may be applied in the embodiments described herein: U.S. Pat. No. 6,615,063; U.S. Patent Application Publication No. US2004/0015062; International (PCT) Patent Application Publication No. WO03/102558; International (PCT) Patent Application Publication No. WO2004/072906; and International (PCT) Patent Application Publication No. WO2007/111669.

Equivalents

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A portable animal holder configured for use in one or more in vivo imaging systems, the portable animal holder comprising:
   a first frame and a first imaging window, wherein the first imaging window is secured to the first frame;
   a second frame and a second imaging window, wherein
      the second imaging window is secured to the second frame, and
      each of the first imaging window and the second imaging window is composed of a material transparent to electromagnetic radiation; and
   an adjustment mechanism to adjust a spacing between the first imaging window and the second imaging window, wherein
      the adjustment mechanism is configured, upon adjustment, to maintain substantial parallelism between the first imaging window and the second imaging window,
      such that the first frame and the second frame are only connected to each other via the adjustment mechanism, thereby maintaining a gap between the first frame and the second frame, and
      the portable animal holder is configured, upon adjustment, to prevent movement of the animal positioned between the first frame and the second frame during imaging of the animal in the one or more in vivo imaging systems;
   wherein, upon positioning of the animal,
      a first portion of the animal is flush to the first imaging window,
      a second portion of the animal is flush to the second imaging window, and
      the animal is arranged such that electromagnetic radiation can pass through the first imaging window, the animal, and the second imaging window during in vivo imaging.

2. The portable animal holder of claim 1, wherein each of said imaging windows permits transmission therethrough of at least one member selected from a group consisting of X-rays, gamma rays, positron rays, visible light, near-infrared light, radio waves, micro-waves, tetra-hertz radiation, infrared light, and ultraviolet light.

3. The portable animal holder of claim 1, wherein the material is selected from a group consisting of glass, acrylic, resin, and plastic.

4. The portable animal holder of claim 1, wherein each of said imaging windows comprises an antireflective coating.

5. The portable animal holder of claim 1, wherein each of said frames comprises polyoxymethylene, acrylonitrile butadiene styrene (ABS), or other plastic.

6. The portable animal holder of claim 1, wherein said animal holder is composed of non-metallic material.

7. The animal holder of claim 1, wherein said imaging windows are parallel, thereby providing two planar boundary conditions for three-dimensional image reconstruction of at least a portion of said animal upon positioning of said animal between said parallel imaging windows.

8. The portable animal holder of claim 1, said animal holder further comprising at least one of (a) a plurality of fiducial markers and (b) a plurality of wells adapted to accommodate fiducial markers.

9. The portable animal holder of claim 8, wherein said animal holder is configured to permit transport of said animal within said animal holder as a rigid body or pseudo-rigid body from a first imaging location to a second, different imaging location, said fiducial markers allowing co-registration of data sets obtained at said first and said second imaging locations.

10. The portable animal holder of claim 9, wherein at least a subset of said fiducial markers is detectable by both a first imaging modality and a second imaging modality.

11. The portable animal holder of claim 10, wherein said first imaging modality is performed with said animal at said first imaging location and said second imaging modality is performed with said animal at said second imaging location.

12. The portable animal holder of claim 10, wherein said first imaging modality and said second imaging modality are each selected from a group consisting of magnetic resonance, X-ray, X-ray computed tomography, nuclear, positron emission tomography (PET), single photon emission computed tomography (SPECT), ultrasound, fluorescence, fluorescence tomography, and bioluminescence imaging.

13. The portable animal holder of claim 10, wherein said first and said second imaging modalities comprise two members selected from a group consisting of fluorescence molecular tomography (FMT), magnetic resonance (MR), and X-ray computed tomography (CT).

14. The portable animal holder of claim 10, wherein one of said first and said second imaging modalities is fluorescence molecular tomography (FMT) imaging and the other of said first and said second imaging modalities is magnetic resonance (MR) imaging or X-ray computed tomography (CT) imaging.

15. The portable animal holder of claim 10, wherein at least one of said fiducial markers comprises one or more members selected from a group consisting of a fluorescent compound, a gamma emitting compound, a positron emitting compound, a silicon polymer, and a metal.

16. The portable animal holder of claim 8, wherein the plurality of wells are configured to accept insertion of a solid or liquid marker substance therein to provide said plurality of fiducial markers.

17. The portable animal holder of claim 8, wherein at least one of said fiducial markers comprises one or more members selected from a group consisting of an organic fluorophore, an inorganic fluorophore, indocyanine dye, quantum dots, a visible-wavelength fluorophore, an infra-red fluorophore, a superparamagnetic agent, and a radioactive agent.

18. The portable animal holder of claim 1, further comprising an inlet for delivery of anesthesia to said animal.

19. The portable animal holder of claim 1, further comprising a heater for maintaining said animal within a given temperature range during a period of time comprising at least one of (a) before imaging and (b) during imaging.

20. The portable animal holder of claim 1, wherein each of said frames comprises one or more contoured edges for reducing stray light reflection.

21. The portable animal holder of claim 1, said animal holder configured for placement within a docking station, wherein the docking station is configured for delivery to the animal, prior to imaging, of at least one of anesthesia and heat.

22. The animal holder of claim 1, further comprising an inlet for delivery of anesthesia to said animal.

23. A method of imaging a region within an animal, the method comprising:
administering to an animal a probe comprising a fluorophore;
positioning said animal in relation to a portable animal holder comprising a first frame comprising a first imaging window, and
a second frame comprising a second imaging window, wherein
each of the first imaging window and the second imaging window is composed of a material that permits transmission of electromagnetic radiation therethrough;
securing said animal between said frames, thereby preventing substantial movement of said animal during imaging, and thereby providing two planar boundary conditions, wherein
securing said animal between said frames comprises adjusting a spacing between the first frame and the second frame such that a first portion of the animal is flush to the first imaging window and a second portion of the animal is flush to the second imaging window, and
the animal is positioned between the first frame and the second frame, wherein the first frame and the second frame are only connected to each other via the adjustment mechanism such that a gap exists between the first frame and the second frame, and
an adjustment mechanism functions to maintain parallel separation between the first imaging window and the second imaging window;
positioning said animal holder within a fluorescence molecular tomography (FMT) imaging device configured to accept said animal holder;
directing excitation light, through an imaging window of said animal holder, into said animal at multiple locations to transilluminate at least a portion of said animal;
detecting fluorescent light emitted from the probe within said animal and transmitted through the opposite imaging window of said animal holder; and
processing data corresponding to said detected emitted fluorescent light to provide a tomographic representation of said region within said animal, wherein said two planar boundary conditions are used in providing said tomographic representation.

24. The method of claim 23, wherein said portable animal holder comprises a plurality of fiducial markers and wherein the method further comprises:
detecting locations of said plurality of fiducial markers in relation to said animal while said animal holder is within said FMT imaging device;
positioning said animal holder within a non-FMT imaging device configured to accept said animal holder;
obtaining image data from at least a portion of said animal with said non-FMT imaging device and detecting locations of said plurality of fiducial markers in relation to said animal while said animal holder is within said non-FMT imaging device; and
co-registering said tomographic representation obtained using said FMT imaging device with image data obtained using said non-FMT imaging device to produce a composite image of said region within said animal.

25. The method of claim 24, wherein said non-FMT imaging device is a magnetic resonance (MR) imaging device or an X-ray computed tomography (CT) device.

26. The method of claim 24, wherein co-registering said tomographic representation comprises co-registering said tomographic representation obtained using said FMT imaging device with said image data obtained using said non-FMT imaging device using one or more affine transformations.

27. The method of claim 24, wherein at least one of said plurality of fiducial markers comprises one or more members selected from a group consisting of a fluorescent compound, a gamma emitting compound, a positron emitting compound, a silicon polymer, and a metal.

28. The method of claim 24, wherein said animal holder comprises a plurality of wells for insertion of a solid or liquid marker substance therein to provide said fiducial markers.

29. The method of claim 24, wherein at least one of said plurality of fiducial markers comprises one or more members selected from a group consisting of an organic fluorophore, an inorganic fluorophore, indocyanine dye, quantum dots, a visible-wavelength fluorophore, an infra-red fluorophore, a superparamagnetic agent, and a radioactive agent.

30. A method of imaging a region within an animal, the method comprising:
positioning an animal between a first frame and a second frame of a portable animal holder, wherein
the first frame comprises a first imaging window, and
the second frame comprises a second imaging window, wherein
each of the first imaging window and the second imaging window is composed of a material that permits transmission of electromagnetic radiation therethrough;
securing said animal between said frames, thereby preventing substantial movement of said animal during imaging and thereby permitting transport of said animal within said animal holder as a rigid body or pseudo-rigid body, wherein securing said animal between said frames comprises adjusting a spacing between the first frame and the second frame such that a first portion of the animal is flush to the first imaging window and a second portion of the animal is flush to the second imaging window, wherein
the animal is positioned between the first frame and the second frame, wherein the first frame and the second frame are only connected to each other via the adjustment mechanism such that a gap exists between the first frame and the second frame;
positioning said animal holder within a first imaging device configured to accept said animal holder;
obtaining image data using said first imaging device;
removing said animal holder from said first imaging device and positioning said animal holder within a second imaging device configured to accept said animal holder;
obtaining image data using said second imaging device; and
co-registering image data obtained from said first imaging device and said second imaging device to produce a composite image of a region within said animal.

31. The method of claim 30, wherein co-registering said image data comprises co-registering said image data using one or more affine transformations.

32. The method of claim 30, wherein said animal holder comprises a plurality of fiducial markers, wherein said method comprises detecting a position of each of one or more of said fiducial markers, and wherein co-registering said image data comprises co-registering said image data using one or more of said fiducial markers.

33. The method of claim 30, further comprising, after securing said animal between said frames:
positioning the portable animal holder within a docking station configured to receive said portable animal holder, wherein positioning said animal holder within said first imaging device comprises positioning said docking station within said first imaging device; and
delivering anesthesia to said animal while the docking station is positioned within said first imaging device.

34. The method of claim 33, wherein said docking station comprises a slot configured to receive the portable animal holder.

35. A system for imaging a region within an animal, comprising:
a portable animal holder comprising:
a first tray comprising a first imaging window;
a second tray comprising a second imaging window, wherein each of the first imaging window and the second imaging window is composed of a material transparent to electromagnetic radiation; and
an adjustment mechanism to adjust a spacing between the first tray and the second tray, wherein the first tray and the second tray are only connected to each other via the adjustment mechanism, wherein
the adjustment mechanism is configured, upon adjustment, to maintain substantial parallelism between the first tray and the second tray, and
the portable animal holder is configured, upon adjustment, to prevent movement of an animal positioned between the first tray and the second tray during imaging of the animal in an imaging chamber; and
a docking station comprising an anesthesia plenum, at least one window composed of material transparent to electromagnetic radiation, and a slot, wherein
the slot is configured to replaceably accept the animal holder, and
upon positioning of the portable animal holder within the docking station, anesthesia is delivered to the animal via the anesthesia plenum;
wherein, upon positioning of the animal within the animal holder,
a first portion of the animal is flush to the first imaging window,
a second portion of the animal is flush to the second imaging window, and
the animal is arranged such that electromagnetic radiation can pass through the first imaging window, the animal, and the second imaging window during in vivo imaging within the imaging chamber, thereby providing two planar boundary conditions and facilitating tomographic reconstruction using data obtained during in vivo imaging of the animal.

36. The system of claim 35, wherein the docking station is configured to be releasably received within an aperture of the imaging chamber.

37. The system of claim 35, wherein the docking station comprises:
a sealable door wherein, upon positioning of the animal holder within the docking station, the sealable door is configured to seal the animal holder within the docking station; and
an exhaust port, wherein a vacuum connected to the exhaust port draws anesthesia supplied via the anesthesia plenum across the animal.

* * * * *